US00RE47285E

(19) United States
(12) Reissued Patent
Loske

(10) Patent Number: US RE47,285 E
(45) Date of Reissued Patent: Mar. 12, 2019

(54) VACUUM SYSTEM AND ENDOSCOPY ARRANGEMENT FOR ENDOSCOPIC VACUUM THERAPY

(71) Applicant: LOHMANN & RAUSCHER GMBH & CO. KG, Neuwied (DE)

(72) Inventor: Gunnar Loske, Ahrensburg (DE)

(73) Assignee: LOHMANN & RAUSCHER GMBH & CO. KG, Neuwied (DE)

(21) Appl. No.: 15/846,725

(22) Filed: Dec. 19, 2017

Related U.S. Patent Documents

Reissue of:
(64) Patent No.: 9,215,964
Issued: Dec. 22, 2015
Appl. No.: 14/004,313
PCT Filed: Mar. 12, 2012
PCT No.: PCT/EP2012/054276
§ 371 (c)(1),
(2) Date: Sep. 10, 2013
PCT Pub. No.: WO2012/123414
PCT Pub. Date: Sep. 20, 2012

(30) Foreign Application Priority Data

Mar. 11, 2011 (DE) ..... 10 2011 013 743
Mar. 11, 2011 (DE) ..... 10 2011 013 744
(Continued)

(51) Int. Cl.
*A61B 1/015* (2006.01)
*A61B 1/00* (2006.01)
*A61B 1/31* (2006.01)
*A61B 1/273* (2006.01)

(52) U.S. Cl.
CPC ..... *A61B 1/00094* (2013.01); *A61B 1/00073* (2013.01); *A61B 1/00082* (2013.01);
(Continued)

(58) Field of Classification Search
CPC ..... A61B 1/00094; A61B 1/00073; A61B 1/00082; A61B 1/00135; A61B 1/00154; A61B 1/015; A61B 1/273; A61B 1/31
(Continued)

(56) References Cited

U.S. PATENT DOCUMENTS 5,449,347 A * 9/1995 Preen et al. ..... 604/118
6,547,724 B1 * 4/2003 Soble ..... A61B 1/005 600/156
(Continued)

FOREIGN PATENT DOCUMENTS

DE 102009039515 3/2011

OTHER PUBLICATIONS

Weidenhagen, Rolf et al: "Anastomotic leakage after esophageal resection: new treatment options by endoluminal vacuum therapy.", Nov. 2010 (Nov. 2010), The Annals of Thoracic Surgery Nov. 2010, LNKD-PUBMED:20971288, vol. 90, NR. 5, pp. 1674-1681, XP002676647, ISN: 1552-6259 (8 pgs).
(Continued)

*Primary Examiner* — Beverly M. Flanagan
(74) *Attorney, Agent, or Firm* — Stinson Leonard Street LLP

(57) ABSTRACT

A vacuum system is described for endoscopic intracavity, intraluminal or intracorporeal vacuum therapy, for aspirating body fluids, wound secretions or gases from a hollow volume, such as a body cavity, a hollow organ, a tissue abscess or an intestinal lumen, particularly in the production of a temporary endoscopic closure of an intestinal lumen. Based on this, many embodiments of an endoscopy arrangement are described.

38 Claims, 55 Drawing Sheets

(30) Foreign Application Priority Data

Dec. 8, 2011 (DE) ..... 10 2011 120 411
Feb. 17, 2012 (DE) ..... 10 2012 003 129

(52) U.S. Cl.
CPC ..... *A61B 1/00135* (2013.01); *A61B 1/00154* (2013.01); *A61B 1/015* (2013.01); *A61B 1/273* (2013.01); *A61B 1/31* (2013.01)

(58) Field of Classification Search
USPC ..... 600/153, 154, 156, 158, 159; 604/313, 604/118–120, 319, 65, 369
See application file for complete search history.

(56) References Cited

U.S. PATENT DOCUMENTS

| | | | | |
|---|---|---|---|---|
| 7,022,113 | B2 * | 4/2006 | Lockwood et al. | 604/313 |
| 7,857,806 | B2 * | 12/2010 | Karpowicz | A61M 1/0031 601/6 |
| 8,743,425 | B2 * | 6/2014 | Simske et al. | 358/3.26 |
| 8,900,268 | B2 * | 12/2014 | Weidenhagen et al. | 606/215 |
| 2004/0093026 | A1 | 5/2004 | Weidenhagen | |
| 2009/0264837 | A1 * | 10/2009 | Adahan | A61M 1/0031 604/290 |

OTHER PUBLICATIONS

International Search Report for priority application PCT/EP2012/054276 dated Nov. 6, 2012 (3 pgs).
Translation of the International Preliminary Report on Patentability for priority application PCT/EP2012/054276 dated Sep. 26, 2013 (8 pgs).

* cited by examiner a
3625
3613E
3614
b
3613V
361
c
3625
d
e
f
g
h
i
j
k
l
m
n

Fig 55
e)
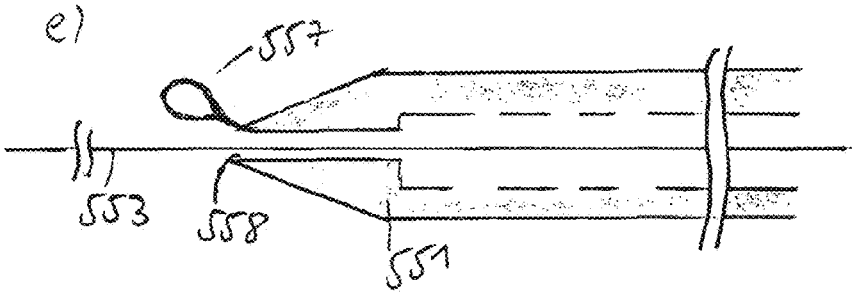
f)
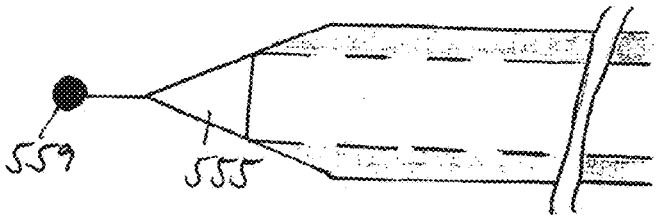
g)
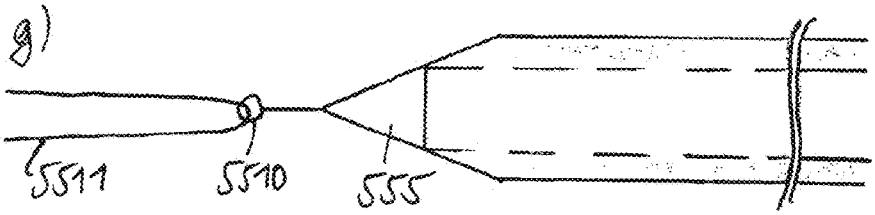
h)
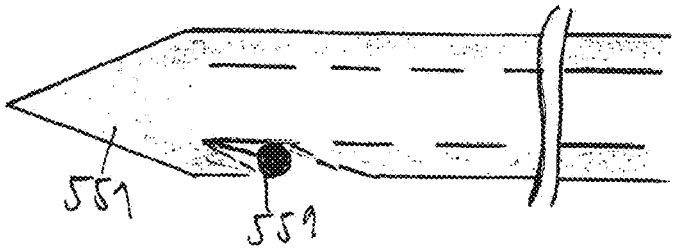

Fig. 56
e)
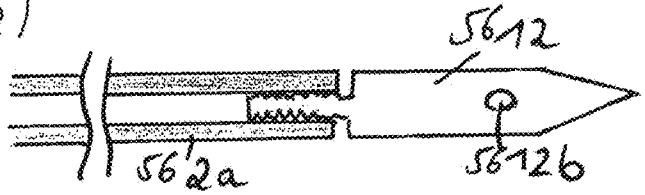
f)
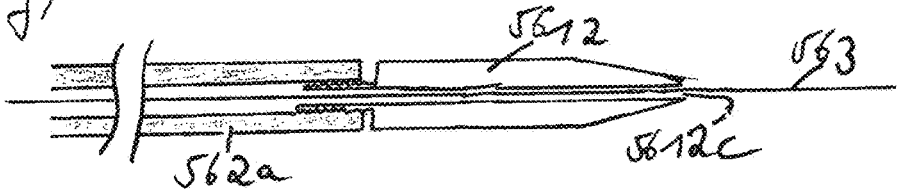

Fig 57
e)
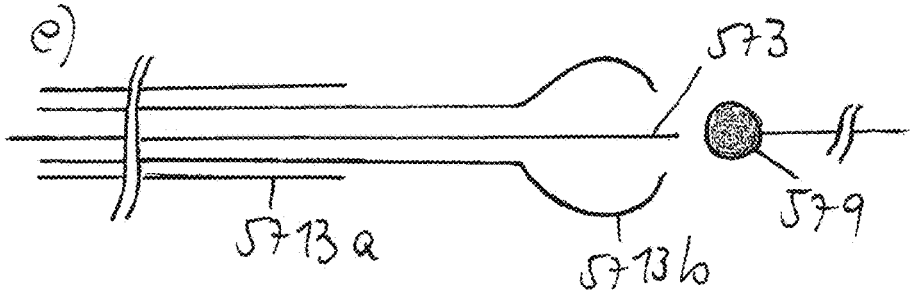
f)
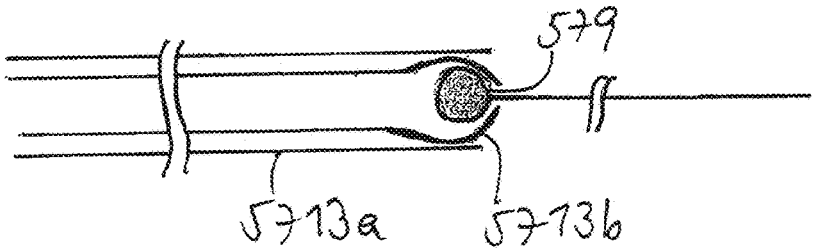

VACUUM SYSTEM AND ENDOSCOPY ARRANGEMENT FOR ENDOSCOPIC VACUUM THERAPY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The invention herein relates to a vacuum system and an endoscopy arrangement for endoscopic vacuum therapy, in particular for endoscopic intracorporeal, intraluminal or intracavitary vacuum therapy.

STATE OF THE ART

Endoscopic examinations of the upper and lower gastrointestinal tract (esophagogastroduodenoscopy/recto-, sigmoido-, ileocoloscopy, small bowel endoscopy) are diagnostic and therapeutic routine examinations.

The examination of the middle intestinal tract, especially the small intestine, is difficult because it is very long and extremely mobile. On the one hand, extra long endoscopes are used in the so-called push enteroscopy, on the other hand, the so-called single or double-balloon enteroscopy is used. For better advancement of the endoscope, the latter uses balloon systems on the endoscope and/or on the overtube; they are inflated during the examination and can press against the intestinal wall from inside. As a result, the endoscope or the overtube can become wedged against the intestinal wall, thereby allowing a deeper examination of the intestine. Another possibility of examining the intestine is a photographic record via a swallowable video capsule.

Conventional vacuum sponge therapy (low pressure wound therapy) is used for the treatment of external wounds. An open-cell polyurethane sponge or other fluid collection medium is placed into the wound, sealed by means of a film, and then subjected to a vacuum. Wound cleansing and wound healing can take place under this arrangement.

EXPLANATION OF THE INVENTION

According to the invention, a vacuum system for endoscopic intracavitary, intraluminal or intracorporeal vacuum therapy is proposed for the aspiration of body fluids, wound secretions or gases from a hollow space, such as a body cavity, a hollow organ, a tissue abscess or an intestinal lumen, especially while establishing a temporary endoscopic closure of an intestinal lumen. The vacuum system comprises:

A vacuum pump having a control input for receiving a control signal for control of its suction capacity and, on the negative pressure side, a connection for a vacuum drainage arrangement, and, connected or connectable to the control input of the vacuum pump, a pressure regulating unit having a test signal input for receiving at least one pressure test signal which forms a measurement for a pressure or negative pressure that prevails at the hollow space to be treated, and being designed, upon specification a) of a negative pressure value at the hollow space to be treated, which is selectable from a predefined negative pressure value interval, and b) of an evacuation period, the value of which is selectable between 0.5 and 5 seconds, i) figuring in a predetermined dead volume of the vacuum drainage arrangement that is connectable to the vacuum pump, to determine a first suction capacity of the vacuum pump, required for generating the specified negative pressure at the hollow space to be treated within the specified evacuation period, and to transmit a corresponding first control signal to the control input of the vacuum pump, ii) upon generating the specified negative pressure at the hollow space to be treated, to monitor the pressure test signal and to determine, as a function of the current pressure test signal, a second suction capacity of the vacuum pump, required for maintaining the specified negative pressure, and to transmit a corresponding second control signal to the control input of the vacuum pump; and iii) upon generating the specified negative pressure at the hollow space to be treated, if a deviation of the measured pressure or negative pressure from the specified negative pressure exists that exceeds a predefined threshold of the measured pressure or negative pressure, to determine a third suction capacity that is required for generating the specified negative pressure within the specified evacuation period and to transmit an appropriate third control signal to the control input of the vacuum pump, the vacuum pump being designed, as a function of the control signal currently being applied to its control input, to generate a suction capacity determined by the control signal.

Hereinafter, findings on which the invention is based, will first be explained in greater detail. Subsequently, exemplary embodiments will be presented.

The invention is based on the finding that the experience of vacuum therapy in external wounds is not applicable to endoscopic vacuum therapy. Based on this fact, it recognizes a rapid build-up of the vacuum with a short evacuation period as an essential technical prerequisite that can determine the success of an endoscopic vacuum treatment.

The requirements of a vacuum pump unit for endoscopic vacuum therapy can be specified as follows according to the invention: The negative pressure applied to a fluid collection element must be rapidly sufficiently high, so that the fluid collection element can be aspirated and adhere firmly to the surrounding tissue. The vacuum must not be too high, so that, via an open-pore structure of a fluid collection member to be connected, it can achieve a drainage effect on the surrounding tissue. The suction effect must not cause any injury to the aspirated tissue. In such cases, the adequate drainage effect at the wound is absent.

The suction capacity of the vacuum pump is, therefore, designed according to the invention herein and adjustable by means of the pressure regulating unit in such a way that a vacuum defined under these marginal conditions, can be built up within a very short period of time or at a rapid speed and can be maintained constant. The therapy would be ineffective if the parameters concerning the vacuum build-up were not to correspond to the specific requirements. Only with a rapid vacuum build-up and its maintenance and, rapid restoration of the vacuum in case of need, for example with a typical treatment indication, namely, the treatment of esophageal injuries, a closure of the perforation defect and effective wound drainage will be implemented at the same time. The permanently secured closure and the drainage against the physiological intrathoracic negative pressure in the direction of the esophageal lumen stops contamination by saliva or secretions toward the chest cavity and thus acts as a barrier to infection. In the case of any longer vacuum build-up and even with short interruptions of the specified negative pressure, a dislocation of a fluid collection element may occur. Any interrupted or ineffective suction at the wound bed leads to a standstill in therapy or deterioration of the wound situation. With intraluminal treatment in the esophagus in case of an esophageal perforation, the loss of the negative pressure can allow swallowed tough saliva secretions to get between the esophageal wall and the fluid collection element and lead to clogging of the pores and hence to discontinuation of the therapy. In case of other applications in the small or large intestine, insufficient pressure parameters can cause clogging of the pores by small or large intestine feces.

In endoscopic vacuum therapy, according to the findings of the invention herein, a permanent negative pressure is generated at the wound, avoiding a drop in the negative pressure subject to the therapy. In case of a sometimes inevitable drop of the negative pressure, the vacuum is very rapidly restored by the vacuum system according to the invention. For example, when placing a sponge drainage into the esophagus, as a result of the physiological swallowing action, a drop in the vacuum can occur both because of the swallowing of saliva, food, air and gas and because of intestinal peristalsis. The same applies to the application of vacuum therapy on the small intestine, large intestine or stomach or in the entire intestinal system.

In contrast to the vacuum treatment of external wounds, in endoscopic vacuum therapy there is no possibility of visual and palpatory monitoring to determine whether the negative pressure is being applied to the fluid collection element and the internal wound because the fluid collection element beneath the surface of the body can no longer be seen after placement. The therapy come to a standstill or the therapy is ineffective if the exertion of suction on the wound is built up too slowly or is interrupted. An interruption of suction may also occur as a result of clogging, kinking or collapse of the fluid communication element or fluid collection element. Clogging of the open-pore structure as a result of the tissue aspiration may also occur in case of too high a vacuum, and with an elastic fluid collection element, a complete collapse of the fluid communication element may occur upon elimination of the suction effect on the tissue. It is only by the characteristics of the vacuum system according to the invention, specified in the invention, that an effective internal vacuum therapy is made possible. The endoscopic vacuum therapy made possible by the invention involves a negative pressure therapy for internal wounds carried out using flexible endoscopes subject to endoscopic vision and using endoscopic techniques, vacuum drainage devices being intracorporeally introduced into hollow spaces in cavities (intracavitary), intestinal lumens (intraluminal) via natural or artificial body orifices. Hence, the vacuum system according to the invention enables endoscopic vacuum therapy of internal wounds, some of which, if untreated, are associated with a high mortality rate or often require complex surgical treatment.

In contrast to the vacuum treatment of external wounds, in the endoscopic intraluminal, intracavitary and intracorporeal vacuum therapy using the vacuum system of the invention herein, it is only by mutual attachment of wound and soft part tissue around the fluid collection element, which, in surgical use, conveying fluids, is connected to the vacuum pump of the vacuum system according to the invention, after application of the negative pressure, that internal wound sealing is achieved. Only as a result of this tissue sealing will the hermetically sealed space be created that allows the lasting generation and maintenance of a vacuum. The hollow space, in which the fluid collection element is located, is evacuated and, as a result of the vacuum, collapses above the fluid collection element. If the fluid collection element is elastically designed, it, too, collapses as a result of the vacuum. Using the vacuum pump of the vacuum system according to the invention, a permanent suction effect is generated on the wound, which is closed thereby. The fixing of the fluid collection element at the placement site is not achieved until the adjacent tissue and/or the intestinal mucosa becomes attached by suction.

In contrast to the vacuum therapy on external wounds, in which sealing is performed using an occlusive film dressing, sealing in endoscopic vacuum therapy, which can only take place because of the vacuum as a result of the abutting tissues, is less stable. Sealing and, therefore, the fixing of the fluid collection medium is exclusively caused by the fact that, as a result of the vacuum, the fluid collection element attaches itself to the tissue by suction similar to a suction cup and the vacuum is maintained permanently and constantly. The invention is, therefore, based on the finding that, for successful implementation of endoscopic vacuum therapy, a vacuum system must meet the requirements specified by, set on and monitored by the pressure regulating unit.

For build-up of a vacuum for carrying out any vacuum endoscopy, in the vacuum system according to the invention, a vacuum pump is provided, the suction capacity of which is controllable and which is designed to generate, within a short defined evacuating period of between 0.5 and 5 seconds, a specified negative pressure at the application site of the fluid collection element and then to maintain it at a constant value.

The invention is further based on the finding that an additional parameter, namely the volume of the wound cavity to be evacuated or the intestinal lumen, is negligible. Conversely, it is noteworthy that with constant volumes to be evacuated (fluid communication element, fluid collection element, secretion container), the rate of the suction build-up in the presently relevant range of values of the negative pressure, with the volume of the secretion container being known, can practically be controlled via the suction capacity of the vacuum pump alone (liters/minute). Since the secretion collection container can fill up with secretions, the dead volume is then reduced. This can also be measured, and the suction capacity can be automatically adjusted to the filling state of the container.

Hereinafter, exemplary embodiments of the vacuum system according to the invention are described.

In the specification herein, negative pressure values are provided relative to ambient pressure. In the literature, these negative pressure values are often also provided with the negative sign. It will be omitted herein, and only the amount of negative pressure will be indicated. As is customary in professional circles, the negative pressure values will be given in units of mm Hg, and for the purpose of conversion to SI units, a ratio of 1 mm Hg=133.322368421 Pa can be used. The term vacuum is used in the specification herein as a synonym for the term negative pressure.

The inventor has found that, in practice, negative pressures of an amount of less than 60 mm Hg and an amount greater than 500 mm Hg are not be required and that insofar, the performance of the vacuum pump can be limited in favor of a design of limited performance but instead lighter and preferably portable by the patient.

As a vacuum pump, in various exemplary embodiments, a displacement pump, such as a rotary piston pump, a rotary vane pump, a trochoid pump, a scroll pump, a piston pump, a helical pump, a rotary piston pump, a roller pump or a membrane pump is provided.

The vacuum pump to be provided in the vacuum system according to the invention shall, within the context of the specification herein, be understood to include combinations of at least two pumps or multi-stage pump systems. In one embodiment, the vacuum pump is for example equipped with two pumping stages. In this arrangement, the vacuum pump is preferably equipped with a pump combination. Preferably, the vacuum is generated via a prevacuum using a booster pump, A parameter of the vacuum system according to the invention that is important for successful treatment is the period of time required for evacuation to the required negative pressure of the volume involved in each case in the sections of the hollow spaces to be treated. In preferred embodiments, the maximum suction capacity of the vacuum pump is designed in such a way that, taking into consideration the dead volumes that occur in practice, the pressure value of the vacuum specified according to the invention is reached within a short period of about half a second.

In other embodiments, the maximum possible evacuation period lasts up to a few seconds, in particular up to a maximum of 2 seconds, in order to reach a defined continuous vacuum. Accordingly, in the mentioned embodiments of the vacuum system, the pressure regulating unit is designed to control the vacuum pump in operation for achieving the vacuum within a range of values of the evacuation period that comprises the stated minimum and maximum values of the evacuation period. The negative pressure is maintained constant after the evacuation period.

Advantageous embodiments of the vacuum system additionally have, connected to the pressure regulating unit, a user input unit which is designed to accept a user input of the evacuation period and/or a negative pressure value and to transmit it to the pressure regulating unit. The pressure regulating unit is designed to determine the control signal concerned, figuring in the current user input, and transmit it to the control input of the vacuum pump.

In a variant, for exceptional situations, additionally, the operation of the vacuum system with an evacuation period of more than 5 seconds is possible via an appropriate user input on the user input unit (or on a hand piece or foot pedal, connected to the user input unit, to be operated by the physician.) This can also be useful if, using a single pump system, the present focused vacuum endoscopy as well as a vacuum treatment of external wounds is to be feasible.

A certain temporary increase of the vacuum over the value intended for therapy may be indicated initially, hence at the beginning of therapy, for a short period of time, in order to assure a secure attachment of a drainage device at the therapy location. Even after placement, initially a higher negative pressure is temporarily advantageous so that the fluid collection medium can be suctioned into place in such a way that it cannot accidentally be dislodged by an endoscope introduced into the body during this initial phase. But if so, in comparison to the total duration of therapy, this involves a relatively short initial period of time, for instance, 15 minutes, while the duration of therapy can typically extend over several days.

After successful placement, the patient will typically carry the vacuum system with him. Preferably, the user input will have a lockable mode switch that allows adjustment by the user of either a therapy mode or an endoscopy mode, the pressure regulating unit being designed to output only the second or third control signal but not the first control signal in the therapy mode and the predefined negative pressure value interval in the therapy mode extending over negative pressure values with respect to a surrounding pressure between a minimum negative pressure of 60 mm Hg and a maximum negative pressure of 250 mm Hg. The locking of the mode switch is preferably only possible using a key, wherein key can also mean a code.

According to a finding of the inventor that led to an enhancement of the invention, the success of the therapy is further improved if the evacuation period and the negative pressure are adaptable according to an examination or therapy to be carried out in each case. In the treatment of esophageal injuries, for instance, the pathophysiological intrathoracic negative pressure and the pressure fluctuations caused by respiratory motion are directed against the suction effect of the vacuum pump. This physiological negative pressure must be cancelled out or counteracted by a very short vacuum pump evacuation period in the direction of the suction of the pump. In contrast to the therapy on the esophagus, in case of a negative pressure treatment following anastomotic insufficiencies at the rectum, with an Anus praeter upstream and only very slight secretion, a longer evacuation period within the limits of the invention of up to 5 seconds may also be therapeutically successful.

After the vacuum has been built up to the defined pressure, this pressure must be maintained constant. A drop in the negative pressure is immediately recordable by the vacuum system according to the invention using the sensor and removable again within the evacuation period, advantageously, as a result of the usually remaining residual vacuum, a period of time even much shorter than the evacuation period being needed for restoring the nominal value of the vacuum. In this way, a constant negative pressure can be assured at the therapy location. Preferably, the pressure regulating unit and the vacuum pump are, therefore, designed for being able to build up the defined negative pressure as a function of incoming test signals at a frequency of at least 30 vacuum buildups/minute. This proves to be beneficial for carrying out an endoscopic vacuum sponge therapy on the upper gastrointestinal tract. In further embodiments, using the vacuum system, up to 60, more preferably 120 vacuum buildups/minute can be carried out.

In a preferred embodiment moreover, the evacuation period is adjustable by user input via the pressure regulating unit. For this purpose, the vacuum system additionally has, connected to the pressure regulating unit, a user input unit which is designed to accept a user input of the evacuation period and to transmit it to the pressure regulating unit. The pressure regulating unit is adapted to control the vacuum pump as a function of the user input, in order to generate the negative pressure in the specified evacuation period.

In an additional embodiment, the pressure regulating unit is designed to support a selection between the following predefined therapy settings via the user input unit by appropriate predefined control parameters:

a) a maximum evacuation period of 2 seconds;

b) an evacuation period between 0.5 and 5 seconds more closely definable by further user input;

c) an adjustable evacuation period of 2-5 seconds.

For example, for the treatment of an esophageal leakage, a negative pressure between 80 and 150 mm Hg (10665 to 20000 Pa) and selecting a maximum evacuation period of 2 seconds is advantageous.

In many applications, the value of the negative pressure to be selected also depends on a contact surface of a fluid collection medium with the surrounding tissue. With a large contact area, compared to a small contact area, for fixing the fluid collection medium a lesser negative pressure may be required.

The user input unit is, therefore, preferably additionally designed to receive an additional input of an identification of a type of fluid collection element. In this embodiment, the pressure regulating unit is designed to determine, based on prestored therapy data, values assigned to the input type of the fluid collection element of the vacuum and/or the evacuation period, and to control the vacuum pump during operation in accordance with these determined values.

In clinical applications, a continuous lasting negative pressure has essentially proven to be of value. But a variant provides for the pressure regulating unit to be designed to control the vacuum pump so as to apply the negative pressure fluctuating between at least two negative pressure values, for example between about 100 mm Hg and about 150 mm Hg. By applying a fluctuating negative pressure, the granulation stimulation of the wound can be increased. However, at no time must a suction interruption lasting longer than a few seconds take place.

The pressure regulating unit is designed to monitor negative pressure values during a negative pressure application and an examination carried out using negative pressure. Sensors are connectable by either electrical, i.e. wired, or wireless communication to the pressure regulating unit of the vacuum system, so that preset negative pressure values of the vacuum pump to be generated can be monitored and adjusted by the pressure regulating unit. In this way, as a result of the pressure detection, monitoring and control of the pump suction can be performed directly on a fluid collection element by sensors. This prevents a therapy standstill from occurring, for example in case of clogging of the fluid collection medium or the fluid communication element. This is particularly important in the treatment of esophageal injuries, because otherwise an inflammation of the chest cavity occurs, which entails a tedious treatment and often leads to death.

By evaluating the test signals arriving from the pressure sensors, comparing them to a nominal value in each case, the pressure regulating unit preferably also captures the evacuation period actually required.

The vacuum system is preferably provided with a vacuum drainage arrangement which is connected upstream of the vacuum pump on the negative pressure side. With the same suction capacity of the vacuum pump, rapid suction build-up is possible using a smaller secretion collection container rather than a large collection container. The pressure regulating unit is, therefore, preferably designed to accept a user input of a collection container volume via the user input unit and to adjust the pump capacity additionally dependent on the entered volume. In doing so, the pressure regulating unit controls the pump capacity not only, as explained above, in accordance with the evacuation period desired by the user, but also additionally takes into account for this purpose the volume of the secretion collection container.

The pressure regulating unit is designed to figure in a secretion collection container volume as part of the dead volume. Depending on the application, different secretion collection container volumes may be required so that the pressure regulating unit must be able to use appropriately different dead volume values. They may, for instance, be saved in a memory of the pressure regulating unit and selected by user input. To prevent input errors, alternatively coding, affixed to the secretion collection container per se and readable by the pressure regulating unit, may be captured, from which the applicable dead volume value can be derived. With a small collection container volume, the suction capacity of the pump is set lower, with a larger volume, the suction capacity is set accordingly higher.

The secretion collection container is designed to accept and/or discharge secretions and gas that occurs during operation and is aspirated by the vacuum pump. Preferably, the pump is additionally equipped with a negative pressure-resistant presecretion collection container, which is connected, in the direction of suction, upstream from the application site on the patient toward the vacuum pump and is connected to the secretion collection container conveying fluid. The pressure regulating unit is then designed appropriately to figure in a secretion collection container volume as an additional part of the dead volume.

In this variant, collected secretions can be conveyed from the presecretion collection container to the secretion collection container. Preferably, the presecretion collection container and the secretion collection container are connected to each other across a valve. As an addition or an alternative to the valve, the presecretion collection container and the secretion collection container are connectable to each other via an interposable filter. Preferably, these collection containers and their connection to the vacuum are designed exchangeable.

These embodiments provide for a suction build-up via the dead volume of the secretion collection container. If the suction build-up of the vacuum pump takes place via a secretion collection container, its dead volume, together with the suction capacity of the pump (L/min), substantially determines the rate of suction build-up. The suction capacity of the vacuum pump is, therefore, preferably designed to evacuate additionally the dead volume which is formed by the secretion collection container and the presecretion collection container within the evacuation period.

The secretion collection container is connectable, via preferably negative pressure-resistant fluid communication elements, in particular drainage hoses, to a fluid collection element so that the negative pressure at the fluid collection element can be built up via the secretion collection container. The pressure regulating unit is designed to figure in, as an additional portion of the dead volume, an additional volume, which forms at least one negative pressure-resistant fluid communication element, in particular a drainage hose, which is distally connectable to a fluid collection element and proximally to the secretion collection container or the presecretion collection container. With constant evacuation volumes on fluid communication elements, fluid collection elements and secretion collection containers, in one embodiment, the evacuation period can be adjusted on the pressure regulating unit via an adjustment of a suction capacity of the vacuum pump. In this arrangement, the pressure regulating unit of the vacuum pump receives, in addition to the user input, as an additional input for adjustment via the test signal input, measured values from a negative pressure sensor, which is located by the hollow space to be evacuated. Details concerning the embodiment and placement of the sensor are discussed below.

If a presecretion collection container used, in these embodiments it is preferably connected to the vacuum pump in such a way that it can be subjected to a prevacuum. In this embodiment, the vacuum pump has two pump stages and is designed to generate the negative pressure at the examination/treatment site using a first stage of the two pump stages via a prevacuum in the presecretion collection container. It has the comparatively smaller volume of the two collection containers, in order to achieve as short an evacuation period as possible. The presecretion collection container typically has a volume of 50 mL to 300 mL. The secretion collection container, on the other hand, typically has a volume of 100 mL to 1000 mL. But smaller or larger volumes can also be selected, subject to adjustment of the required suction capacity of the vacuum pump.

An additional preferred embodiment provides for a pressure regulating unit, which not only adjusts the capacity of the pump in accordance with the volume of the secretion collection container, but also takes into account a volume of a fluid collection element to be evacuated. Here again, as described above, an additional user input via the user input unit is provided, which is forwarde to the pressure regulating unit, which, in turn, appropriately controls the pump capacity for achieving the evacuation period in each case. In doing so, an evacuation of the secretion collection containers is simultaneously carried out within the evacuation period.

Preferably, the pump capacity is designed in such a way that, within the evacuation period, the dead space volume of the secretion collection container and the fluid collection element is evacuated. Experience hitherto shows that a controllable pump capacity in the range of 1 L/min to 20 L/min is required.

In one embodiment of the vacuum system, the pressure regulating unit is equipped with a monitoring unit, which automatically monitors any excessive rise and/or reduction of the negative pressure, of the duration of the evacuation period as well as a duration of a negative pressure system and adjusts the pump capacity if specified limit values are exceeded. Thus, during operation, in case of any drop of the negative pressure, for example as a result of an insufflation of examination gas, the vacuum can be rapidly restored and, as a result, continuously maintained.

In addition to the control signal input, further switching and control elements, across which an operation of the vacuum pump can be carried out, are preferably provided on the vacuum pump. In particular, the pressure regulating unit and the user input unit can be integrated as a structural unit with the vacuum pump.

For capturing and monitoring the defined negative pressure and the evacuation period, at least one negative pressure sensor on the vacuum pump and/or at least one connection for an external negative pressure sensor is provided. The negative pressure sensor is directly or indirectly connected to a fluid collection medium and/or fluid communication element that is connected to the vacuum pump and is designed to forward its test results as test signals to the pressure regulating unit of the vacuum pump. Preferably, the fluid communication elements are drainage hoses.

Using the vacuum pump, a vacuum can be built up on a single fluid collection element or a plurality thereof. For the case of a plurality of fluid collection elements, the vacuum pump is preferably designed for accomplishing any vacuum generation completely independent from each other. For this purpose, not only a plurality of appropriate connections and drainage units are provided. In addition, the pump capacity of the vacuum pump is adapted to the higher demands of simultaneous negative pressure generation on various fluid collection elements. The pressure regulating unit is designed to output control signals to individually controllable throttle elements which are arranged in each corresponding branch, in order to effect the individually adapted build-up of a vacuum in each case.

In particular, the vacuum pump is designed to generate a vacuum in endoscopic intracavitary and intraluminal vacuum therapy. It is, however, also usable in vacuum sponge therapy on external wounds. It is moreover usable in vacuum endoscopy.

The vacuum system is preferably designed as a portable unit, so that a patient can move as freely as possible and be mobile. In the portable version, the electrical power supply of the pump is assured for example by a battery or battery pack.

It should be noted that in an alternative embodiment, the vacuum pump in treatment rooms may exist in the form of an integrated, centrally controlled vacuum wall suction device, which must be appropriately adjusted in its pumping capacity, in order to supply at least the vacuum required in accordance with the invention within the evacuation period necessary according to the invention. In this way, with an appropriate infrastructure, in a treatment room, the generation of the necessary vacuum can take place even without a separate vacuum pump, hence with the appropriately designed wall suction device replacing the vacuum pump. The pressure regulating unit of the vacuum system according to the invention must be adapted in such an infrastructure, in order to be able to control vacuum pressure control elements, such as throttle elements depending on the given (usually not controllable) pumping capacity of the wall suction device as a function of time, so that the required negative pressures between fluid collection element and wall suction device are reached within the specified period of time. Via connection, filter, switching and valve element, the forwarding of a vacuum to the fluid communication elements can be made possible and the operation via the handle of the endoscope can take place.

Advantageously, the user input unit of the vacuum system comprises an arrangement for manual control of the vacuum pump, by means of which a start signal for starting and a control signal for reduction of the vacuum on the fluid collection element for forwarding to the pressure regulating unit can be generated and output. Preferably, the user input unit is connected to one switching device or a plurality thereof on the handle of the endoscope; alternatively, operation of the pump via foot/hand switch or directly at the pump is also possible.

In order to be able to perform the examination, in particular a vacuum endoscopy, comfortably, it must be possible to build up and release the negative pressure at short intervals during the course of the examination. For this purpose, in preferred embodiments, a switching unit on the endoscope or a foot switch is provided.

In one embodiment, the vacuum system has a plurality of negative pressure-side connections for one drainage hose or a plurality thereof. The pressure regulating unit in this embodiment is designed to control the vacuum pump upon an appropriate user input via the user input unit, optionally aspirating or flushing either unilaterally only one of the connections or alternating two of the connections or simultaneously two connections. In this way, the vacuum on a plurality of fluid collection elements can be controlled simultaneously and independent from each other, which will be explained in more detail below within the framework of the description of the figures.

The vacuum system according to the invention in preferred embodiments forms a technical component of an endoscope arrangement according to the invention having

- such a vacuum system according to the invention or one of its exemplary embodiments described within the framework of the application herein,
- an overtube unit, which, on the negative pressure side, is connected to the vacuum pump of the vacuum system by at least one fluid communication element and has a fluid collection element,
- an endoscope which is inserted or insertable into the overtube unit and is displaceable relative to overtube unit in a direction going from proximal to distal or vice-versa and
- a negative pressure sensor which is connected to the pressure regulating unit of the vacuum system.

Preferably, the endoscope is also connected to the vacuum pump of the vacuum system via a fluid communication element on the negative pressure side and has an additional fluid collection element.

This exemplary embodiment according to the invention in the form of an endoscopy arrangement is based on the finding that in balloon enteroscopy, known in the state of the art, adequate fixing of an endoscope or overtube by clamping the balloon to the intestinal wall is frequently not possible and, as a result, deeper examinations do not succeed. The balloon can easily slip; in particular, sufficient fixation in the case of wide intestinal lumens (stomach/colon) is not possible. If the balloon is excessively inflated, there is a risk of intestinal wall injury and even wall rupture.

The endoscopy arrangement utilizes this finding for embodiment of an endoscopy arrangement for endoscopic intraluminal sponge vacuum therapy, in order to place one fluid collection element or a plurality thereof, for example sponge drainage devices, for example intraluminally, in the intestinal lumen and to anchor them at the placement site using a vacuum according to the parameters specified according to the invention. The sponge drainage devices in this example, with the vacuum applied to the sponge, attach themselves by suction to the intestinal mucosa and are fixed to the placement site by the negative pressure.

Using alternating mutual displacement of an overtube relative to an endoscope introduced into it, it is possible to push an endoscope forward in the intestine. Endoscope and overtube need an anchoring arrangement against the adjacent tissue, such as the intestinal mucosa. In the embodiment of the endoscopy arrangement herein, this anchoring is achieved by the attachment by suction of the sponge drainage device to the intestinal mucosa. For this reason, the treatment or examination method based thereon is also referred to as a vacuum endoscopy.

Endoscopic vacuum therapy is used in the treatment of internal wounds. Their effectiveness was first demonstrated in suture leaks at the rectum, then also in the case of intestinal leakages at other locations, such as esophagus, stomach, small and large intestines. In the case of internal wounds, cavities, abscesses, empyemas, fistulas situated below the skin surface and which are or are made endoscopically accessible via an opening to the outside, endoscopic vacuum therapy can also be used for wound treatment. In endoscopic vacuum therapy, the natural or artificial means of access to hollow organs, gastrointestinal tract and body cavities are used endoscopically. Using the endoscope, sponge drainage devices are introduced internally, intracorporeally, intraluminally and intracavitary. In the intraluminal therapy variant, the sponge body is placed in the intestinal lumen at the defect level. In the intracavitary variant, the sponge body is introduced through the defect into an (extraluminal) wound cavity. Both therapies may also be combined. After the sponge body is positioned, vacuum suction is applied to the led out drainage hose. The wound cavity or the intestinal lumen collapses subject to the suction together with the elastic sponge body. The sponge surface attaches by suction to the wound surface suction cup-like, and, at the same time, it fixes itself at the placement site by suction. Effective wound drainage takes place, at the same time the wound defect is closed. Subject to the lasting drainage effect and vacuum application to the wound surface, the wound cleanses itself, granulation tissue forms and the wound heals as a secondary consequence. An endoscopic exchange of the sponge drainage device is performed at multi-day intervals.

A special form of endoscopic vacuum sponge therapy does not aim at complete closure of a cavity, as explained above, but at maximum secretion discharge. In it, the sponge drainage device is also placed into a hollow organ, e.g. the duodenum (postpyloric vacuum duodenal drain) and subjected to suction. In doing so, the drainage effect is metered in such a way that complete intestinal sealing need not be achieved, but that the fluid collection medium becomes subject to suction to such an extent that optimal fluid conveyance is achieved (in the example of a duodenal placement, of pancreatic and biliary secretions from the intestinal lumen). It is conceivable to use this type of application in other hollow organs or cavities, where maximum secretion drainage is desired.

Using the invention, complete lasting evacuation of the stomach can, for instance, also be achieved. From the invention arise numerous innovative therapy possibilities for the treatment of internal wounds.

Hereinafter, enhancements of the endoscopy arrangement are described.

The vacuum pump is preferably connected to the sponge drainage unit by one fluid communication element or a plurality thereof in the form of drainage hoses and/or in the form of a channel in the endoscope, which may also be arranged, at least partially, in or on the sponge drainage unit. Particularly preferred, the fluid communication element is fluid-conductive and connected, via orifices in its wall, to the fluid collection element. These perforation openings are particularly advantageously located in a section between the proximal or distal end of the hose. The perforation openings are advantageously located in the middle section of the fluid communication element. In one embodiment, the perforation openings are arranged in a plurality of sections between the proximal and the distal end of the hose. The perforation openings preferably have a diameter of 1 mm to 10 mm. Above the perforation openings of the hose wall, the fluid collection medium can be attached from the outside by means of gluing, suture or another means of attachment.

In enhancements, such fluid communication elements are equipped with dual lumen or even multiple channels. Such a fluid communication element is suitable for flushing and aspirating via various channels. At least one of the channels is preferably designed in its diameter in such a way that a wire-like negative pressure sensor can be temporarily or permanently introduced into the fluid communication element.

As a particular advantage, one half of the fluid communication element may have a small lumen and the other half a large lumen. This may be particularly advantageous especially when the drainage device can be placed in such a way that, for example in the presence of an esophagocutaneous fistula, one of the legs of the drainage device discharges percutaneously outward via the cutaneous fistula and the other drainage leg inward orally via the esophagus. The of the fluid communication element leading out can be closed using clips. Via the fluid communication element, particularly a flushing treatment can also be carried out. In particular, in case of placement of the fluid collection element in the middle section and both fluid communication legs leading out, one of the legs can be used for suction, the other one for flushing.

Advantageously, the various diameters of the fluid communication element are continuously tapered and pass from the large lumen to the small lumen diameter without any gradation. This assures atraumatic placement of the drainage device. The perforation openings are located in particular at the distal end of the hose. In order to facilitate the introduction of the sponge system, a wire-like element can be introduced into the fluid communication element.

Advantageously, the fluid collection elements and the fluid communication elements are radiopaque.

Preferably, the fluid communication elements have an inside diameter of 1 mm to 10 mm. Preferably, the fluid collection element, having approximately cylinder shape, has an outside diameter of 5 mm to 30 mm.

Larger fluid collection element diameters are, for instance, advantageously usable, if an intestinal lumen of a large inside diameter (such as the stomach or colon) are to be closed. Smaller diameters of the fluid collection element and the fluid communication element are, for instance, advantageously usable when small lumen fistula ducts are to be closed and drained.

The outside diameter of the fluid communication element and the fluid collection element are, in one embodiment, adapted to the inside diameter of an inner working channel of the endoscope, so that they are displaceable within the inner working channel and their placement can be undertaken via the inner working channel of the endoscope. In particular, this achieves placement of the drainage device through small orifices subject to visualization. Furthermore, minimizing the diameter achieves that, using the endoscopic techniques, the number of regions that are endoscopically reachable is increased and, as a result, can be easily supplied with a vacuum drainage unit.

In an alternative variant, the outside diameters of the fluid communication element and the fluid collection element are adapted to the inside diameter of an outer working channel of the endoscope in such a way that they are displaceable within the outer working channel and their placement can be undertaken via the outer working channel of the endoscope.

In the overtube, in preferred embodiments, one drainage channel or a plurality thereof are integrated as fluid communication medium. They are cylindrical. These drainage channels are negative pressure-resistant, so that they do not collapse subject to the applied vacuum. They are connectable to the vacuum pump by negative pressure-resistant drainage hoses. In particular, the drainage channels have, at their distal end in their walls, an opening or a plurality thereof, which fluid-conductively perforate the overtube outward in such a way that fluids and gases can be drained by suction. At the level of the openings of the drainage elements, the fluid collection element is attachable or attached, for example by gluing, string or clamping.

The fluid collection element that is fluid-conductive and connected to the fluid communication element, can be placed both endoscopically, laparoscopically, thoracoscopically, intraluminally in open surgery, intracavitary, intracorporeally. In an exemplary embodiment, the sponge drainage unit is attached by the distal end of the endoscope and/or the distal end of the overtube unit. For the placement of sponge drainage devices in deeper-situated regions of body, such as the colon, the esophagus or the duodenum, some having very curvy access routes, a drainage hose is proposed, to the end of which the sponge drainage unit in the form of a polyurethane sponge body is sewn. Preferably, the sponge drainage unit has a circular or hollow cylindrical, hence tubular, base body. It consists for example of an open-pore elastic compressible polyurethane sponge body. Preferred is a pore size in the polyurethane foam body from 200 μm to 1000 μm, a pore size of 400 μm to 600 μm being particularly preferred. The sponge can be adapted to the requirements by cutting its length and volume to size.

In a preferred embodiment, the fluid collection medium is an open-pore film. Alternatively, a polyurethane sponge body can be enclosed in such an open-pore film. After adjusting the length of the sponge, the film may, for instance, be pulled over the sponge which is typically achieved by cutting. For this purpose, the open-pore film is preferably designed as a small baggie and can be tied closed using a string. The film may have a structure comprising two film sheets, which are fluid-conductive and connected, via pores, over their entire surface.

As mentioned above, the length and thickness of the fluid collection element can be designed variable. For example, the fluid collection element in various embodiments is between 2 and 10 cm long, but other lengths are also possible depending on the application, as indicated below. In other embodiments, the fluid collection element has an outside diameter of 1.5 cm to 3.0 cm. Here, too, adjustments outside this range of values for certain applications may be expedient. For intracavitary therapy, for instance, the fluid collection element is preferably 0.5 cm to 1.5 cm in diameter and 1 to 4 cm long. For intraluminal therapy, however, the fluid collection element is preferably 1.5 cm to 2.5 cm in diameter and 4 cm to 10 cm long.

Preferably, the central channel in the fluid collection element has a diameter of 0.5 cm to 1.0 cm but other diameters are also possible depending on the application.

The sponge body is graspable using grasping tongs, polyp grabbers or loops and insertable orthograde subject to endoscopic control. Placement may, however, be technically difficult. Visibility is restricted. The internal wound orifices, through which the sponge body is inserted, for instance, in intracavitary therapy, are often small and angled and hard to access. The mobility of the endoscope is restricted by the sponge drainage device. The spaces to be endoscoped are narrow. A blunt-ended sponge drainage device easily snags on the internal wound orifice or the intestinal mucosa. The drainage hose, therefore, preferably ends distally in a tip.

It is particularly advantageous if the tip of the drainage device is designed conically as well as, in particular, soft and atraumatic, in order to avoid injuries of any adjacent tissue. The pointed-end distal end of the drainage hose may project beyond the distal end of the fluid collection element, but it may, instead, end in the sponge body.

A conically converging configuration of the hose end advantageously continues in an imposed sponge body of the sponge drainage unit in such a way that the sponge body continuously abuts the drainage device. This facilitates the drainage placement maneuver.

In one embodiment, the projectile-like tapered tip of the drainage hose is also provided with a central channel in such a way that, as a result, a guidewire can be introduced.

The tip may advantageously be equipped with a transverse channel, through which, for instance, a string can be installed. At the distal end of the drainage hose, at the fluid collection element or in the fluid collection element, advantageously a device is attached that can be grasped using forceps, a hook, a loop or another insertion instrument. In particular, a string or wire loop may be attached. In particular, a grasping bead of metal or plastic may be attached. Alternatively, a metal or plastic eyelet may be attached. Or a string may be attached. The string may for example be 1 cm to 250 cm long.

If an additional external access to the internal wound still exists (for example in the form of a fistula), the string may be led out via the fistula using an endoscopic technique. If the tip is lost during the placement maneuver, the string can be used for recovery. In the presence of an additional outward connection, using the insertion instrument or the reinforced string, the pull-(through) technique can also be used for placement. The exchange maneuvers can be substantially simplified by using the pull-through technique.

The device, which can be grasped using forceps, a hook, a loop or another insertion instrument is particularly designed tension-proof in such a way that the drainage device can be pulled by them through tissue, intestinal lumens, fistulas. The device must be designed flexibly and atraumatically.

It is particularly advantageous if the pointed top-seated attachment is designed in such a way that, after application to the end of the drainage hose, the outside of the hose ends flush with the outside of the pointed top-seated attachment.

If there is no fistula to the wound outward, by a puncture from the outside, an additional connection can be created, across which the string can be taken outside. Furthermore, the string may be used for endoscopic, laparoscopic, thoracoscopic or open surgical rendezvous maneuvers. The intraoperative placement maneuver can thereby be substantially simplified.

For example, the through-pull technique can be used when placing a sponge drainage into the esophagus, when a percutaneous endoscopic gastrostomy to the anterior gastric wall was installed. Through this percutaneous stomach access route, a string can be introduced and taken outside through the mouth using a gastroscope. The string is connected to the tip of the sponge drainage device and then, by pulling by the string, pulled to the placement site in the esophagus. In this way, even bulky and very long sponge bodies can be atraumatically introduced. Intraluminal placement becomes much simpler.

The string is preferably attached to the sponge body or the drainage hose in such a way that it can be removed at any time. This is for example possible when the string is passed through a string loop or an eyelet in the form of a double string or infinite loop that is attached to the end of the drainage hose or sponge body. If the string is to be removed, the infinite loop is severed and pulled.

Preferably, a longitudinal axis of the sponge drainage unit runs substantially parallel to the longitudinal axis of overtube.

Preferably a channel created in the sponge drainage unit (hence, the fluid collection element) encompasses the entire circumference of the overtube, a drainage hose introduced into the sponge drainage unit having openings there in its wall. However, the fluid collection element may alternatively just partially encompass the overtube.

The fluid collection element is advantageously provided with a fluid-conducting outer coating that facilitates sliding with respect to the intestinal mucosa in the absence of any negative pressure. Advantageously, this outer coating is a fluid-conducting film. In vacuum endoscopy, the film coating is advantageously hydrophilic, so that the fluid collection element can slide more easily on the mucosa. It is, however, important to assure that the outer coating can conduct the suction to be applied fluid-conductively and unabated onto the intestinal mucosa, in particular with the largest possible surface, so that the fluid collection element attaches itself by suction and becomes fixed in place. The suction effect of endoscopic therapy can only develop on the wound surface in case of open sponge pores in the interior region of the sponge drainage unit. If the pores are, for instance, clogged by mucus, saliva or tough secretions, no suction effect can develop on the wound. Particularly in intraluminal treatment of the esophagus, the sponge body may become partially or completely clogged by swallowed viscous saliva. In case of partial clogging, the sponge body does not become attached by suction to the tissue across its entire surface but only partially via the open pores. If the pores become clogged with secretions, the sponge at these points cannot become attached by suction. It will be observed that, between clogged sponge surface and esophageal mucosa, saliva and secretions may drain even into the stomach, while during this process the sponge body is simultaneously still attached by suction to the mucosa via the pores that remain open.

The airtight delimitation required for vacuum build-up consists, on the one hand, in contact with the suction-attached tissue surface, on the other hand, in the surface sealing by clogging mucus or tough secretions. Under these conditions, an effective vacuum suction may continue to exist on the circumscribed mucosa or wound surface. However, if the pores of the sponge body are completely clogged by tough secretions, no suction effect can develop at the wound bed; the vacuum then exists only in the fluid-conducting system. Therapy comes to a standstill or there may even be worsening of the wound condition.

One embodiment of the endoscopy arrangement, therefore, provides for the sponge body to have, on its outer surface, recesses for receiving a sensor, which can be inserted between intestinal wall and sponge body during the operation of the endoscopy arrangement. Such an additional sensor can be utilized for enteral feeding, stomach relief or flushing. A vacuum can be applied to the sponge body while an additional sensor is simultaneously in place. At the points, at which the additional sensor comes to be in place between sponge and intestinal wall, the sponge develops no direct suction effect on the intestinal wall. Neither are the typical sponge- and suction-caused mucosa and wound changes observed here. In case of direct sponge contact with the mucosa, the mucosa fits itself to the sponge surface so that the mucosa adheres nub-like in the pores of the sponge.

In a different embodiment, sections of the fluid collection element are provided with a surface seal for closure of the open pores. The surface seal may be provided by an elastic adhesive, which can be applied to the surface of the sponge in liquid form or as a spray and cures here elastically.

This assures that the sealed surface of the sponge does not exert any suction effect on the mucosa or wound surface abutting here. The sponge body then becomes attached by suction to the tissue surface across the surface of its open pores only. As result of the sealing, an effective local vacuum can continue to be built up. Appropriately targeted placement of the sponge body assures that the vacuum suction and the suction cup-like attachment of the sponge body by suction is undertaken only in a circumscribed tissue region. In this way, any potential tissue injury by the vacuum suction that does not require treatment is avoided. At the same time, the local vacuum suction can be applied at the location in need of therapy.

With a cylindrical sponge body to be inserted into an esophagus, sealing may advantageously be undertaken on a third or half of the surface over the entire length of the sponge body. Depending on the configuration of the sponge body, different patterns for surface sealing are possible. Placing a partially sealed sponge body into the esophagus can achieve that, between the sealed sponge surface and the adjacent mucosa that is not exposed to the vacuum suction, saliva secretions, fluids can even empty into the stomach physiologically along the esophagus. Saliva retention is reduced, a liquid diet can be made possible. Along the seal, a feeding tube for enteral feeding can also be installed.

Alternatively, the surface sealing can be produced using elastic films glued onto the sponge. Advantageously, these films may be longitudinally profiled so that secretions can better drain along the film by capillary action in a distal direction. Surface sealing may also be implemented using longitudinally halved elastic tubes which are attached to the sponge body by their convex side by gluing. With the mucosa abutting the concave side, a tubular tunnel is produced, through which secretions can drain, without being aspirated by the sponge body. The stated different types of surface sealing may be combined with each other.

Furthermore, in one embodiment, for passing through secretions, at least one tubular tube is integrated in the sponge body. This allows a flow of secretions (e.g. flow of saliva to the stomach) through the sponge body subject to vacuum suction. Premature clogging of the sponge pores by viscous secretions is prevented or delayed, so that the vacuum can develop its effect at the wound bed or the mucosa better and for a longer period of time. At the same time, in a treatment at the esophagus, saliva retention can be prevented and enteral nutrition made possible in intraluminal vacuum therapy. Numerous new therapeutic possibilities arise from the use of this embodiment.

As a particular advantage, the fluid collection element should be provided with an additional complete channel in the longitudinal direction. Through this channel, another sensor can be introduced. It may be particularly advantageous to introduce a tubular tube, which passes through the entire length of the collection element and projects beyond it by the ends. In a different embodiment, the tube has the same length as the fluid collection element, typically a sponge body. It is not fluid-conductive and not connected to the sponge body. Both at the proximal end and the distal end, it may be provided with a tulip-shaped flare. The tube does not collapse when the vacuum is applied, hence is negative pressure resistant. The tube is flexible, without breaking off as a result of kinking. The tube serves as fluid pass-through element for viscous secretions, such as saliva or feces. If these secretions are passed through the sponge body which is subject to vacuum suction, clogging of the sponge pores will be prevented; at the same time, the vacuum application to the wound bed can be maintained. Into the fluid pass-through element, sensors, endoscopic instruments, a guide-wire or an elastic installation and placement rod can also be introduced. In particular, an endoscope can likewise be introduced. In particular, an endoscope can also be used as a guide element for installing a vacuum system with fluid pass-through element. The fact that the endoscope per se can be used as a guide rail for sponge drainage greatly simplifies the maneuver; full endoscopic control and visibility are gained and work steps are saved in the placement of the fluid collection element. The endoscope need not be removed from the body. For this purpose, the endoscope preferably has a diameter between 5 mm and 10 mm.

It has been found to be particularly advantageous that in this type of design, when used in the esophagus, sealing succeeds by particularly intimate, completely circular suction over the entire length of the sponge and that, as a result, very good and reliable coverage of a defect in the esophagus with simultaneous effective drainage at the wound bed is safely possible. Advantageously, at the same time, physiological oral enteral feeding is possible using this embodiment. These are obvious advantages over stenting alone, practiced in the prior art, with self-expanding covered stents, that is to achieve the defect coverage via an expansion force toward the outside.

The tube may be fixed in the sponge body by means of a suture, gluing or in another manner. But no special attachment of the tube within the channel of the fluid collection medium is necessary. On the contrary, if no attachment is carried out, this is especially advantageous. Because, in that case, in a removal maneuver, the tube can be easily removed from it, independent of the sponge body. This is particularly advantageous when the sponge body adheres very firmly to the intestinal wall and is mechanically detached from the wall using an endoscope. With suction applied, the tube is fixed by vacuum suction in the sponge body.

For placement of a vacuum drainage system equipped with such a fluid pass-through element (i.e. the sponge drainage unit, possibly including the overtube,), a pusher may be used. The pusher has a tube, into which an installation and placement rod or an endoscope can also be introduced. The pusher can be moved sliding on these guide elements. Using the pusher, a vacuum drainage system can be moved toward the distal end and can, as a result, be separated from the guide element at the placement site. Like the vacuum drainage system, the pusher is advantageously provided with a longitudinal slot so that, at any time during an examination, they can be placed laterally onto an endoscope or removed.

Advantageously, the distal end and the proximal end of the fluid pass-through element are radially divided and are movable outward hinge-like or wing-like outward with respect to a central tube section of the fluid pass-through element. During movement on the guide element using the pusher, all sections of the fluid pass-through elements abut it. When vacuum suction is applied to the sponge body, the sponge body collapses, contracts and attaches itself to the intestinal wall by suction. At the same time, as a result, the movable ends of the fluid collection element unfold hinge-like and spread open tulip-like. Thereby, additionally, for adhering by suction, the vacuum drainage device becomes anchored at the placement site in a proximal and distal direction. As a result of the tulip-like spreading, saliva and/or secretions can accumulate more easily in the fluid pass-through element and can be passed through the fluid collection element, without being aspirated. This embodiment can be applied particularly advantageously for passing through physiologically accumulating secretions, such as (depending on the application site) saliva, small intestine or large intestine feces or air. Advantageously, compared to complete closure of the intestinal lumen by the vacuum therapy, using this embodiment, in the case of esophagus treatment simultaneous with the vacuum therapy, physiological oral enteral feeding and/or the insertion of feeding or stomach relief sensors is possible. In a treatment involving the colon, this allows feces to be evacuated and the installation of an artificial anus to be avoided.

The ends of the fluid pass-through element can also consist of an elastic film or other surface seals.

As an alternative to using the tube, a channel located in the sponge body can be equipped with a surface seal. This internal surface seal is advantageously made of a longitudinally profiled film, along which secretions are also preferably drained by capillary action, in this way preventing clogging of the sponge body in the intestinal wall contact area. Advantageously the surface seal extends to the proximal end and the distal end of the sponge body.

In one embodiment, the overtube forms a flexible plastic sleeve fitted to the length of the endoscope in the direction from proximal to distal (hereinafter the longitudinal direction), into which the endoscope can be inserted. For vacuum endoscopy, the length will advantageously be selected in such a way that the overtube is approximately 20 cm-80 cm shorter than the endoscope. Over this difference in length, both can be moved back and forth relative to each other in the longitudinal direction. The overtube can be designed with different lengths and diameters. Moreover, it is advantageously designed of a material that allows individually adapting its length to the length of the endoscope, e.g. by cutting if off at the proximal end and/or the distal end. Preferably, the overtube is between 80 cm and 160 cm long. But other lengths are also possible.

The inside diameter of the overtube is preferably only slightly wider than the outside diameter of the endoscope, so that both can be easily moved relative to each other and the overall diameter does not become too large. Preferably, the inside diameter will be 8 mm to 15 mm wide, but other inside diameters are also possible. Preferably, the outside diameter is 10 mm to 25 mm wide, but other outside diameters are also possible.

For better sliding, a lubricant can be used. Preferably, the outer sleeve of the endoscope, the inside and the outside of the overtube are coated using a low-friction, especially additionally hydrophilic material. Advantageously, the proximal end of the overtube has a funnel-shaped enlargement so that an endoscope can be more easily inserted. Advantageously, at the proximal end of the overtube, a valve-like closure is provided, through which insertion of an endoscope is possible, escape of examination gas or secretions is prevented. Advantageously the lumen is tapered at the distal end, so that it abuts the endoscope and, as a result, prevents gradation, which would make pushing the entire unit forward difficult or rather facilitates sliding relative to the endoscope.

In one embodiment, the overtube has, immediately proximal and distal relative to the imposed fluid collection element, an annular lip-like thickening, so that during suction build-up proximally and distally relative to the sponge, at the connection of the lip to the intestinal wall, an intimate connection and thus a better seal is created, which facilitates vacuum build-up at the sponge. Preferably, the annular swells are produced elastic. Preferably, the swells are also slotted like the overtube.

One embodiment of the sponge drainage device has a support sleeve. It is designed in such a way that it can be mounted on top of the overtube and/or the endoscope and removed again. It is particularly designed in such a way that, fluid-conducting, it connects the drainage hose that is situated in the overtube and/or the endoscope and the fluid collection element, hence the sponge of the sponge drainage device. Preferably, the support sleeve is attachable, together with the fluid collection element, on the overtube/the endoscope by means of gluing, adhesive tape, elastic, string or any other fastening option above the suction ports or is already attached accordingly during their production. The use of the overtube/endoscope is, however, optionally possible, depending on the application, with or without fluid collection element.

The overtube and the imposed fluid collection element and the support sleeve are preferably longitudinally slotted over their entire lengths. The longitudinal slot offers the advantage that, at any moment during an endoscopic examination, the overtube can be attached to an endoscope and also removed again. This slot can be closed by gluing, adhesive tape, string, zipper or any other technical means. The closing mechanism is preferably designed in such a way that it can be repeatedly opened and closed.

As a particular preference, the support sleeve has, at its proximal and its distal end, annular swells. An annular lip can also be attached to the proximal and/or distal end of the fluid collection element. Preferably, this lip is attached to the fluid collection element by gluing. Preferably, the annular lip-like swell is created by stable compression and adhesion of the fluid collection medium. The fluid collection element is placeable on the overtube from the side.

In a particular embodiment, the fluid collection element consists of an open-pore thin fluid-conductive film. It has the particular advantage that the diameter of the overtube in the area of the fluid collection element is not substantially increased and that, as a result, the overtube can slide freely. It is, however, important to assure that the open-pore film can be fluid-conductive and forward the suction to be applied unabated, so that the fluid collection element becomes attached by suction and is fixed in place.

In a variant, the overtube is designed so as to receive a plurality of fluid collection elements and drainage hoses in different longitudinal sections. This advantageously assures that the anchoring of the overtube not only takes place at the distal end, but also in other locations along the overtube, too.

In or on the overtube, other working channels may be provided, which extend longitudinally from proximal to distal inside the overtube. Like the overtube, they may also be designed longitudinally slotted for opening and closing. These working channels can be used for flushing, aspirating or inserting instruments.

Overtube as well as endoscope are preferably provided with measurement markings so that, on the one hand, the penetration depth can be determined, but on the other hand, it is possible to measure in how far both are displaced relative to each other.

Vacuum enteroscopy can be carried out using conventional endoscopes. When using a conventional endoscope with a vacuum sponge overtube, only the vacuum anchor is used by the vacuum on the fluid collection medium of the overtube.

The length of the overtube should be selected shorter than that of the endoscope so that mobility relative to the endoscope is possible. Preferably, the endoscope has a length between 120 cm and 220 cm, but other lengths are also possible. Preferably, the endoscope has an outside diameter of 8 cm to 12 mm. But other outside diameters are also possible.

For using the vacuum above a sponge drainage device on the endoscope, specially designed endoscopes are required, which are described below:

Integrated in the endoscope are preferably one or more fluid communication elements. They are preferably designed as negative pressure-resistant plastic channels in a wall of the endoscope, which, as a special preference, are fluid-conductive and perforate the outer sleeve of the endoscope at the distal end of the endoscope with a perforation opening or a plurality thereof and terminate here. These negative pressure-resistant suction channels are connected to the vacuum pump via negative pressure-resistant fluid-conducting connections, so that fluids and gas can be drained by suction. The fluid communication element (the channel) in the endoscope is preferably cylindrical. Preferably, the channel is arranged parallel to a longitudinal axis of the fluid collection element.

Such an endoscope can be used with or without any fluid collection element. With the special endoscope, conventional examinations can be performed, too.

When using a fluid collection element, preferably attached at the level the openings in the fluid communication elements, it is attached by gluing, string, clamping or any alternative fastening possibility. Preferably, the channel of the fluid collection element encompasses the entire circumference of the endoscope at the level of the openings of the fluid communication element. The fluid collection element can also be only partially encompass the endoscope. In a special embodiment, the fluid collection element consists of an open-pore thin fluid-conducting film. It has the special advantage that the diameter of the endoscope in the area of the fluid collection element is not substantially larger and that, as a result, the endoscope can slide unimpeded. It is important to assure that the open-pore coating can direct the suction to be applied and is fluid-conductive, so that the fluid collection element becomes attached by suction and is fixed in place.

Preferably, the longitudinal axis of the fluid collection element substantially coincides with the longitudinal axis of the endoscope or is at least parallel to it. Furthermore, the channel is preferably arranged parallel to an axis of symmetry of the fluid collection element.

Via working channels, endoscopic instruments in the endoscope can be guided to the distal end of the endoscope. Using these instruments, surgical procedures, such as a tissue resection, can be performed under endoscopic vision. The endoscope may for example have one or 2 working channels. As a result of the arrangement within the endoscope, these inner working channels have very small sizes, in order to achieve the smallest possible device diameter for the endoscope.

A preferred embodiment provides for a guide sleeve, which is attached to the endoscope, at its distal end, for instance, and provides an additional external insertion accessory for endoscopic instruments or accessories and/or a flushing and aspiration channel. The sleeve is a dimensionally stable hose or a tubular structure, which does not collapse or break off as a result of kinking. It is flexible, in order to allow following the movements of the endoscope. Another advantage over the internally located guide channels is the fact that an outer guide channel may have a larger diameter. With this guide sleeve, the endoscope is equipped with additional outer working channels, which allows extending the endoscopic treatment options.

At its proximal end, for instance, the guide sleeve may be sealed by a valve, in order to prevent the escape of an examination gas. In varying embodiments, the guide sleeve allows simultaneous attachment of an outer guide channel or a plurality thereof. It may be produced with different diameters.

The fastening accessory on the endoscope may be designed in the form of a sleeve encompassing the endoscope, elastic, adhesive tape or any other type of fastening device. The fastening accessory can be designed in such a way that even removal of the external guide accessory would be possible in the inserted endoscope.

New endscopic treatment options result from the possibility of removability of the guide sleeve. The outer insertion accessory can, for instance, also be used for pushing forward a guidewire for other endoscopic accessories. After placement of the guidewire, the outer working channel can be removed and, for instance, a stent can be introduced via the guidewire subject to optical monitoring of the endoscope that is in place within. The endoscope need not be removed to perform the procedure. In a special embodiment of the vacuum drainage device (in analogy to the inner working channel of the endoscope), it can instead be directly inserted through the lumen of the outer working channel at the placement site.

Advantageously, the lumen of the outer working channel is wider than in the case of an inner working channel, so that, utilizing the advantages of direct endoscopic guidance, a vacuum drainage device may be more bulky.

In a special embodiment, the working channel is distally provided with lateral perforation openings and connected to a fluid collection element and can thus, by itself, be used as a sponge drainage device.

The insertion sleeve may also be produced longitudinally slotted. This allows for an instrument inserted through the sleeve, with the endoscope horizontal, to be laterally released from the sleeve and additional removable instruments could be inserted via the slotted insertion accessory.

Hereinafter, exemplary embodiments are described, which enhance the negative pressure probe. Within the framework of the application herein, it is also referred to as sensor, with the same meaning.

The sensor can be applied in both the vacuum therapy sponge therapy on external visible wounds and on intracorporeal wounds which are not visible from the outside, in order to measure the vacuum that is actually being applied to the wound. The sensor can be inserted both in wound treatment using the fluid collection element.

The sensor one sensors are connected, either wired or wireless, to the pressure regulating unit of the vacuum system, in one variant directly connected to the vacuum pump, so that preset required negative pump pressure values to be generated can be monitored and regulated. Especially in varied embodiments, the sensor can be placed on the polyurethane sponge, be applied abutting the sponge, or between sponge and drainage. But it may instead be arranged within the fluid-conducting system of the drainage hose.

Preferably, a plurality of sensors exist for measuring the generated negative pressure. If multiple sensors exist, they can also perform measurements at different locations and transmit them, for example at the negative pressure side pump output, in the secretion container, at the fluid collection element or in a fluid communication element.

In one embodiment, at least one of the sensors is permanently integrated in the pump system. Alternatively or additionally, at least one of the sensors is designed so as to be retroactively introducible, for example into a fluid communication element.

In this case, the drainage unit can be designed in such a way that the sensor is integrated in the system from the start, but it can instead be retroactively applied to/in the fluid collection element, after the fluid collection element has been inserted into the wound. For this purpose, it can be conducted all the way to the fluid collection element or the wound inside the fluid communication element, or it can be conducted to the wound site separately in a second fluid communication element. It is also possible to equip the fluid communication element with a second lumen for this purpose. In doing so, it is advantageous if the sensor is designed in the form of a wire in such a way that, like an endoscopic control mandarin, it can be easily pushed forward even in a small lumen.

Preferred embodiments according to the invention are described hereinafter with reference to figures.

Additional preferred embodiments according to the invention will be explained hereinafter with reference to the accompanying figures according to their structure and handling.

FIG. 1b is a block diagram with further details of the pressure regulating unit of the vacuum system of FIG. 1a;

FIG. 2 is a partial longitudinal section of the vacuum system of FIG. 1a;

FIG. 21 is an additional longitudinal section of the overtube of FIGS. 18 to 20;

Figure 33:
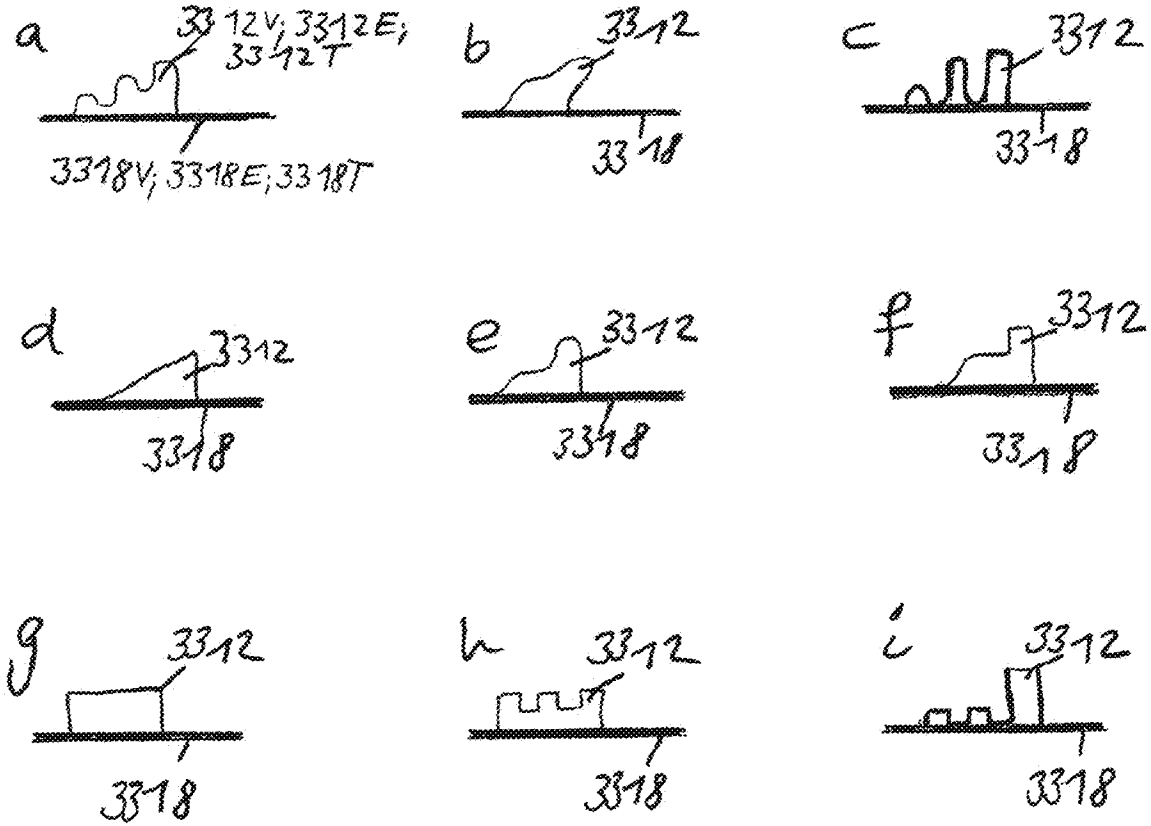
Figure 34:
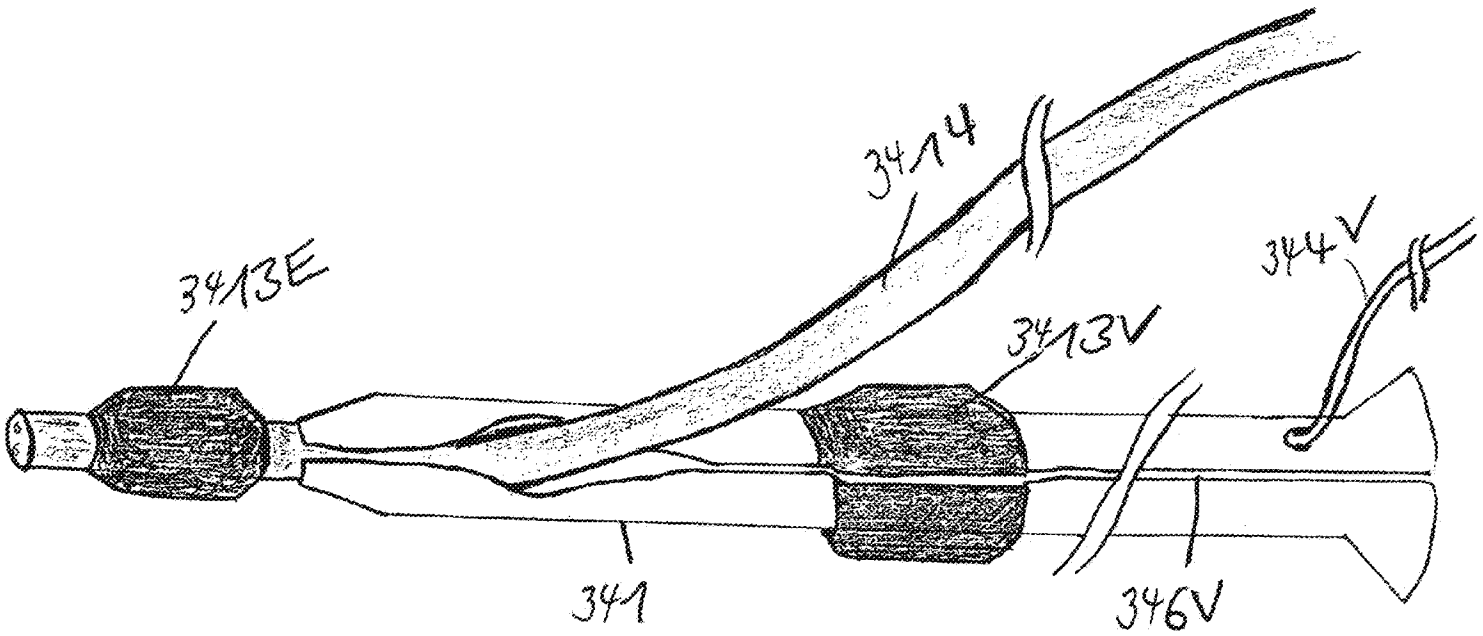
Figure 35:
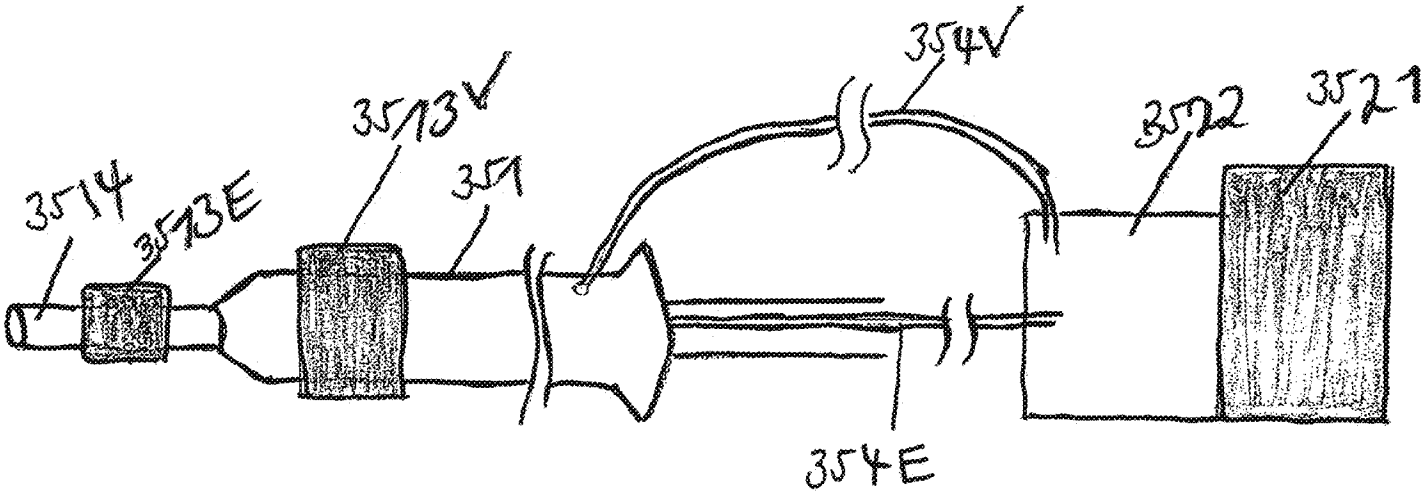
Figure 36:
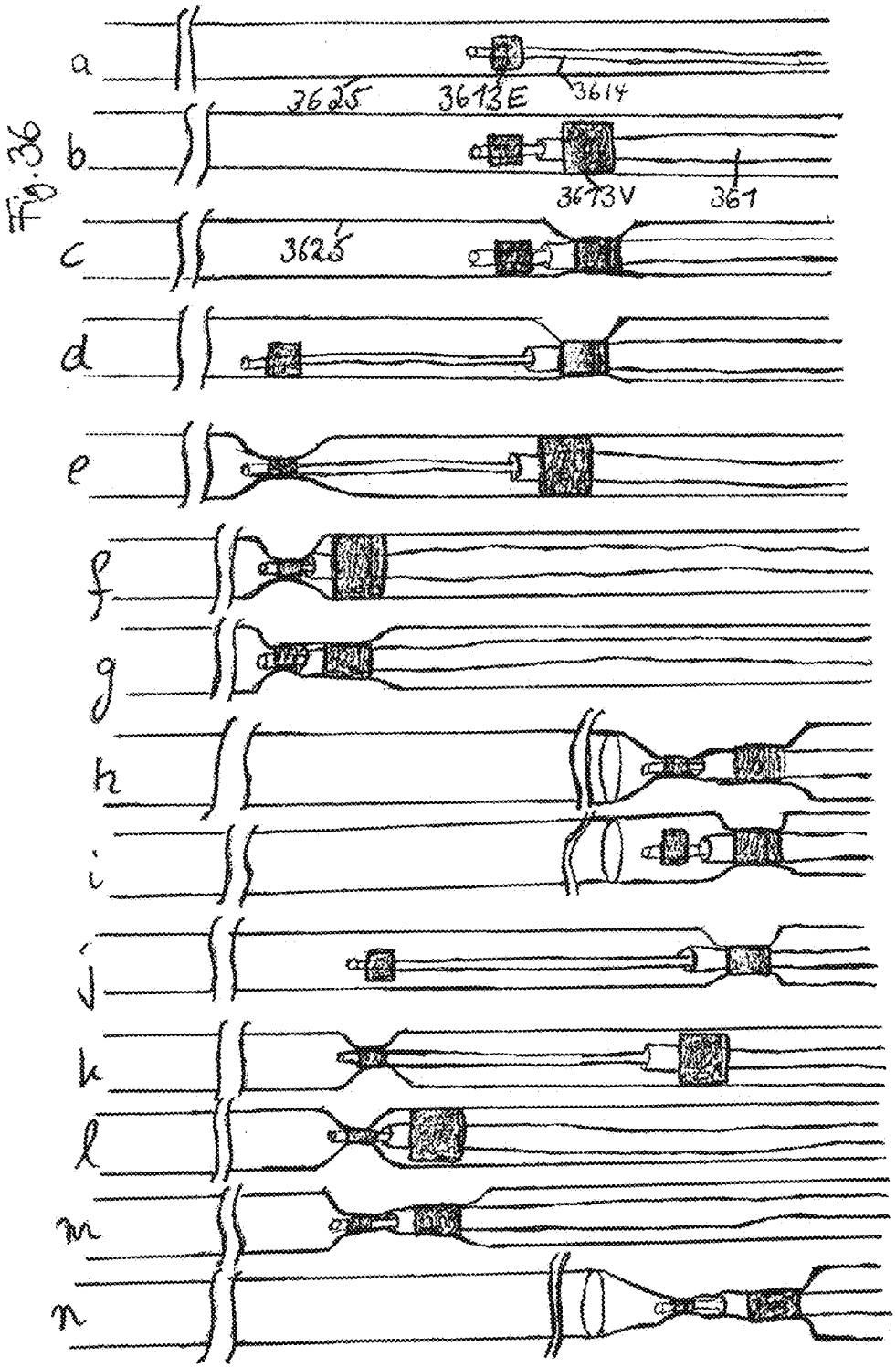
Figure 37:
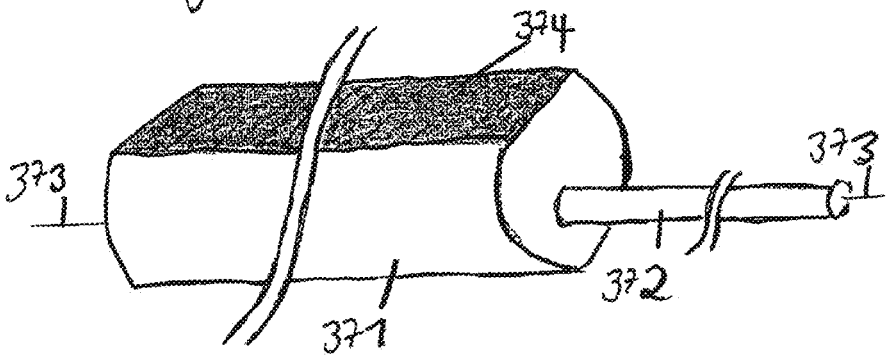
Figure 38:
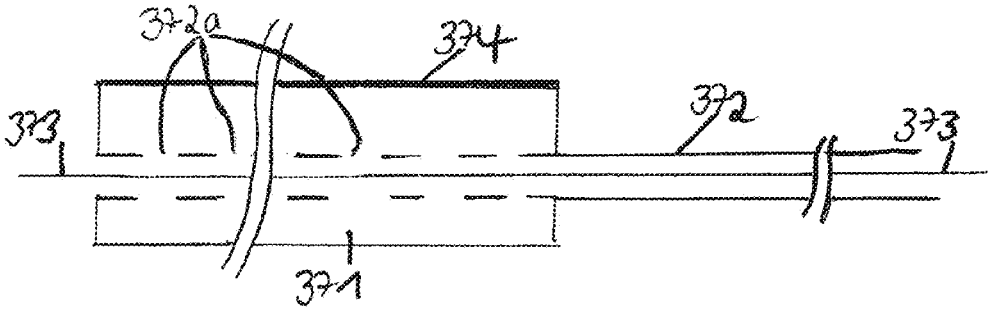
Figure 39:
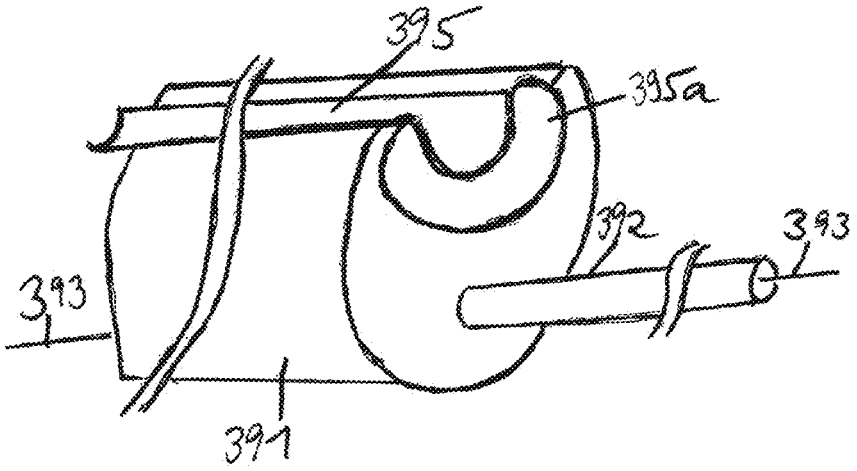
Figure 40:
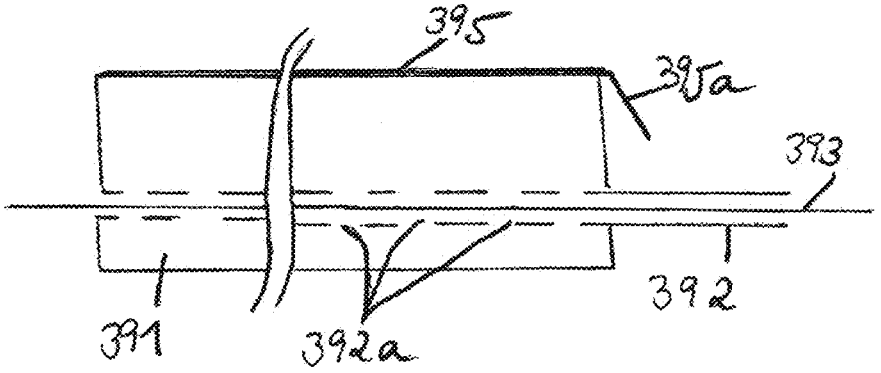
Figure 41:
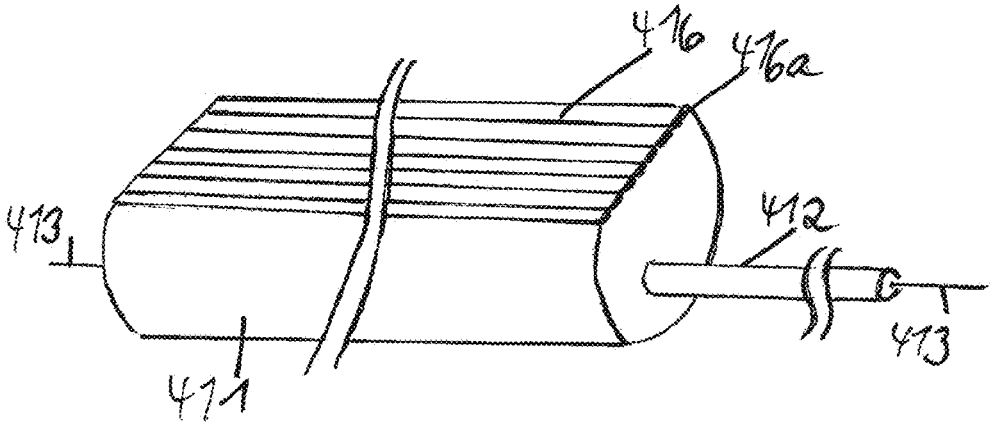
Figure 42:
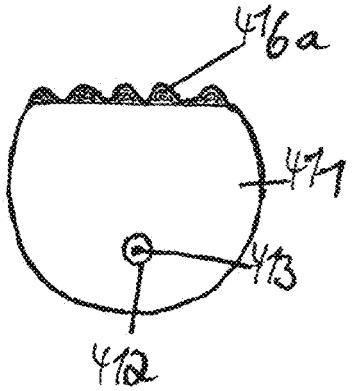
Figure 43:
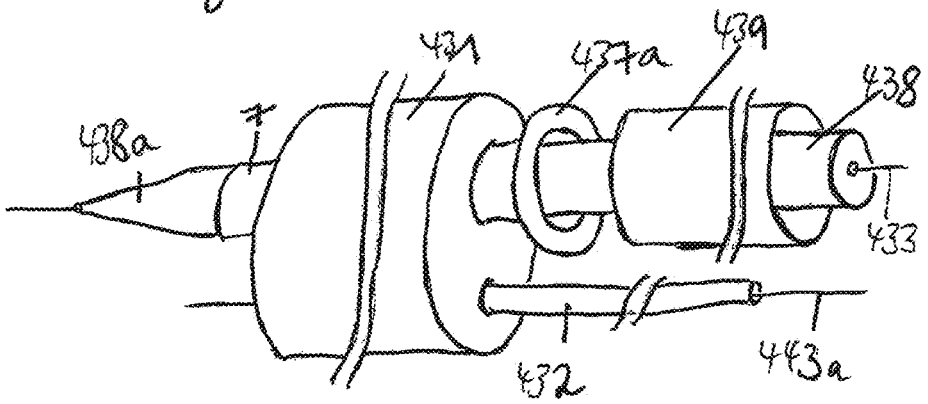
Figure 44:
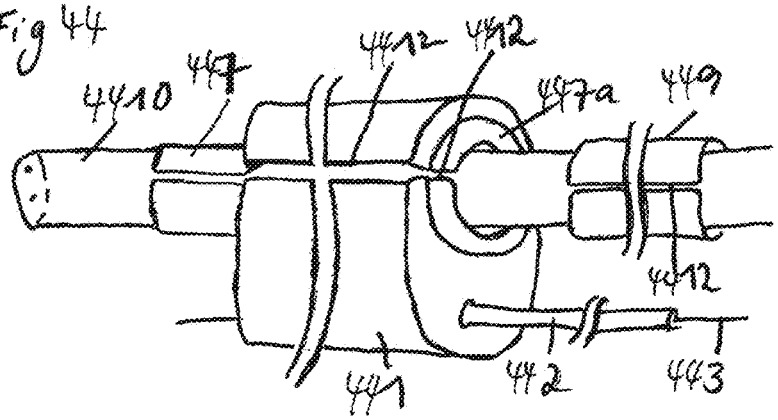
Figure 45:
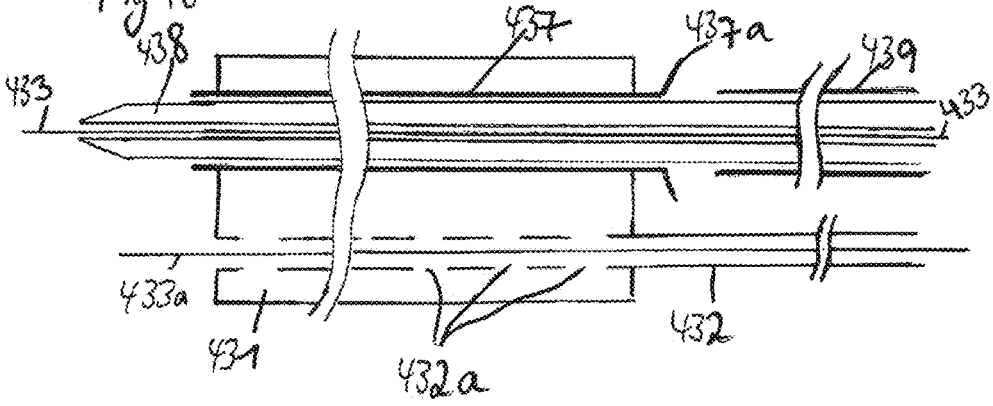
Figure 46:
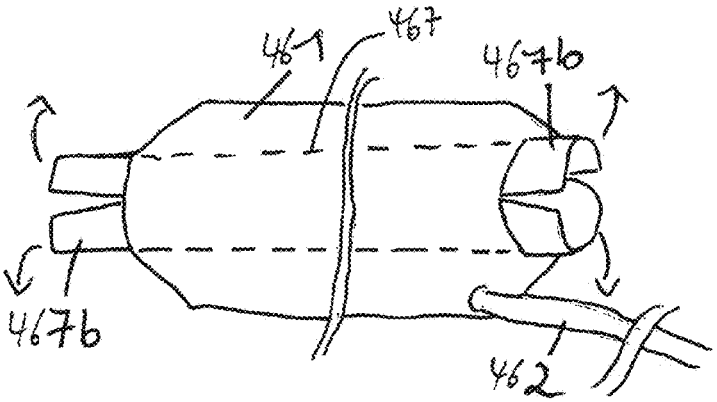
Figure 47:
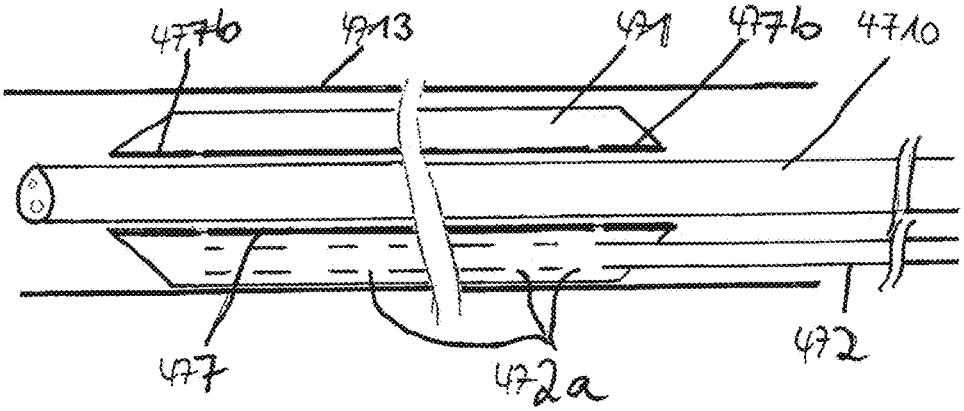
Figure 48:
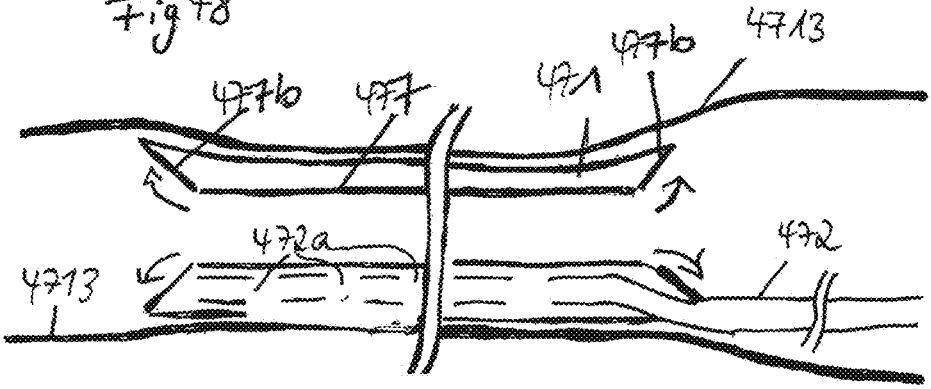
Figure 49:
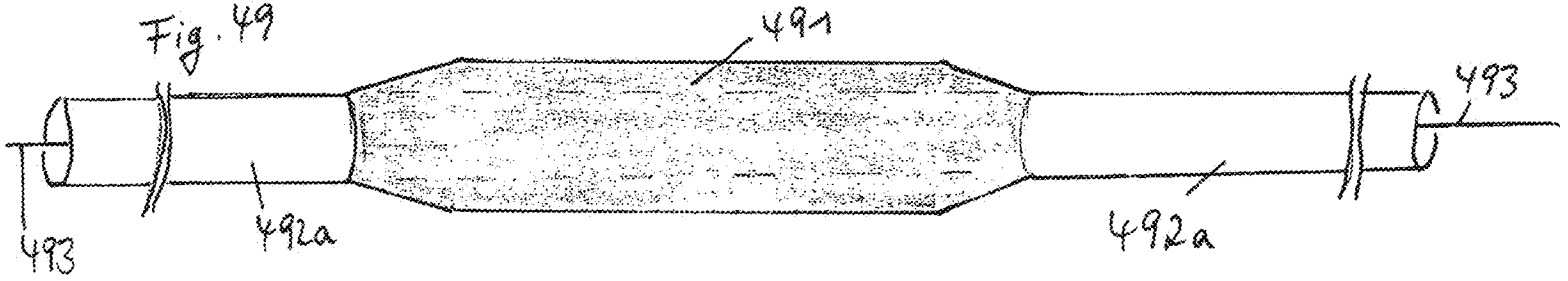
Figure 50:
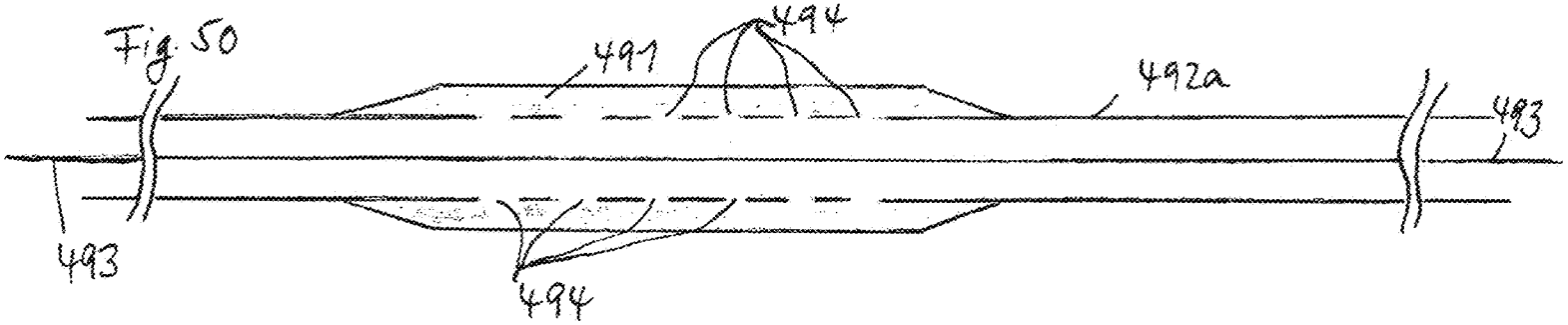
Figure 51:
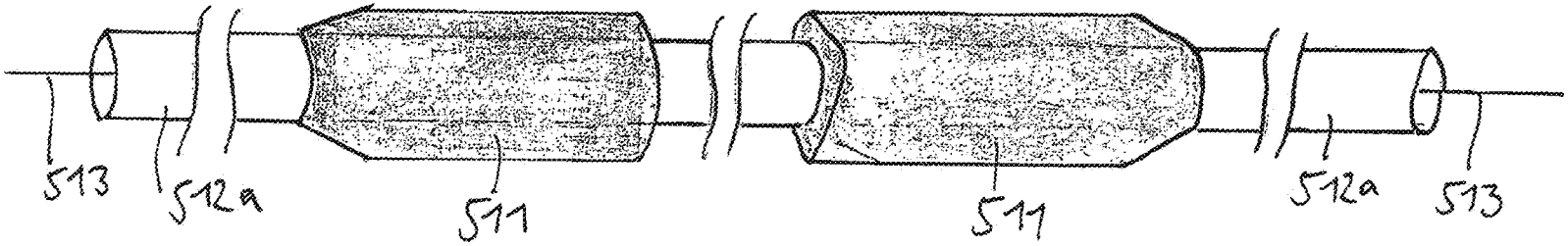
Figure 52:
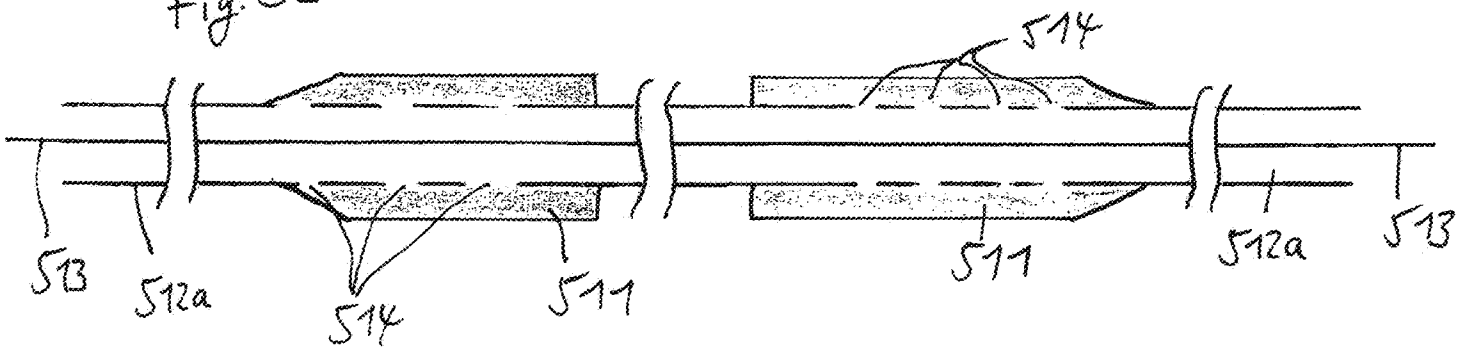
Figure 53:
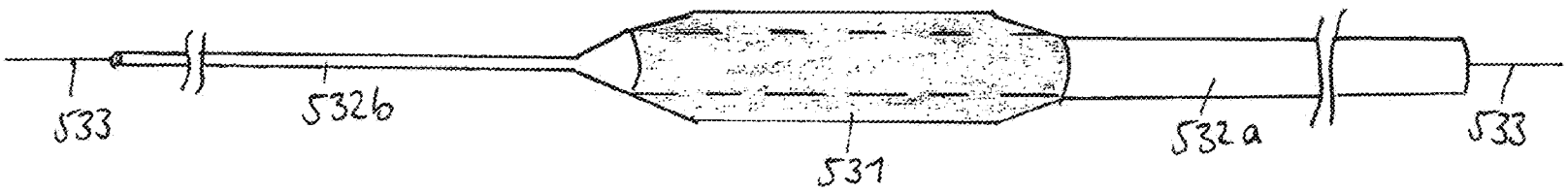
Figure 54:
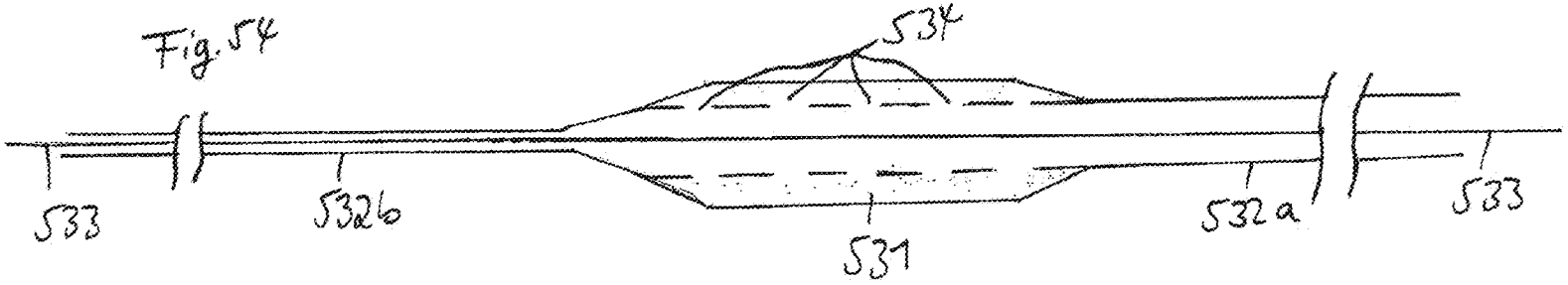
Figure 55:
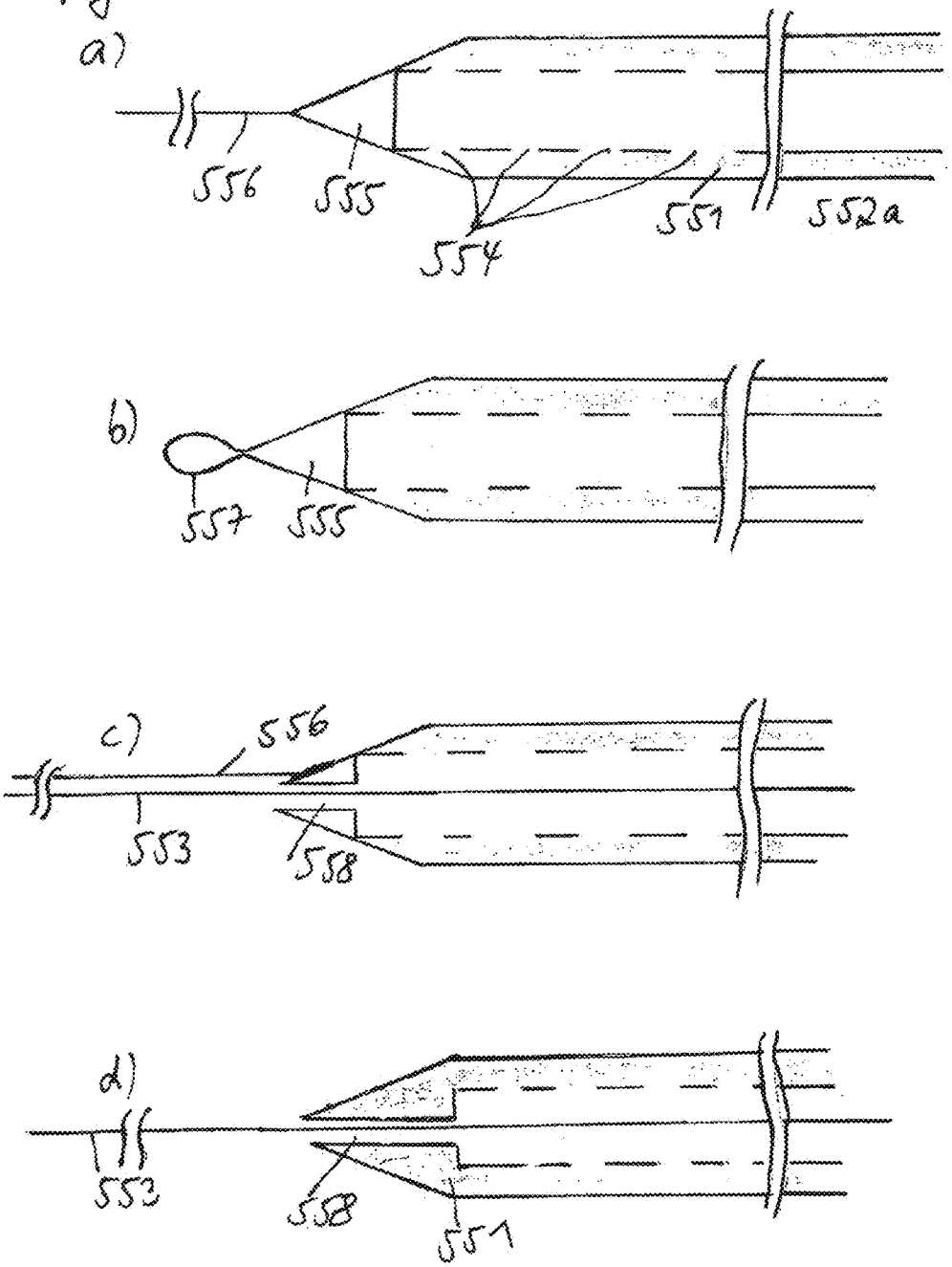

FIGS. 33 a-i show different variants of cross-sectional profiles of lip-like ring closures;

FIG. 34 is a representation for explaining, how a flexible endoscope is inserted or removed via the longitudinal slot of the overtube;

FIG. 35 shows an endoscopy arrangement according to a different exemplary embodiment;

FIGS. 36 a-n show a schematic representation of the examination process of a video endoscopy treatment;

FIG. 37 is a representation of a vacuum drainage with partial surface sealing of the sponge body;

FIG. 38 is a longitudinal section of the fluid collection element of FIG. 37;

FIG. 39 is a representation of a different embodiment of a vacuum drainage;

FIG. 40 is a longitudinal section of the vacuum drainage of FIG. 39;

FIG. 41 is a representation of a vacuum drainage with a profiled surface seal;

FIG. 42 is a cross section of the vacuum drainage of FIG. 41;

FIG. 43 is a representation of a vacuum drainage with a tube attached in a sponge body;

FIG. 44 is a representation of a different embodiment of a vacuum drainage having a tube attached in a sponge body;

FIG. 45 is a longitudinal section of the vacuum drainage of FIG. 43;

FIG. 46 is a representation of an additional embodiment of a vacuum drainage having a drainage hose in a sponge body;

FIG. 47 is a longitudinal section of an additional vacuum drainage having a tube situated in the sponge body;

FIG. 48 is a representation of the vacuum drainage of FIG. 47, in this representation, a negative pressure being applied to the drainage hose;

FIG. 49 is a representation of an additional embodiment of a sponge drainage;

FIG. 50 is a longitudinal section of the sponge drainage of FIG. 49;

FIG. 51 is a representation of an additional embodiment of a sponge drainage;

FIG. 52 is a longitudinal section of the sponge drainage of FIG. 51;

FIG. 53 is a representation of an additional embodiment of a sponge drainage;

FIG. 54 is a longitudinal section of the sponge drainage of FIG. 53;

FIGS. 55 a to h show different variants of a distal end of a sponge drainage, each in a longitudinal section.

Figure 56:
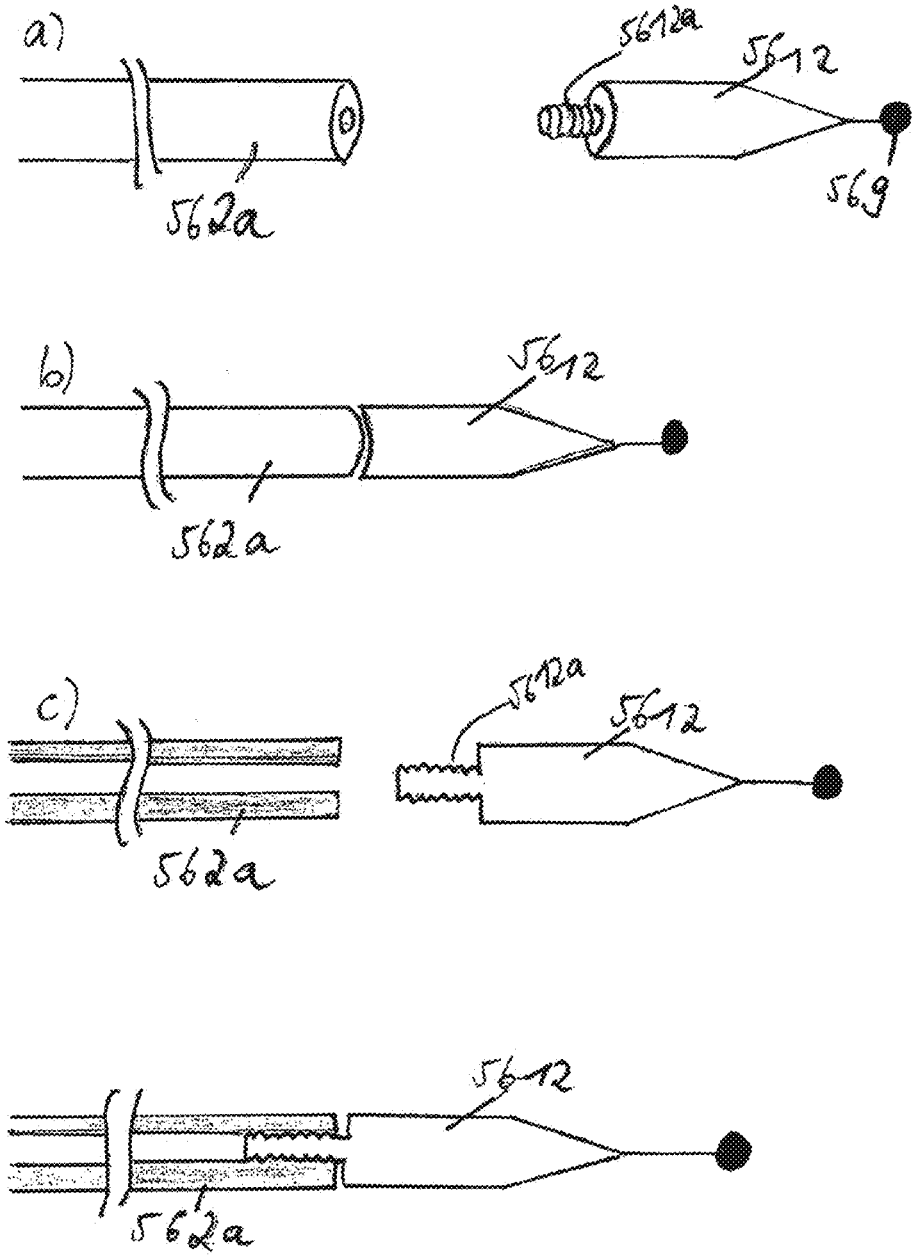
Figure 57:
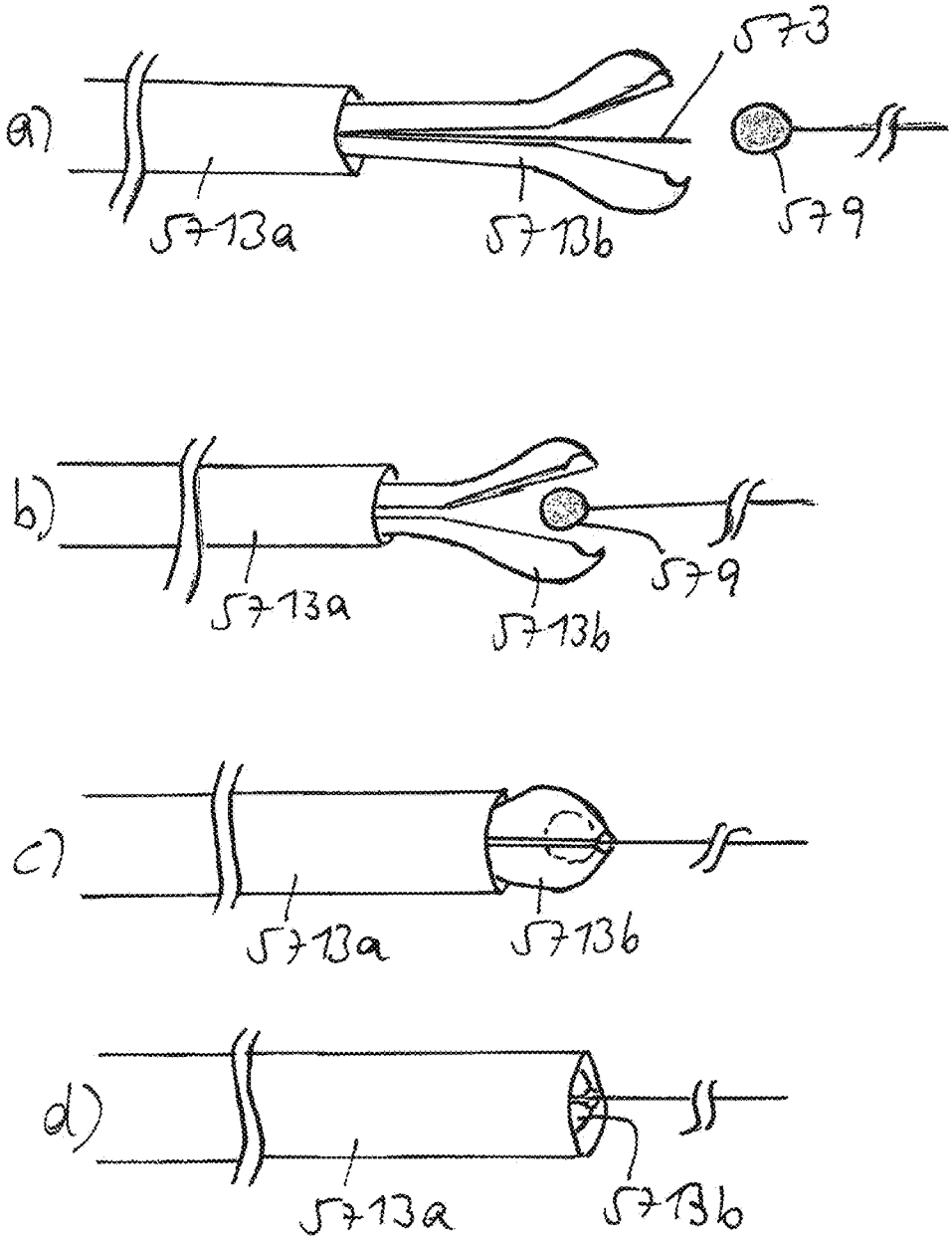
Figure 58:
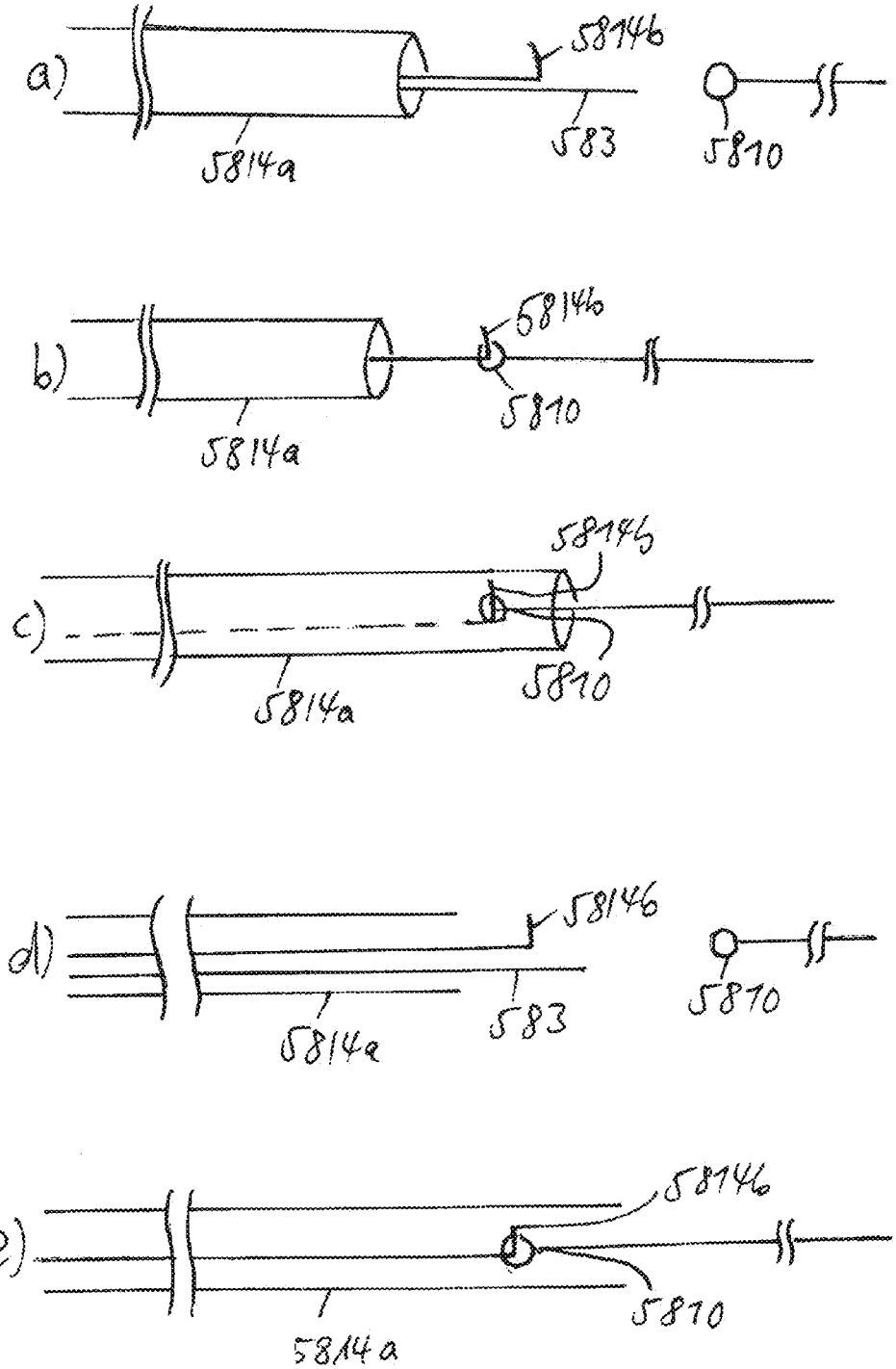
Figure 59:
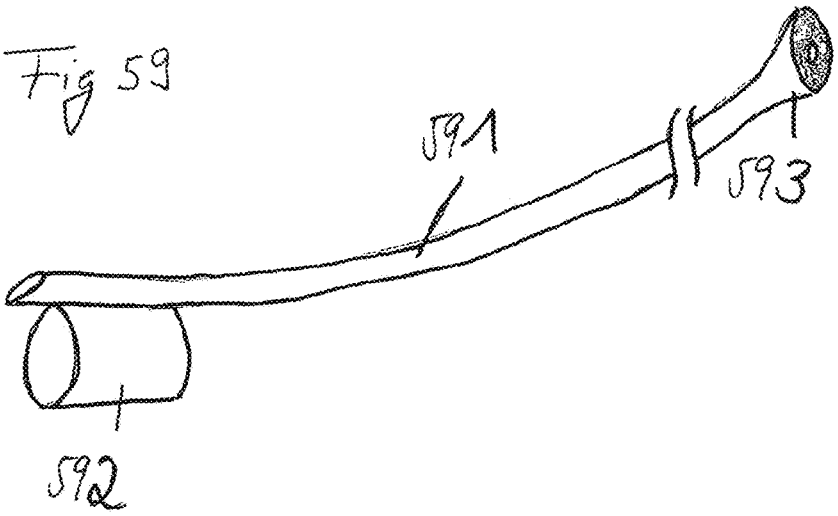
Figure 60:
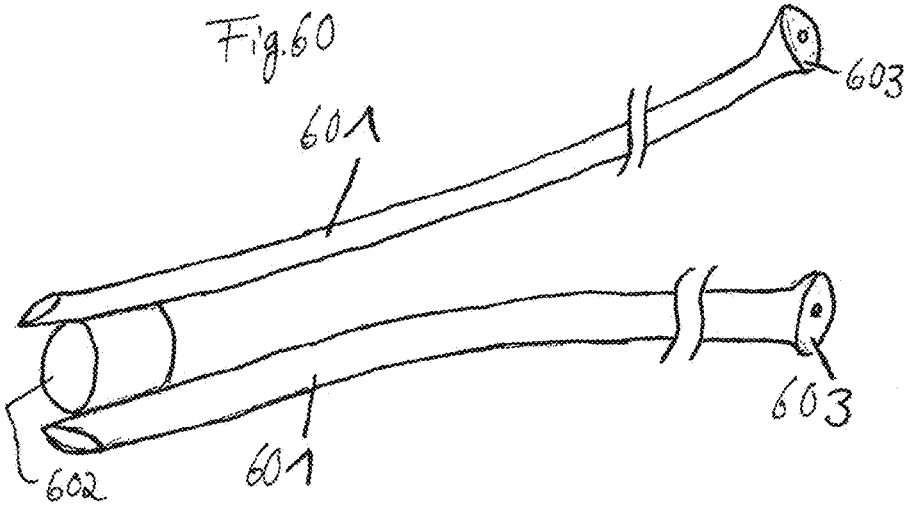
Figure 61:
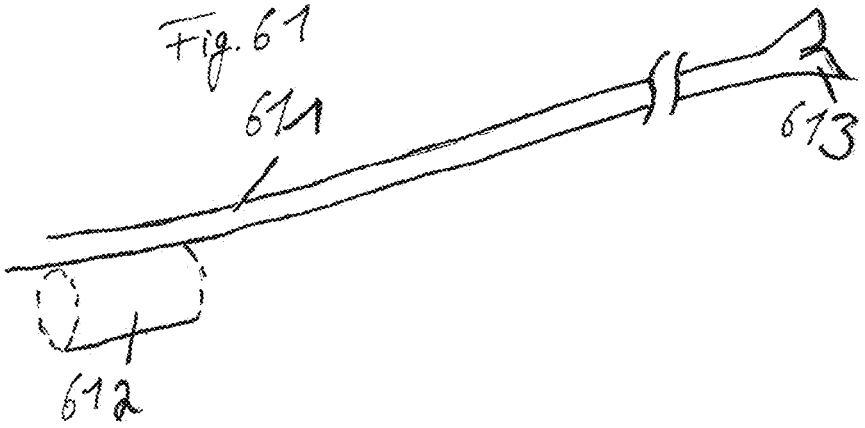
Figure 62:
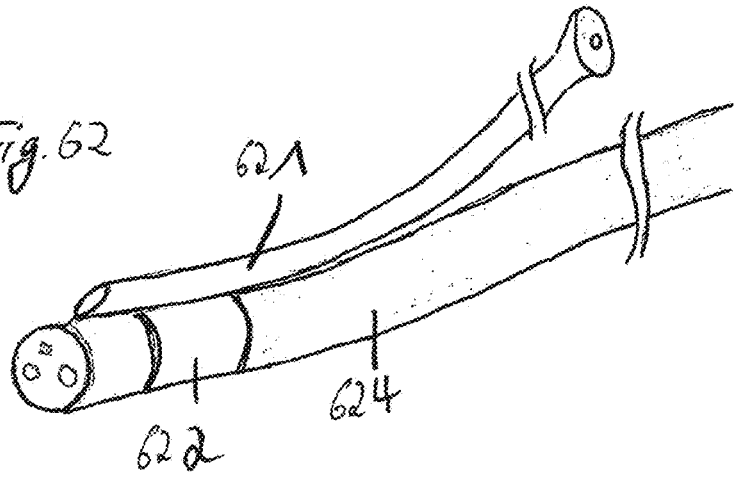
Figure 63:
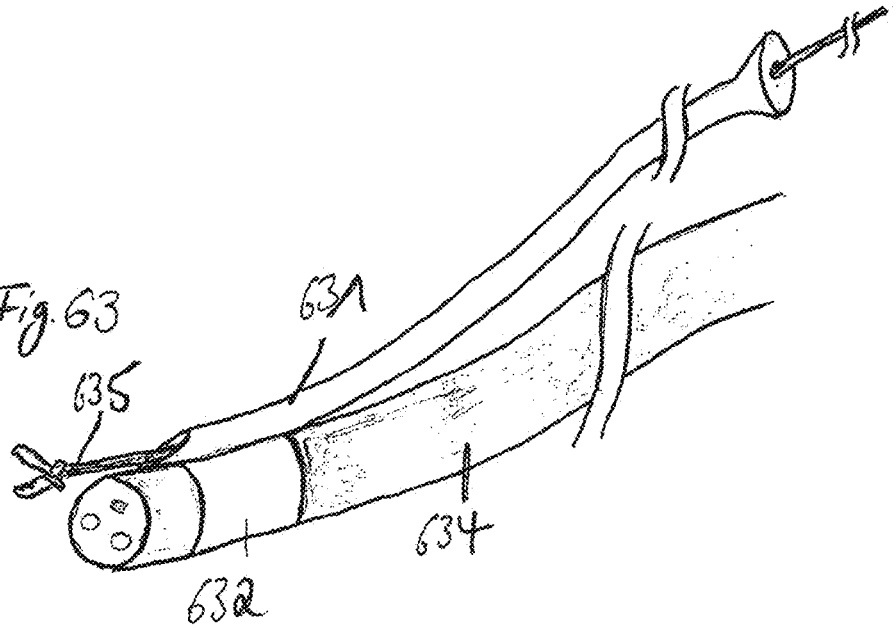

FIGS. 56 a to f are different representations of a drainage hose and pointed top-seated attachments;

FIGS. 57 a to f are different representations of an endoscopic insertion instrument;

FIGS. 58 a to e are different representations of an additional endoscopic insertion instrument;

FIG. 59 is a representation of insertion accessory with a sleeve for attachment to a distal end of an endoscope;

FIG. 60 is a representation of two different different-size insertion accessories;

FIG. 61 shows a cross section of an insertion accessory and of an attachment sleeve with a valve;

FIG. 62 shows a representation of an insertion accessory with an attachment sleeve on a distal end of an endoscope; and FIG. 63 is a representation of an insertion accessory with an attachment sleeve on a distal end of an endoscope.

Figure 1A:
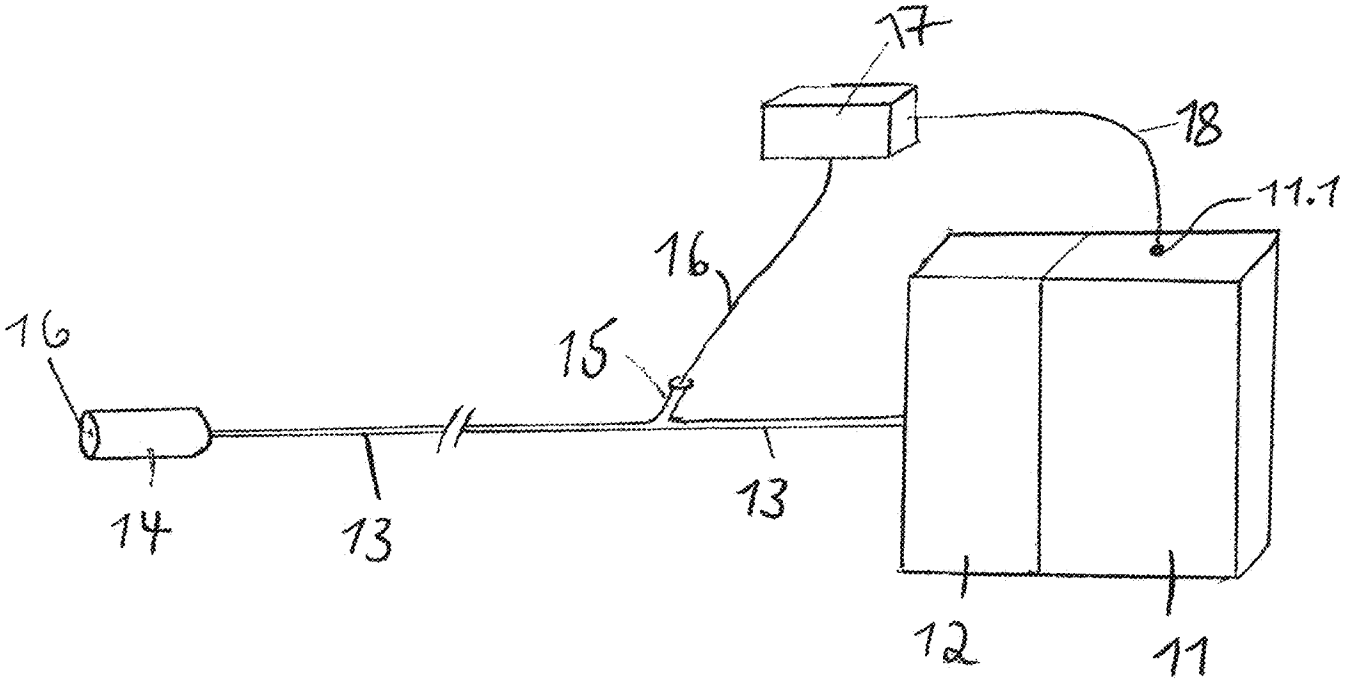
FIG. 1a is a schematic representation of an exemplary embodiment of a vacuum system.

FIG. 1a is a schematic representation of an exemplary embodiment of a vacuum system having a vacuum pump 11, a secretion container 12 on the pump, a fluid communication element 13, which leads from the vacuum pump to a fluid collection element 14. Into the fluid communication element, via a lateral input 15, a negative pressure sensor 16 is introduced, which electronically transmits to the vacuum pump, via a pressure regulating unit 17, measured values for adjusting, presetting and controlling via connecting elements 18. Connected to the pressure regulating unit but not illustrated here in detail (but compare FIG. 1b), is a user input unit. The pressure regulating unit 17 has a test signal input for receiving test signals from negative pressure sensor 16. The latter is designed to control the vacuum pump 11 during operation for generating and maintaining a vacuum at the hollow space to be treated at a predetermined negative pressure of, in this example, between 60 mm Hg and 500 mm Hg, within a predetermined evacuation period between 0.5 and 5 seconds. For this purpose, the vacuum pump 11 has a control input 11.1.

FIG. 1b shows a simplified block diagram with further details of the pressure regulating unit 17 of the vacuum system of FIG. 1a. The pressure regulating unit 17 has a control unit 17.1 implemented as a programmable microprocessor or a microcontroller or a special integrated circuit (ASIC). The control unit receives test signals generated by the negative pressure sensor 16. Furthermore, it is with the user input unit UI. Via the user input unit UI, the physician can input parameters, such as a negative pressure to be set, an evacuation period and a potentially present dead volume. This input need not necessarily take the form of specific values. It may alternatively or additionally, for instance, instead be intended, via user input unit UI, to identify a predefined therapy or examination type by menu selection or text input, for which purpose, in a memory 17.2 of the pressure regulating unit, predefined negative pressure parameters (if applicable, of its development over time) and the evacuation period are stored and can be called up via the input. The dead volume that may have to be taken into account for determining a suction capacity of the connected vacuum pump 11 can be either input quasi automatically by user input, alternatively instead by reading in a code. The pressure regulating unit is designed to determine the required suction capacity of the pump using the negative pressure value on the hollow space to be treated, which (value) is selectable from a predefined negative pressure value interval (automatic value monitoring for reliability after input, using prestored threshold values) and an evacuation period, the value between 0.5 and 5 seconds of which is selectable. Depending on the situation additional parameters are taken into account:

i) figuring in a predetermined dead volume of the vacuum drainage arrangement that is connectable to the vacuum pump, to determine a first suction capacity of the vacuum pump, required for generating the specified negative pressure at the hollow space to be treated within the specified evacuation period, and to transmit a corresponding first control signal to the control input 11.1 of the vacuum pump 11, ii) upon generating the specified negative pressure at the hollow space to be treated, to monitor the pressure test signal and to determine, as a function of the current pressure test signal, a second suction capacity of the vacuum pump, required for maintaining the specified negative pressure, and to transmit a corresponding second control signal to the control input 11.1 of the vacuum pump 11; and iii) upon generating the specified negative pressure at the hollow space to be treated, if a deviation of the measured pressure or negative pressure from the specified negative pressure exists that exceeds a predefined threshold of the measured pressure or negative pressure, to determine a third suction capacity that is required for generating the specified negative pressure within the specified evacuation period and to transmit an appropriate third control signal to the control input 11.1 of the vacuum pump 11.

In the cases ii) and iii), the dead volume must, as a principle, be taken into account as well. It can be neglected for mere maintenance of a vacuum in a variant. In case iii) it must, however, preferably be taken into account.

Via a switch S, which may even be directly integrated into the user input unit UI, it is possible to switch from an endoscopy mode to a therapy mode and back. The difference between the modes lies in the range of values available for the negative pressure. No patient should be exposed to high negative pressure values in the therapy mode without a physician present. Such higher negative pressure values are, therefore, only available in the endoscopy mode. Another difference lies in the input options via the user input unit UI. They are limited in the therapy mode, so that the patient cannot make any undesirable, harmful parameter changes. The switch is secured by a key and can only be activated by the treating physician.

Figure 2:
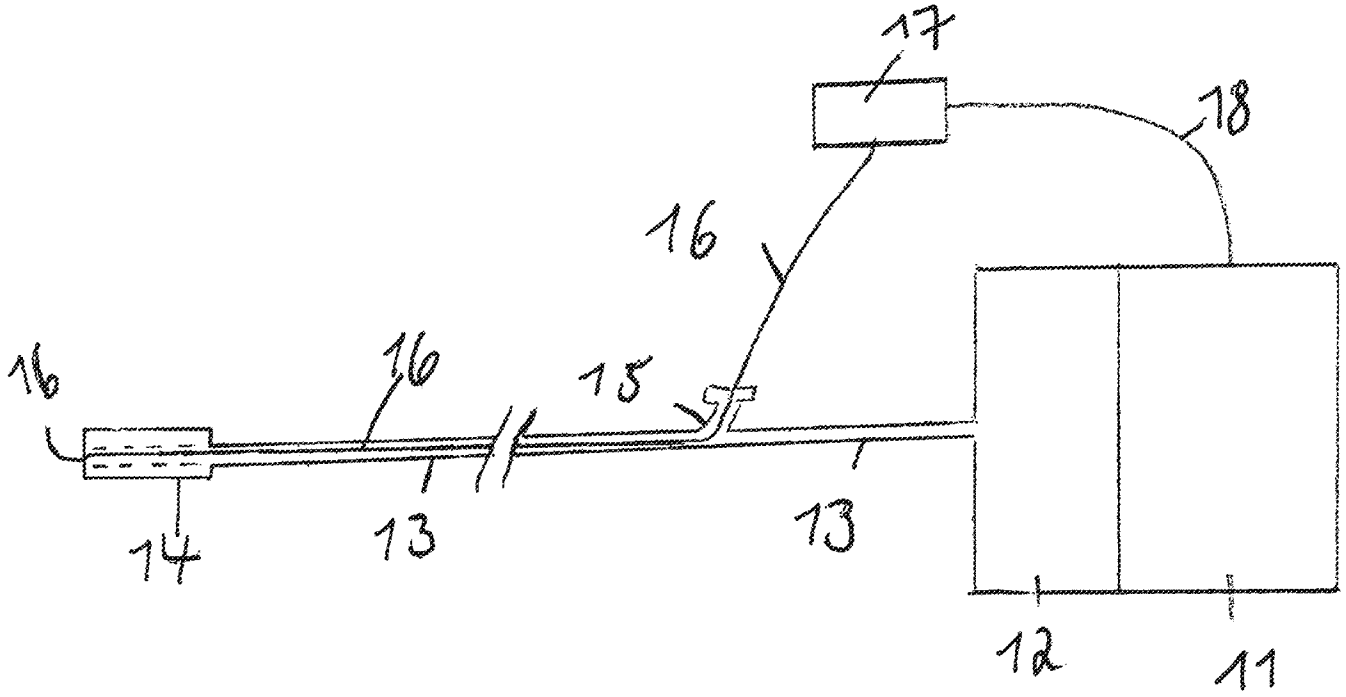

FIG. 2 is a partial longitudinal section of the vacuum system of FIG. 1. Into the fluid communication element, via a lateral input 15, the negative pressure sensor 16 is inserted, which, via the pressure regulating unit 17, transmits the measured values for regulating, preadjusting and controlling to the vacuum pump by means of connecting elements 18.

Figure 3:
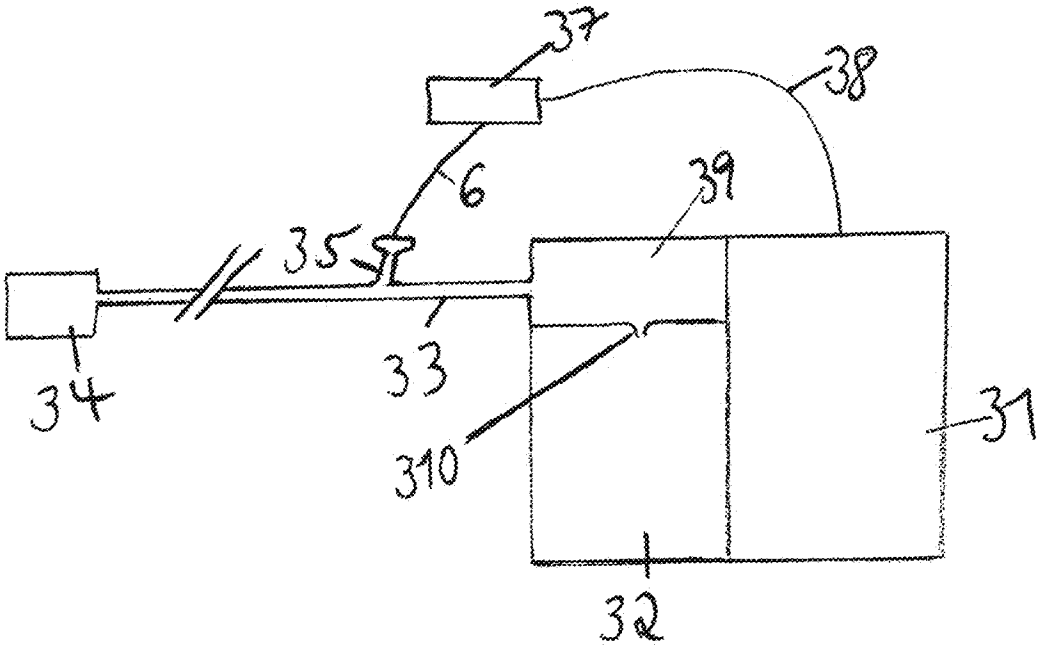
FIG. 3 is a schematic representation of another exemplary embodiment of a vacuum system.

FIG. 3 is a schematic representation of a different exemplary embodiment of a vacuum system with a presecretion container 39 for faster suction build-up and with secretion container 32. The presecretion container is connected to the secretion container via a filter/valve 310. The pressure regulating unit 37 for the negative pressure values, time settings, evacuation periods and for alarm functions is connected to vacuum pump 31 by means of connecting elements 38. A fluid collection element 34 is connected to the pump unit by means of a fluid communication element 33.

Figure 4:
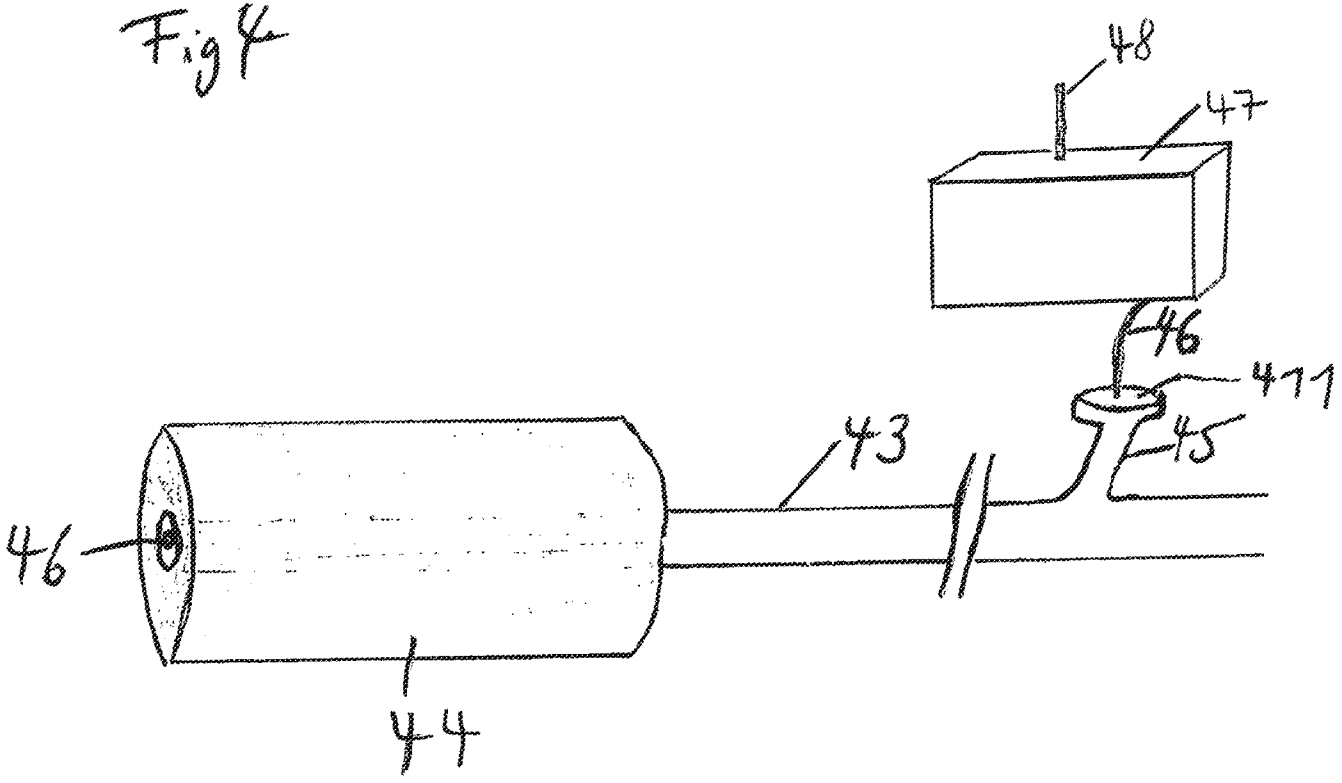
FIG. 4 is a schematic representation of an arrangement of a fluid collection element.

FIG. 4 is a schematic representation of an arrangement of a fluid collection element 44, which is fluid-conducting and connected to a fluid communication element 43. Into the fluid communication element, via a lateral input, through a valve 411, a wire-like negative pressure sensor 46 has been pushed forward up to the fluid collection element 44. The negative pressure sensor is connected to a measuring and pressure regulating unit 47, which can forward the test signals of the negative pressure sensor via an electronic connection 48.

Figure 5:
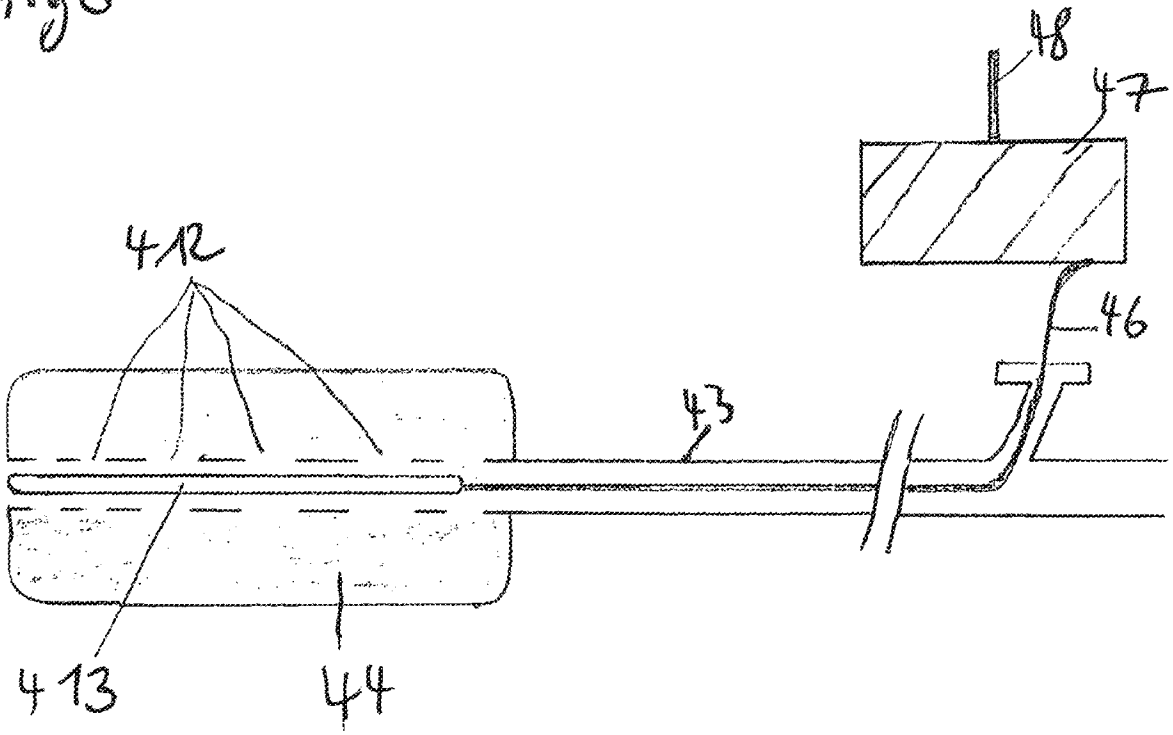
FIG. 5 is a schematic partial longitudinal section of the arrangement of FIG. 4.

FIG. 5 is a schematic partial longitudinal section of the arrangement of FIG. 4. The fluid collection element 44 is connected to the fluid communication element 43, at the distal end of which fluid-conducting openings 412 exist for suction. Into the fluid communication element, a wire-like negative pressure sensor 46 has been advanced up to the fluid collection element. At the distal end of negative pressure test probe 413 of the sensor is attached. The test probe is connected to a measuring and pressure regulating unit 47, which can forward the information via an electric connection 48.

Figure 6:
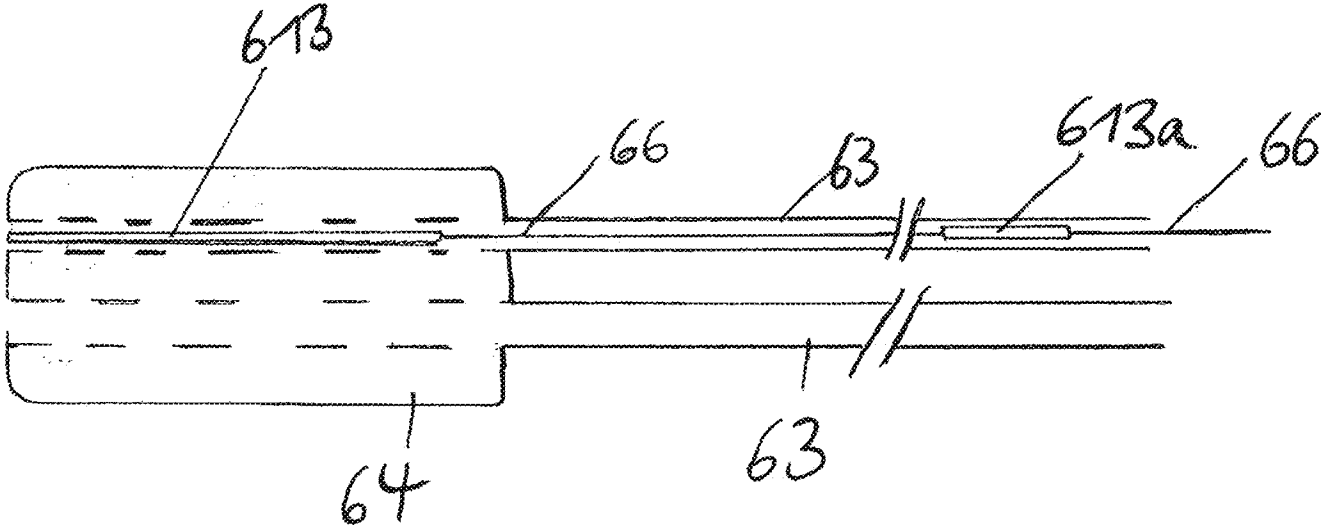
FIG. 6 is a longitudinal section of a fluid collection element 64, which is connected, fluid conducting, to two fluid communication elements 63.

FIG. 6 is a longitudinal section of a fluid collection element 64, which is fluid-conducting and connected to two fluid communication elements 63 into one of the fluid communication elements, a wire-like negative pressure measuring sensor 66 has been advanced up to the fluid collection element. At its distal end, a negative pressure sensor 613 is attached. Another negative pressure sensor 613a exists in the fluid collection medium.

Figure 7:
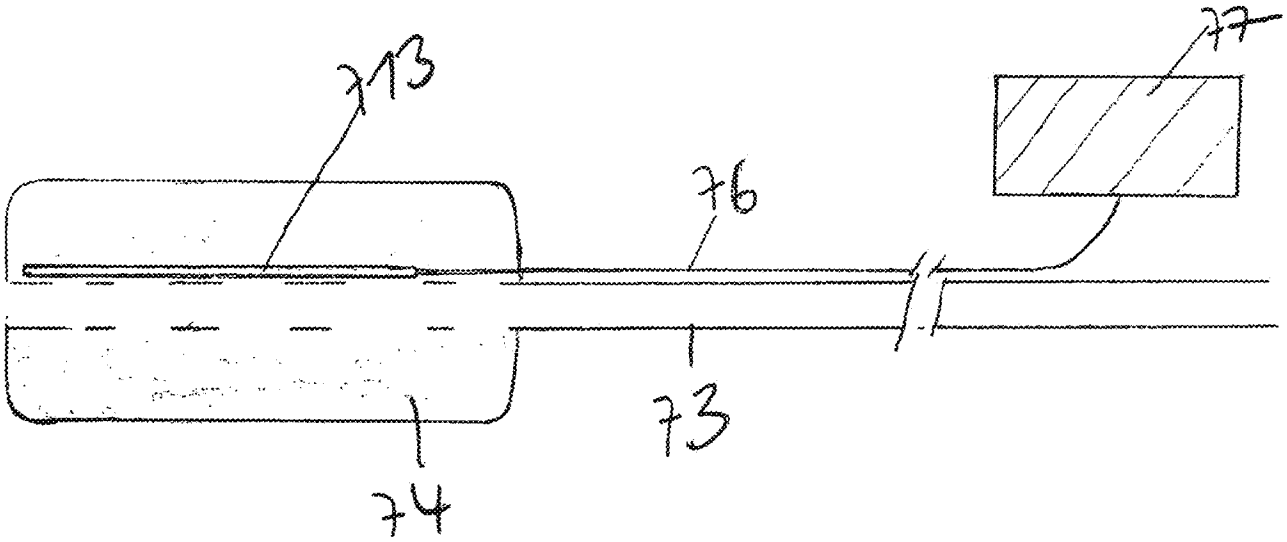
FIG. 7 is a longitudinal section of a fluid collection element, in which both a fluid conducting fluid communication element and imposed on it, a wire-like negative pressure sensor is arranged.

FIG. 7 is a longitudinal section of a fluid collection element 74, in which is arranged both, a fluid-conducting fluid communication element 73 and, imposed on it, a wire-like negative pressure sensor 76. The negative pressure sensor 76 is connected to a pressure regulating unit 77 and is equipped, at its distal end, with a negative pressure sensor 713 which is located in the fluid collection element. The pressure regulating unit is enhanced by an alarm function. Electronic control signals are transmitted for regulation of the negative pressure, in particular to the vacuum pump. Alarms regarding a malfunction can be triggered.

Figure 8:
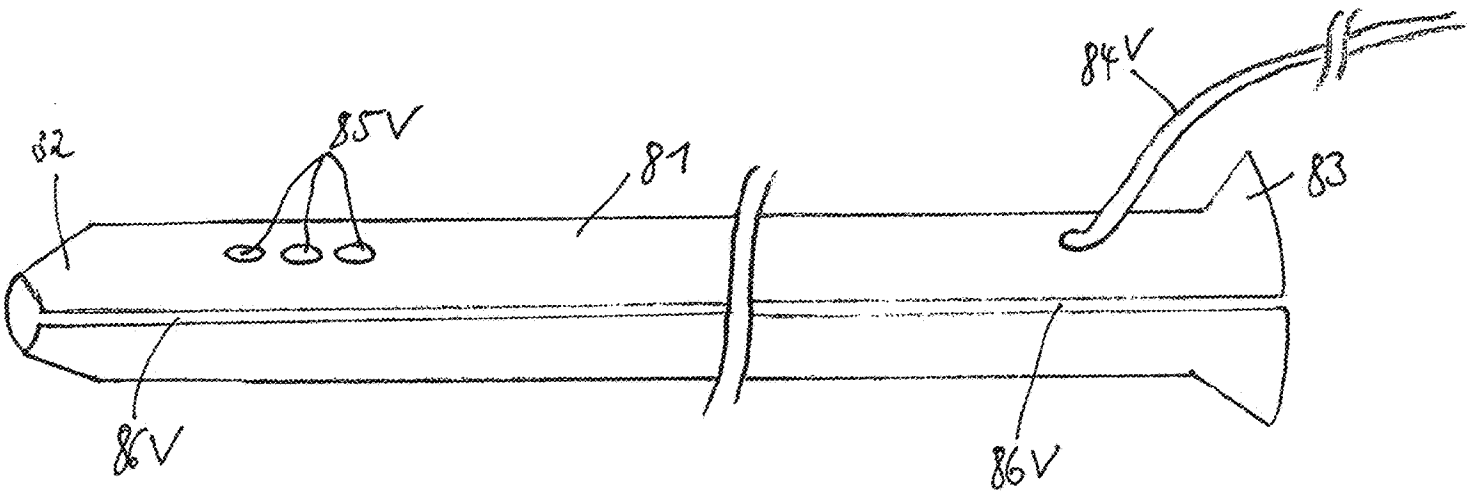
FIG. 8 shows an embodiment of a longitudinally slotted overtube.

FIG. 8 is a representation showing an embodiment of a longitudinally slotted overtube 81. At its distal end, overtube 81 is conically tapered to prevent injury during insertion. Over the entire length, a complete slot 86V exists. At its proximal end 83, overtube 81 is designed funnel-shaped to facilitate insertion of an endoscope. The overtube is provided with a fluid communication element 84V in the form of a drainage line, which is integrated in the wall and extends from proximal to distal. It ends at the distal end in lateral openings 85V and perforates the wall of the overtube by means of them. At the proximal end, it exits hose-like (84V) and can be connected here to the vacuum device.

Figure 9:
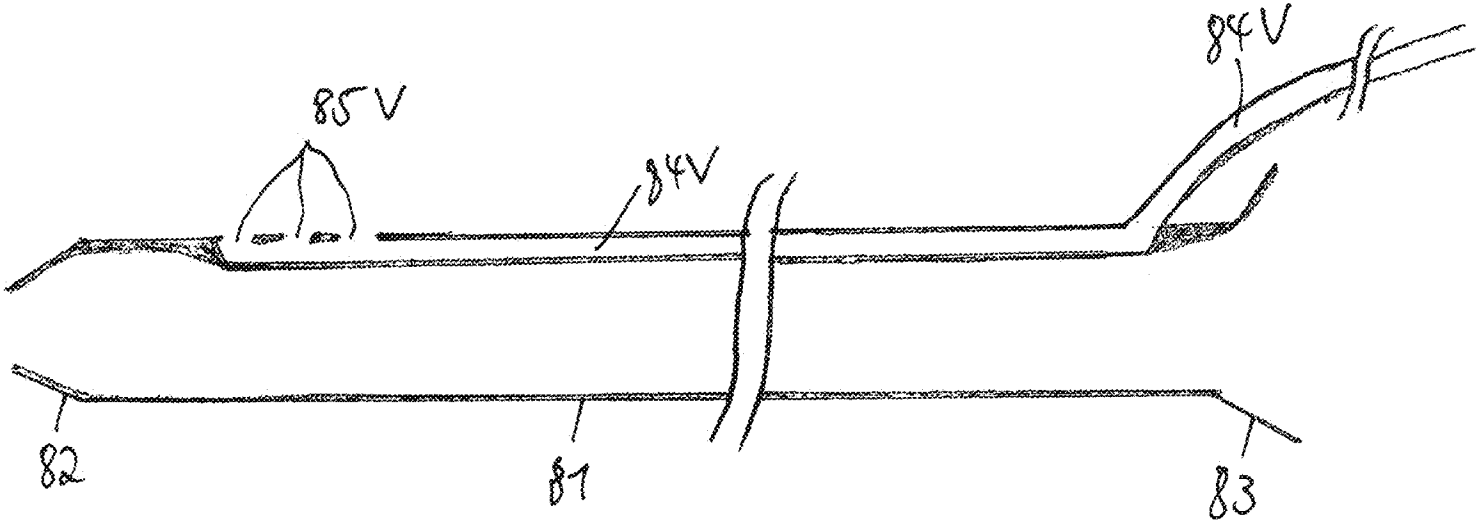
FIG. 9 is a longitudinal section of FIG. 8.

FIG. 9 is a longitudinal section of the overtube 81 of FIG. 8, including representation of overtube 81, which tapers at the distal end 82, widens funnel-shaped at the proximal end 83, and includes fluid communication element 84V, which ends at its distal end in fluid-conducting wall openings 85V, and is conducted out hose-like from the wall.

Figure 10:
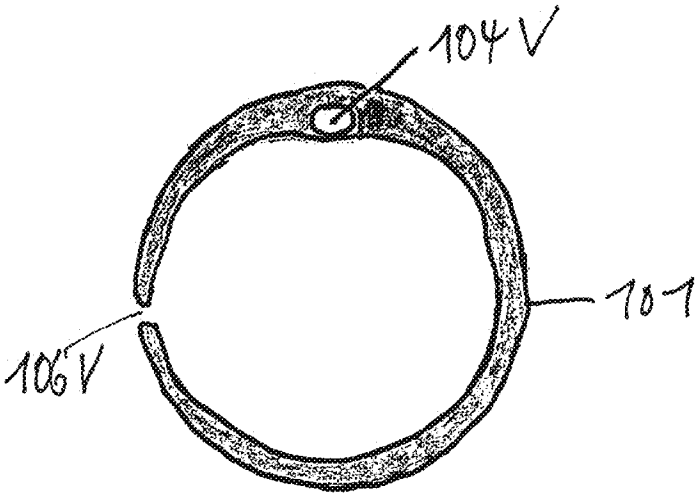
FIG. 10 is a cross-section of an overtube.

FIG. 10 is a cross-section of a different exemplary embodiment of an overtube 101 with a fluid communication element 104V integrated in the wall. The overtube 101 is shown with a longitudinal slot 106V.

Figure 11:
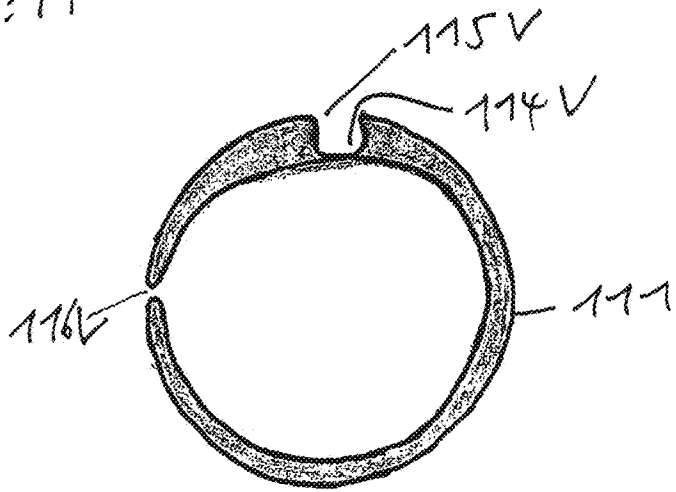
FIG. 11 is a cross-section of a different variant of an overtube.

FIG. 11 is a cross-section of a different variant of an overtube 111, having, integrated in the wall, a fluid communication element 114V, which is fluid-conducting and perforates the wall by means of an opening 115V and is fluid-conducting and connected to the outside wall of overtube 111. The cross-section is drawn at the level of wall opening 115V. The overtube is represented with a longitudinal slot 116V.

Figure 12:
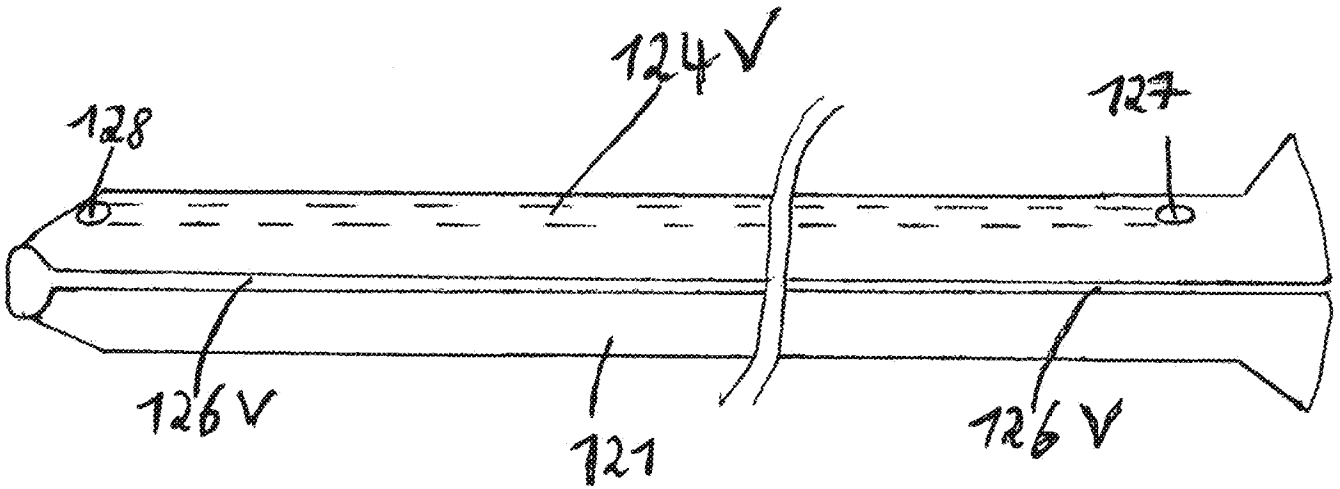
FIG. 12 shows an additional embodiment of an overtube.

FIG. 12 is a representation showing an embodiment of an overtube 121. Over entire length, a longitudinal slot 126V exists. Overtube 121 is equipped with a fluid communication element 124V in the form of a working channel integrated in the wall and extending from a proximal wall opening 127 of the overtube to the distal tip and ends here with a distal wall opening 128.

Figure 13:
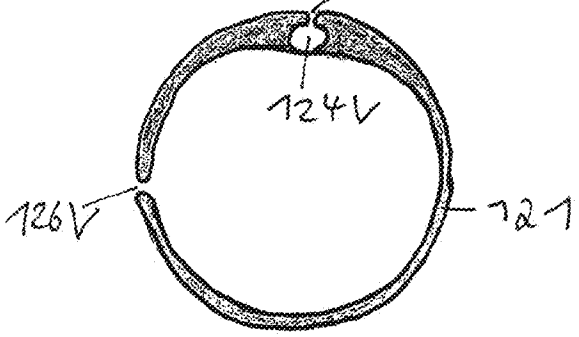
FIG. 13 is a cross-section of the overtube of FIG. 12.

FIG. 13 is a cross-section of the overtube 121 of FIG. 12, the channel-type fluid communication element 124V being provided with a longitudinal slot 1210. The fluid communication element is integrated into the wall of overtube 121. The overtube is also represented with the longitudinal slot 126V.

Figure 14:
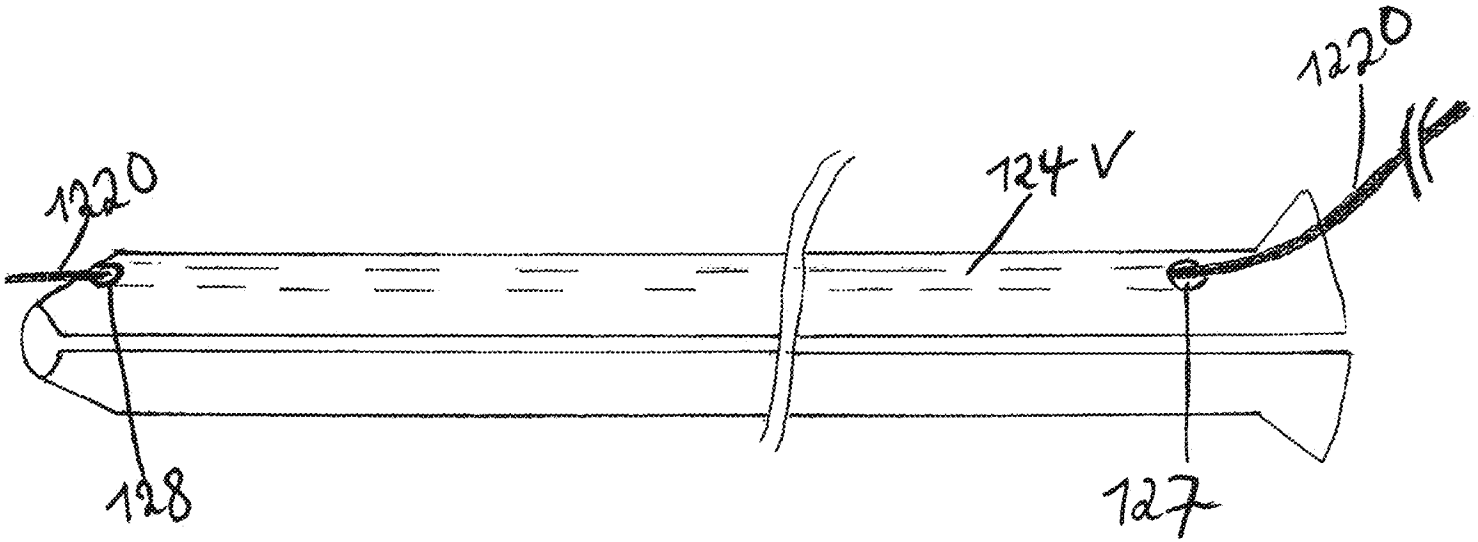
FIG. 14 is a different representation of the embodiment of FIGS. 12 and 13.

FIG. 14 is a different representation of the embodiment of FIGS. 12 and 13, into the fluid communication element 124V, via the proximal opening 127, a medical instrument 1220, herein a guidewire, having been introduced and conducted out through it via the distal opening 128.

Figure 15:
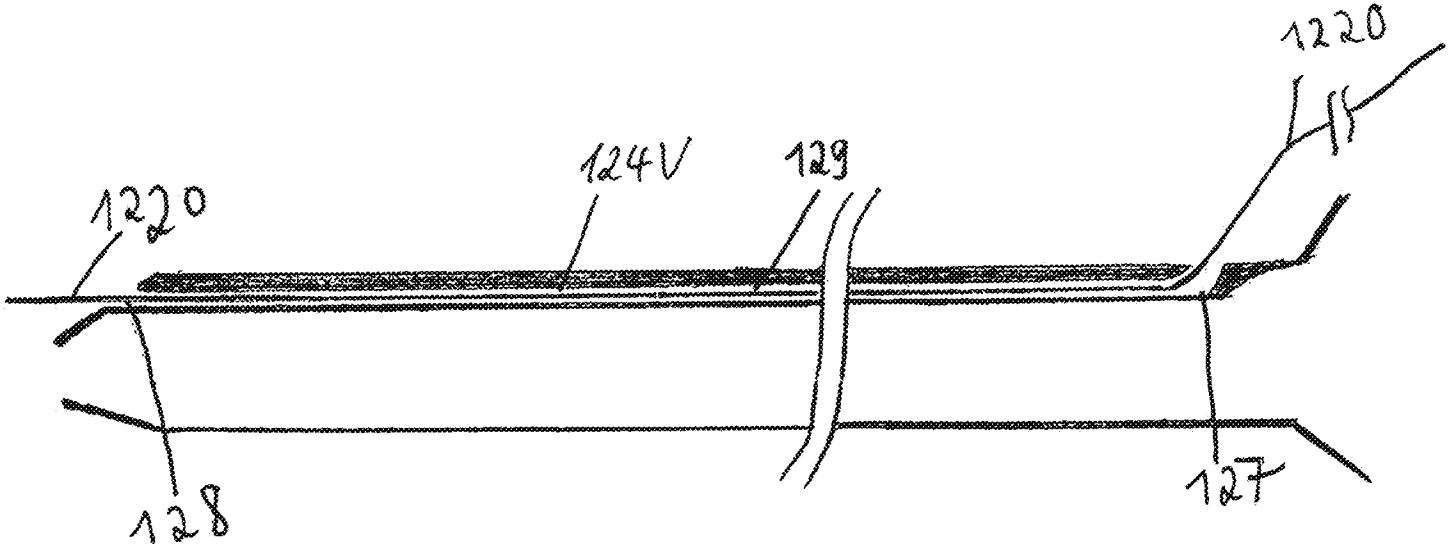
FIG. 15 is a longitudinal representation of FIG. 14.
Figure 16:
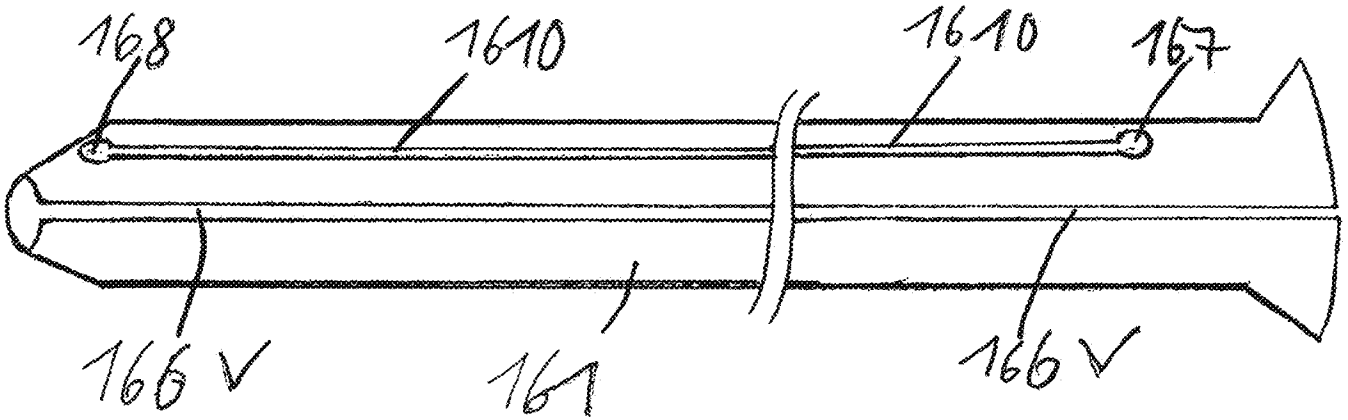

FIG. 15 is a longitudinal section of overtube 121 which shows the working channel 129 that is integrated into the wall of overtube 121 as well as the proximal wall opening 127 and the distal wall opening 128.

Figure 16:
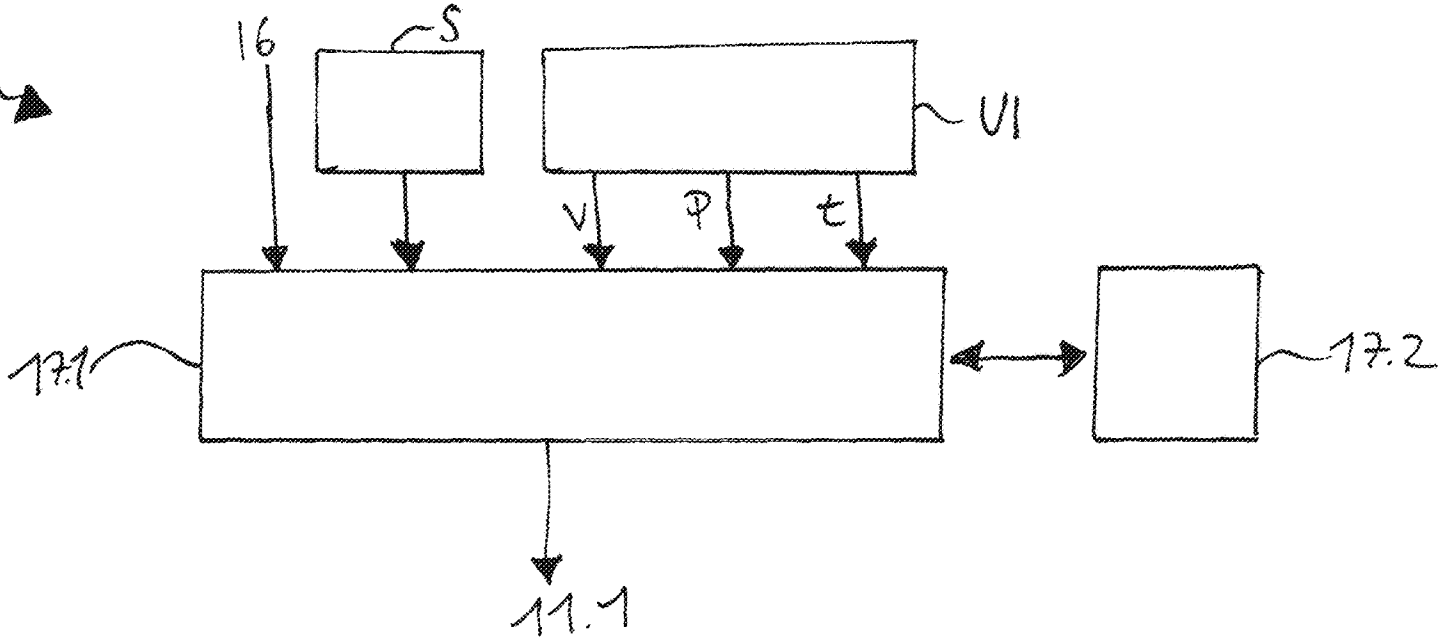
FIG. 16 is a representation of an overtube, which forms a variant of the overtube of FIGS. 12 to 15.

FIG. 16 is a representation of an overtube 161 that embodies a variant of the overtube of FIGS. 12 to 15. A working channel integrated into the wall of overtube 161 has, over the entire length between proximal wall opening 167 and distal wall opening 168, a longitudinal slot 1610. Overtube 161 also has a longitudinal slot 166V over the entire length in this embodiment.

Figure 17:
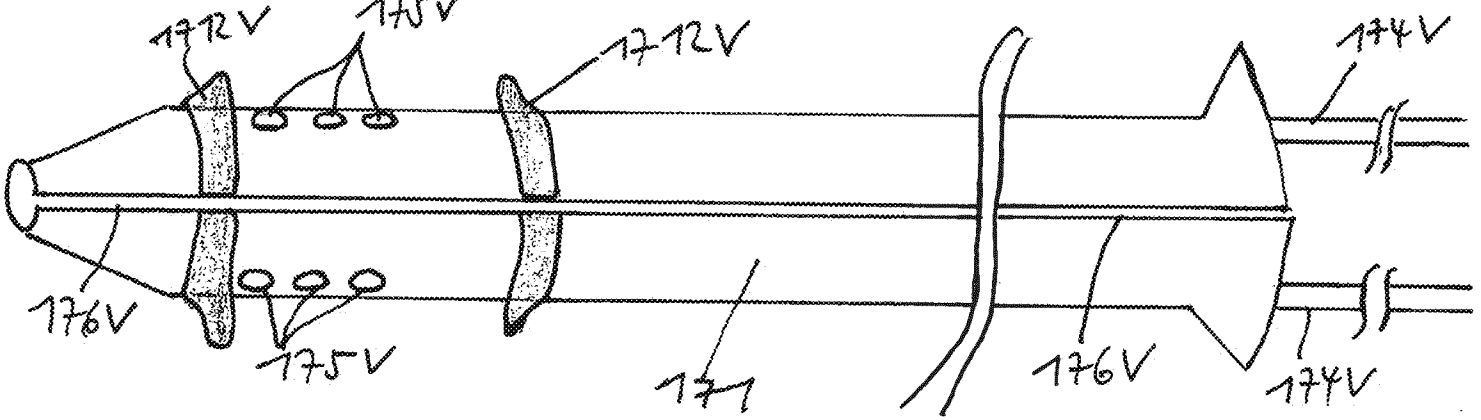
FIG. 17 is a representation of a different variant of an overtube.

FIG. 17 is a representation of an overtube 171, over the entire length of which a complete slot 176V exists. Overtube 171 is equipped with two fluid communication elements 174V in the form of drainage lines, which are integrated into the wall of the overtube. They end in lateral openings 175V at the distal end of the overtube. The proximal ends 1711 of the fluid communication elements are fluid-conducting and connected to the vacuum unit. Attached to the overtube, proximal and distal relative to the lateral openings 175V of the fluid communication elements are annular lip-like swells 1712V.

Figure 18:
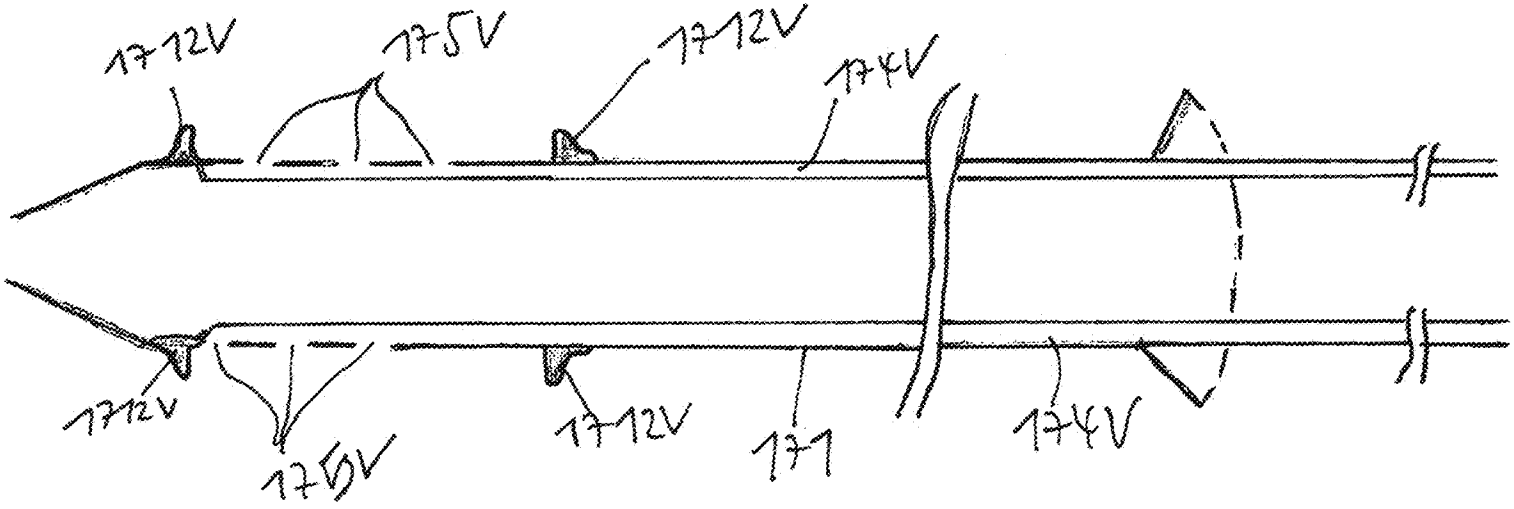
FIG. 18 is a longitudinal section of the overtube of FIG. 17.

FIG. 18 is a longitudinal section of overtube 171 of FIG. 17, which shows the two fluid communication elements 174V, which are fluid-conducting and end laterally in the distal end of the overtube with openings 175V. Proximal and distal of these, the annular lip-shaped swells 1712V are attached to the overtube.

19 shows a variant of the representations of the embodiments of FIG. 17 and FIG. 18, here, at the level of the distal wall openings 175V, between the annular swells 1712V, additionally, the fluid collection element 1713V being attached. The fluid collection element is also provided with a longitudinal slot 176V on the longitudinal axis of overtube 171.

Figure 19:
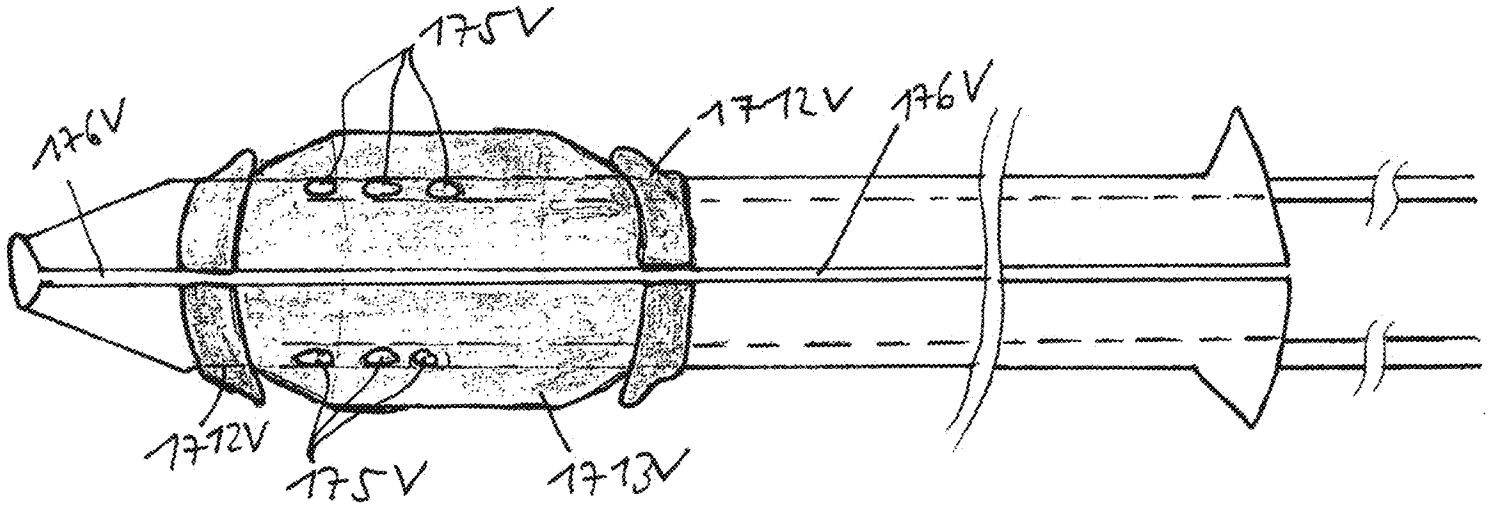
FIG. 19 shows a variant of the representations of the embodiments of FIG. 17 and FIG. 18.
Figure 20:
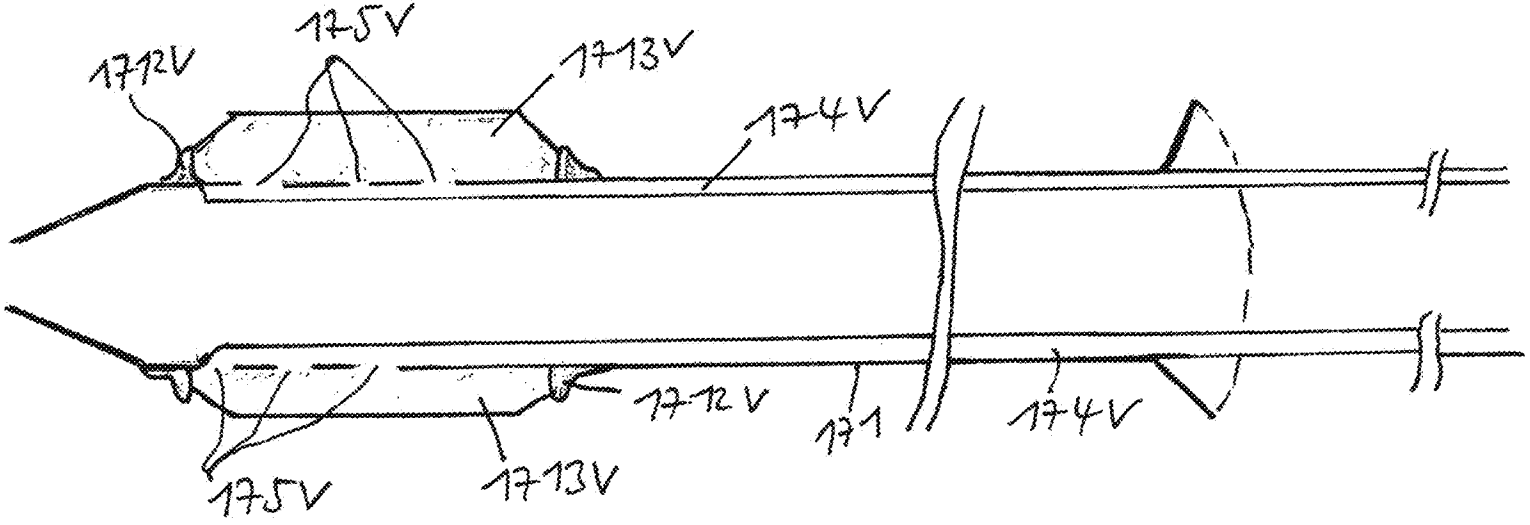
FIG. 20 is a longitudinal section of the overtube FIGS. 18 and 19.

FIG. 20 is a longitudinal section of overtube 171 of FIGS. 18 and 19, which shows clearly the fluid communication elements 174V with the fluid-conducting wall openings 175V, fluid collection element 1713V attached above and proximal and distal lip-like swells 1712V.

FIG. 21 is an additional longitudinal section of the overtube of FIGS. 18 to 20, which shows the fluid communication elements 174V, with the fluid-conducting wall openings 175V and the proximal and distal lip-like swells 1712V. In addition, a wire-like measuring sensor 1719 is represented, which was introduced into one of the fluid communication elements and which ends distally in a negative pressure measuring unit 1721. The measuring sensor 1719 has been introduced into the fluid communication element 174V via a valve 1722.

Figure 22:
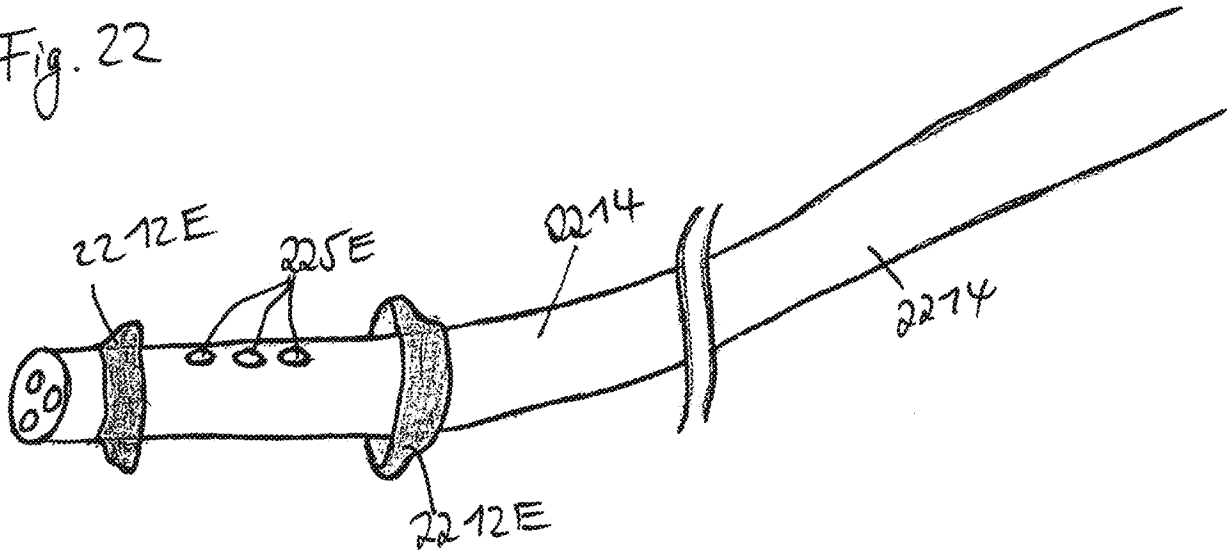
FIG. 22 is a representation of a distal end of an endoscope.

FIG. 22 is a representation of a distal end of an endoscope 2214. At the distal end of endoscope 2214, lateral fluid-conducting wall openings 225E of a fluid communication element incorporated in the endoscope are represented. Proximal and distal relative to these wall openings 225E, lip-like rings 2212E are attached to endoscope 2214.

Figure 23:
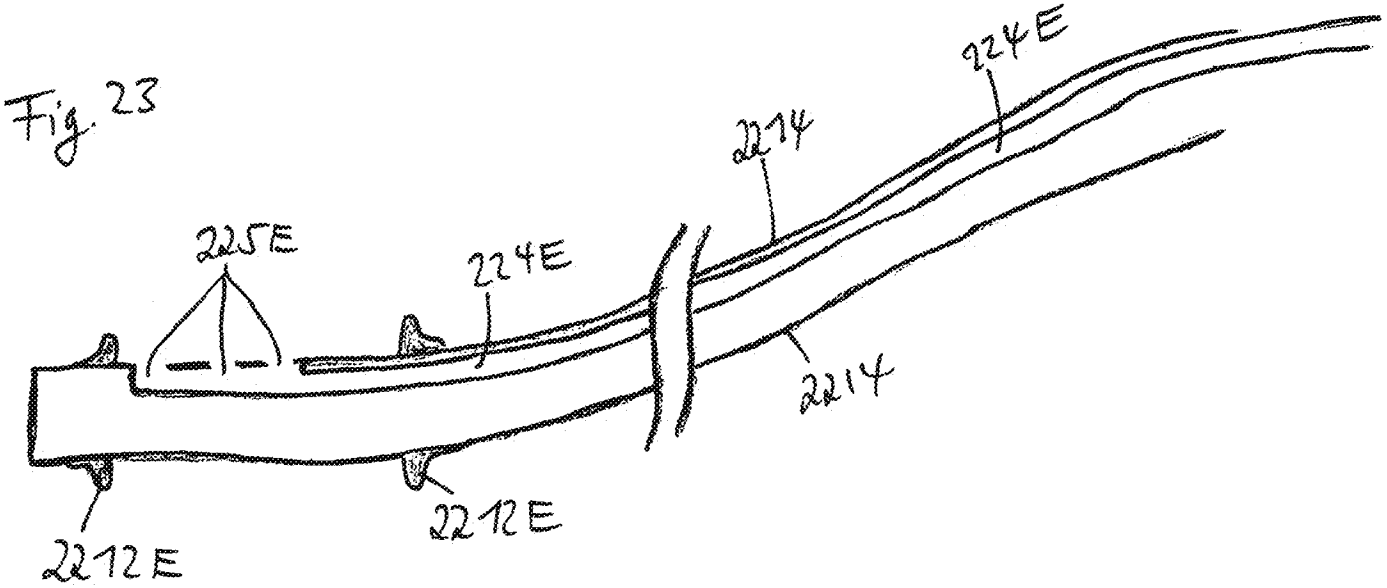
FIG. 23 is a longitudinal section of the endoscope of FIG. 22.

FIG. 23 is a longitudinal section of endoscope 2214 of FIG. 22 showing the internally-situated fluid communication element 224E, the lip-like rings 2212E proximal and distal relative to the lateral openings 225E of fluid communication element 224E.

Figure 24:
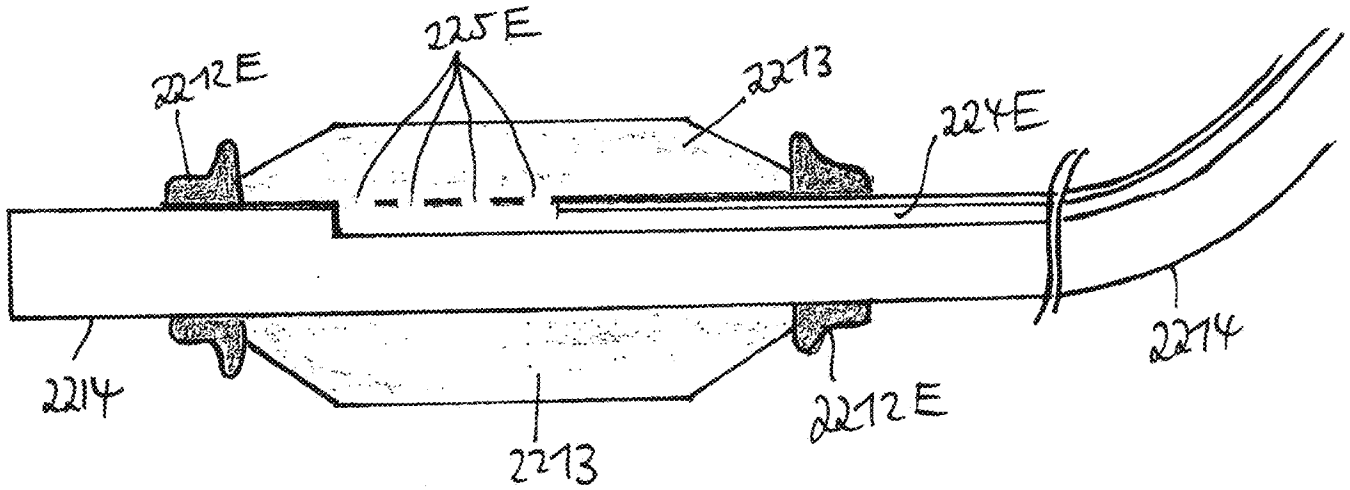
FIG. 24 is an additional longitudinal section of the endoscope of FIG. 22.

FIG. 24 is an additional longitudinal section of endoscope 2214 of FIG. 22. In this representation, above the fluid-conducting openings of fluid communication element 224E, between the lip-like rings 2212E, a fluid collection element 2213E is inserted.

Figure 25:
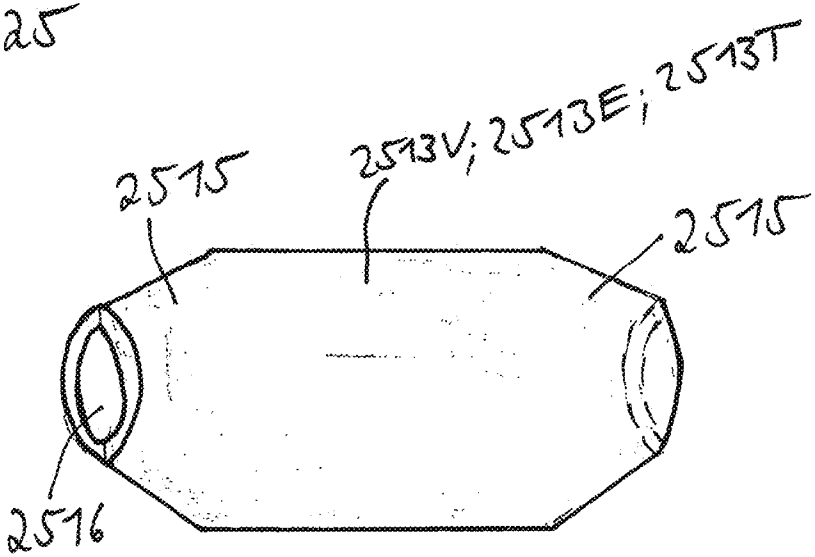
FIG. 25 is a representation of a fluid collection element suitable for use on the overtube, the endoscope and the support sleeve.

FIG. 25 is a representation of a fluid collection element 2513V, 2513E, 2513T, which is suitable for use on the overtube, the endoscope and the support sleeve. In this embodiment, the fluid collection element has, at its ends, a conical taper 2515. A channel 2516 is arranged centrally along the longitudinal axis of the fluid collection element.

Figure 26:
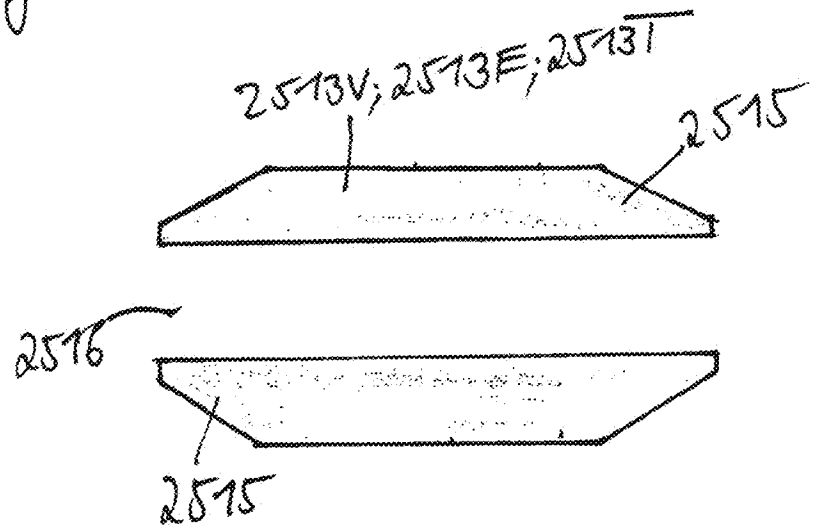
FIG. 26 is a longitudinal section of the fluid collection element of FIG. 25.
Figure 27:
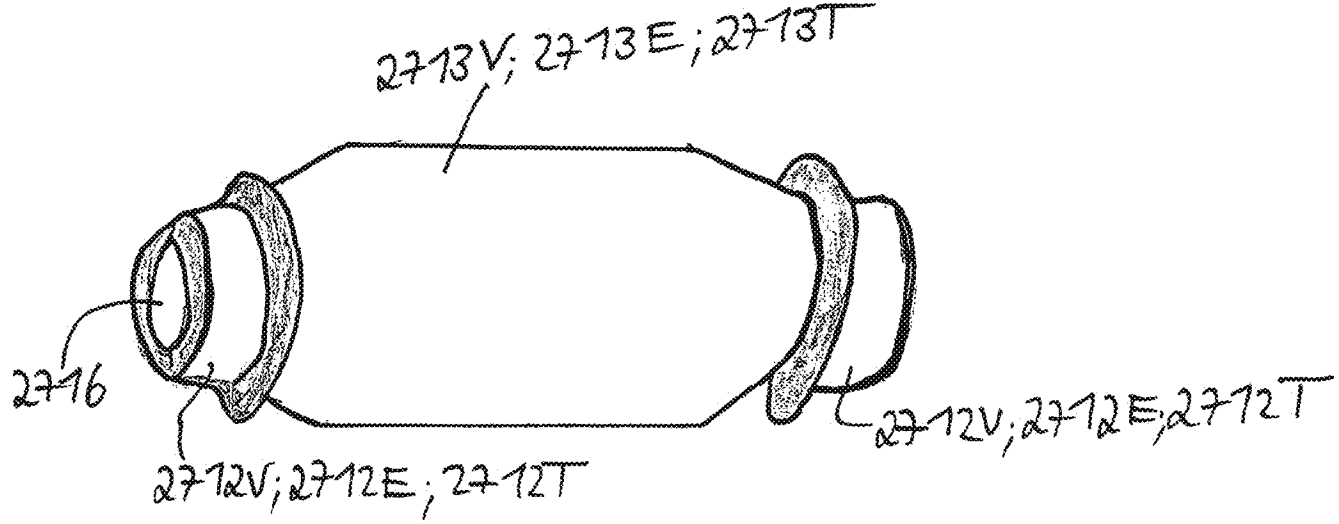

FIG. 26 is a longitudinal section of fluid collection element 2513V, 2513E, 2513T of FIG. 25. The conical taper 2515 can be recognized at the ends and at the central channel 2516 along the longitudinal axis.

Figure 27:
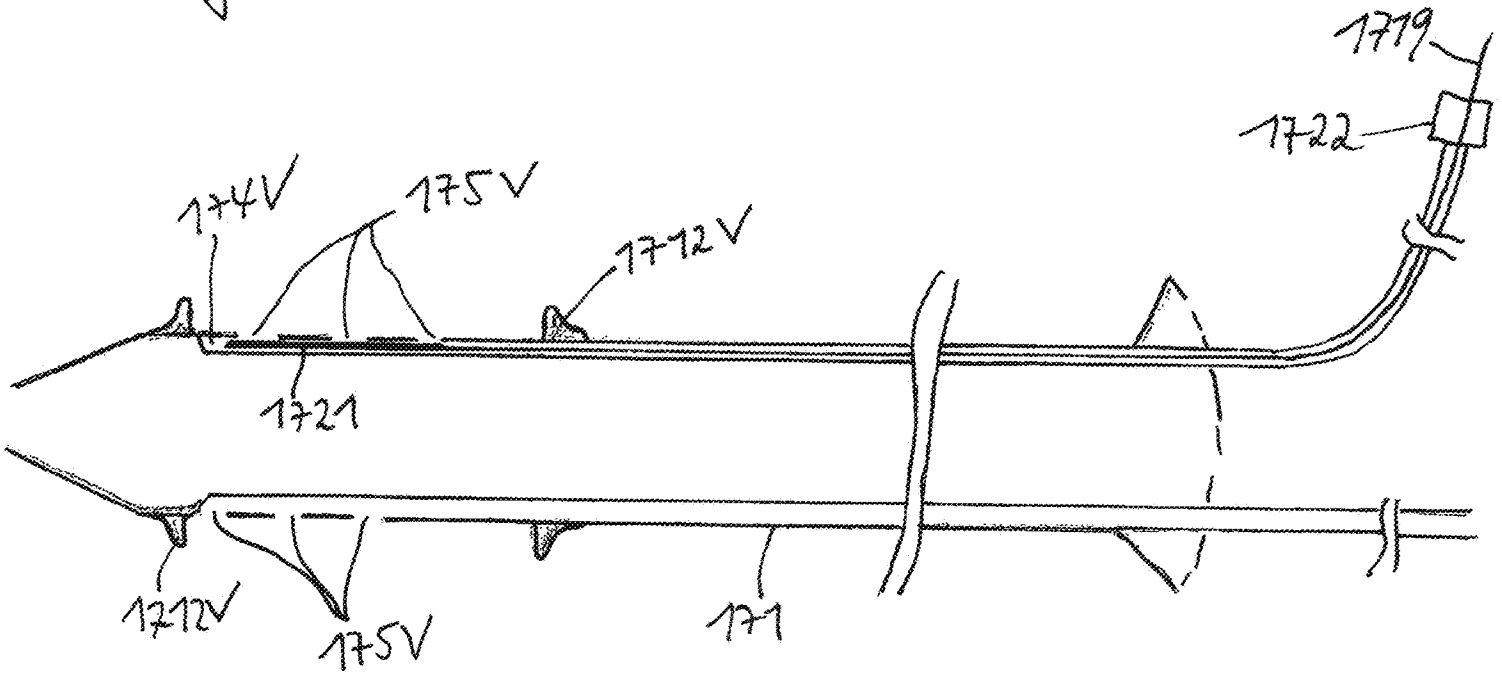
FIG. 27 is a representation of a different fluid collection element.

FIG. 27 is a representation of another fluid collection element 2713V, 2713E, 2713T for overtube, endoscope and support sleeve, a lip-like ring 2712V, 2712E, 2712T being attached to each end of the element. A joint central channel 2716 extends through the fluid collection element.

Figure 28:
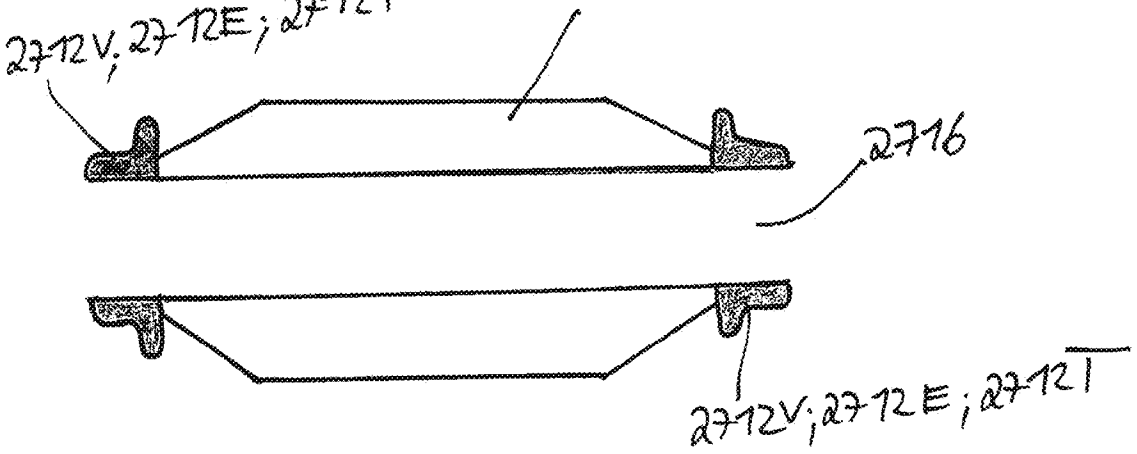
FIG. 28 is a longitudinal section of FIG. 27.

FIG. 28 is a longitudinal section of FIG. 27 with fluid collection element 2713, 2713E, 2713T, a lip-like ring (2712V, 2712E, 2712T) being attached to each end.

Figure 29:
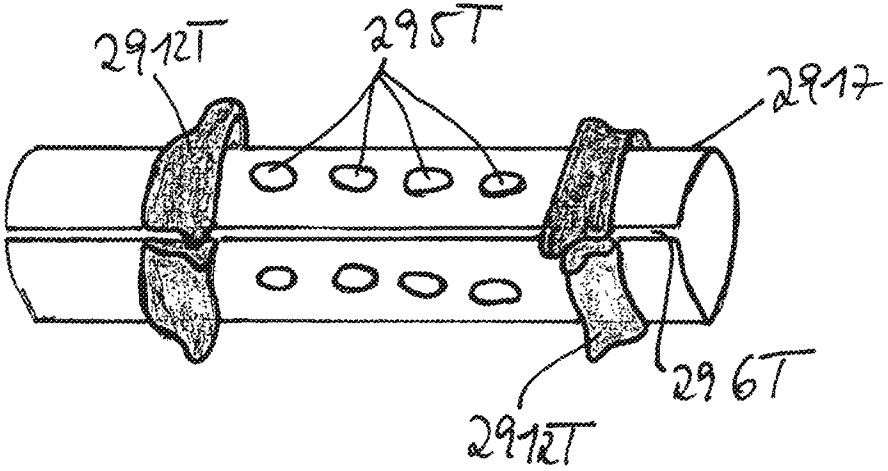
FIG. 29 is a representation of a support sleeve for a fluid collection element.

FIG. 29 is a representation of a support sleeve 2917 for a fluid collection element, shown with a longitudinal slot 296T, fluid-conducting wall perforations 295T and lip-like rings 2912ST proximal and distal relative to the wall perforations 295T. The rings are also slotted.

Figure 30:
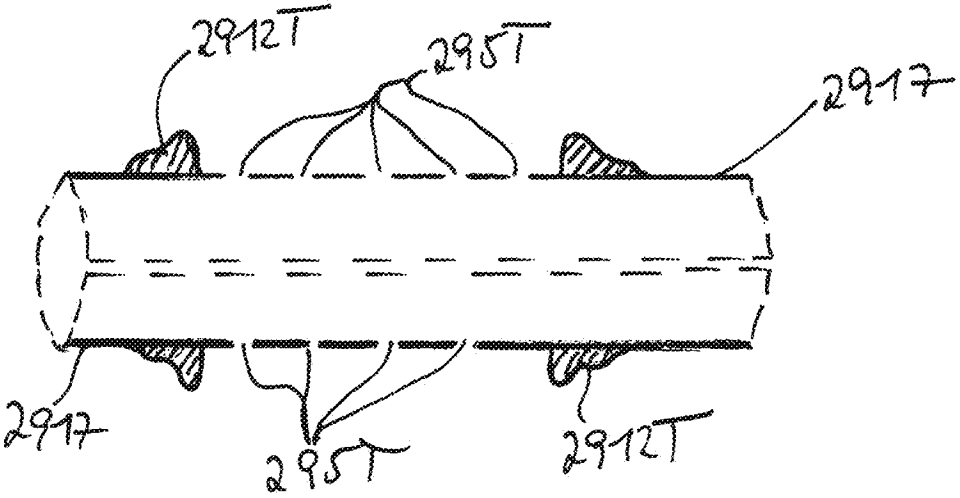
FIG. 30 is a longitudinal section of the support sleeve of FIG. 29.

FIG. 30 is a longitudinal section of the support sleeve of FIG. 29 and shows the fluid-conducting wall perforations 295T and the lip-like rings 2912T proximal and distal relative to the wall perforations 295T.

Figure 31:
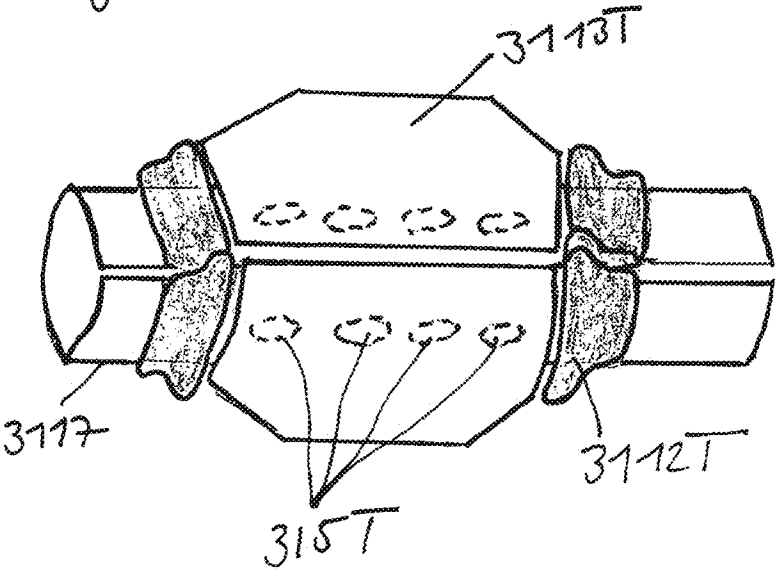
FIG. 31 is a representation of a support sleeve having, attached on it between lip-like rings, a longitudinally slotted fluid collection element.

FIG. 31 is a representation of a support sleeve 3117 having, attached on it, between lip-like rings 3112T, a longitudinally slotted fluid collection element 3113T. Wall perforations 315 of the support sleeve are indicated by dashed lines.

Figure 32:
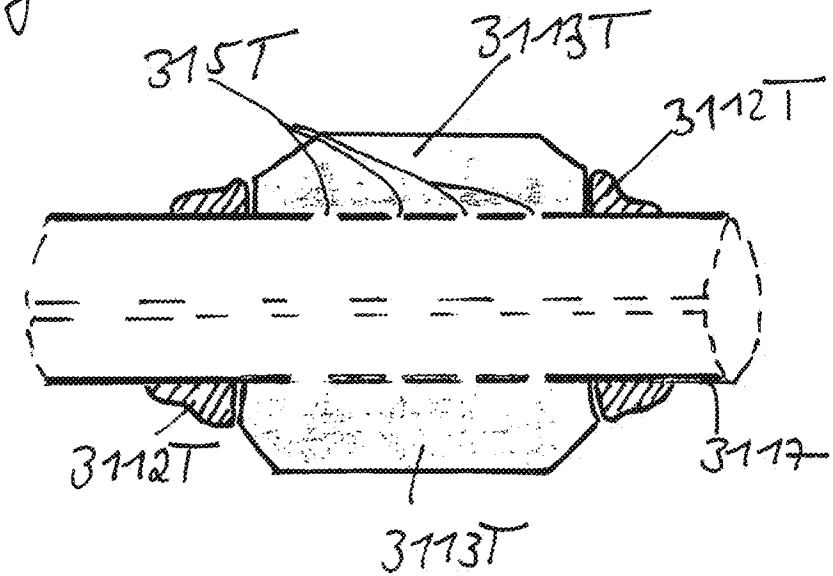
FIG. 32 is a longitudinal section of the support sleeve FIG. 31.

FIG. 32 is a longitudinal section of the support sleeve of FIG. 31, on support sleeve 3117, between the lip-like rings 3112T and fluid-conducting with the wall perforations 315T, fluid collection element 3113T being attached.

FIGS. 33 a-i show different variants of cross-sectional profiles of the lip-like ring closures 3112V, 3112E, 3112T, which are mounted to an exterior wall 3118V, 3118E, 3118T of overtube, endoscope or support sleeve.

FIG. 34 shows a flexible endoscope 3414 in a state, in which it is introduced and removed via longitudinal slot 346V of an overtube 341. To the endoscope and the overtube, fluid collection elements 3413E, 3413V are mounted, in each case at the distal end. The fluid communication element 344V is connected fluid-conductive to the fluid collection element of overtube 3413V.

FIG. 35 shows an endoscopy arrangement according to an additional exemplary embodiment. Represented is a vacuum pump unit 3521 having a secretion collection container 3522, to which an overtube 351 and an endoscope 5614 are connected. To the distal ends of overtube 351 and endoscope 3514, fluid collection elements 3513V and 3513E are attached, which are connected to vacuum pump unit 3521 via the fluid-communication elements 354V (overtube) and 354E (endoscope).

FIG. 36 a-n is a schematic representation of the examination process of a vacuum endoscopy. The treatment comprises the following steps:

a) insertion of endoscope 3614 with fluid collection element 3613E into an intestine 3625 of a patient;
b) Subsequent insertion of overtube 361 with fluid collection element 3613V above the endoscope;
c) Subjecting fluid collection element 3613V to a vacuum;
d) Pushing endoscope 3614 forward in the intestine;
e) Subjecting fluid collection element 3613E on endoscope 3614 to a vacuum; during this step, no vacuum application to fluid collection element 3613V on overtube 361;
f) Pushing overtube 361 on above the attached endoscope 3614;
g) Subjecting both fluid collection elements 3613E and 3613V to a vacuum;
h) Optional straightening maneuver if necessary, by retracting the fluid collection element 3613E together with the fluid collection element 3613V, both subject to vacuum application;
i) Disconnecting the vacuum application to fluid collection element 3613E while maintaining the vacuum application to fluid collection element 3613V;
j) Pushing endoscope 3614 forward while overtube 361 is held in place by the vacuum;
k) Maintaining the vacuum application to fluid collection element 3613E, disconnecting the vacuum application to fluid collection element 3613V;
l) Pushing overtube 361 on with endoscope 3614 held in place by the vacuum;
m) Vacuum application to both fluid collection elements 3613E and 3613V;
n) Straightening maneuvers by retracting fluid collection element 3613E together with fluid collection element 3613V, both subject to the vacuum;

Thereafter, the examination can be continued using Step i) and following.

FIG. 37 is a representation of a fluid collection element (a vacuum drainage device) in the form of a sponge body 371 with partial surface seal 374 of sponge body 371. Into a drainage hose 372, which is introduced into sponge body 371, a guidewire 373 is introduced in this representation.

FIG. 38 is a longitudinal section of fluid collection element 371 of FIG. 37. The surface seal 374 of sponge body 371 with drainage hose 372, which has lateral perforation openings 372a and into which a guidewire 373 is introduced, are shown.

FIG. 39 is a representation of a different embodiment of a vacuum drainage device 391 with a drainage hose 392 and a guidewire 393 situated therein. On the outside of sponge body 391, a bowl-shaped seal 395 is arranged, which has a funnel-shaped flare 395a at its proximal end.

FIG. 40 is a longitudinal section of the vacuum drainage device 391 of FIG. 39 and also shows the bowl-shaped seal 395 on the outside of the sponge body of vacuum drainage device 391 which is flared funnel-like at the proximal end (395a). Also shown is drainage hose 392, which has lateral perforation openings 392a and in which a guidewire 393 is situated.

FIG. 41 is a representation of a vacuum drainage device in the form of a sponge body 411 having a profiled surface seal 416 of sponge body 411. In drainage hose 412, a guidewire 413 is introduced. The surface seal 416 has a riffled profile 416a with longitudinal grooves running side by side in the longitudinal direction of sponge body 411.

FIG. 42 is a cross section of the vacuum drainage device of FIG. 41. In drainage hose 412, guidewire 413 is situated. The surface seal shows its longitudinal profile 416a.

FIG. 43 is a representation of a vacuum drainage device having a tube 437 attached in sponge body 431. Into sponge body 431, a drainage hose 432 is inserted, in which a guidewire 433 is situated. At the proximal end of the vacuum drainage device, a funnel-shaped flare 437a exists. Into tube 437, an insertion rod 438 is introduced, which is conically tapered at its distal end 438a. Into insertion rod 438, an additional guidewire is inserted. At the proximal end of the insertion rod, a pusher 439 is imposed.

FIG. 44 is a representation of a different embodiment of a vacuum drainage device having, attached in a sponge body 441, a tube 447, which has a funnel-shaped flare at its proximal end. In the tube, an endoscope 4410 is introduced. On the proximal end of endoscope 4410, a pusher 449 is imposed. Tube 447, sponge body 441 and pusher 449 are provided with a complete lateral longitudinal slot 4412. In sponge body 4411, a drainage hose 442 is inserted; in it, a guidewire 443 is situated.

FIG. 45 is a longitudinal section of the vacuum drainage device of FIG. 43. In sponge body 431 lies tube 437, which has its funnel-like flare 437a at the proximal end. In tube 437, insertion rod 438 is situated. In insertion rod 438, a guidewire 433 is introduced. On the insertion rod, pusher 439 is imposed. In sponge body 431 lies the drainage hose 432 with lateral openings 432a. In drainage hose 432 lies an additional guidewire 433a.

FIG. 46 is a representation of an additional embodiment of a vacuum drainage device with drainage hose 462 in sponge body 461. In the sponge body of the vacuum drainage device, a tube 467 is situated, which has proximal and distally split ends 467b. Arrows indicate, in which direction the split ends 467b can open.

FIG. 47 is a longitudinal section of an additional vacuum drainage device having, situated in sponge body 471, a tube which, subject to suction, can be opened outward by its ends 477b. Into tube 477, an endoscope 4710 is introduced. In sponge body 471 lies a drainage hose 472 with lateral openings 472a. The vacuum drainage device is situated in a section of the intestine, of which an intestinal wall 4713 is indicated.

FIG. 48 is a representation of the vacuum drainage device of FIG. 47, in this representation, a negative pressure being applied to drainage hose 472. Sponge body 471 has, therefore, collapsed and intestinal wall 4713 abuts sponge body 471. Movable ends 477b of tube 477 are folded outward in the direction of the arrows.

FIG. 49 is a representation of an additional embodiment of a vacuum drainage (device), which is identified as sponge drainage (device), with the same meaning, within the framework of the application herein. A sponge body 491 is attached to a drainage hose 492a. Drainage hose 492 exits proximally and distally from the sponge body. Into drainage hose 492a, a guidewire 493 was introduced.

FIG. 50 is a cross-section of the sponge drainage device of FIG. 49. Sponge body 491 is attached on drainage hose 492a above the perforation openings 494. A guidewire 493 is introduced into the drainage hose.

FIG. 51 is a representation of an additional embodiment of a sponge drainage device. Two sponge bodies 511 are attached on a drainage hose 512a at a (certain) distance (from each other). Into drainage hose 512a, a guidewire 513 was introduced. This embodiment is advantageous, if, for instance, a section of the intestine is to be functionally disabled by means of a fistula.

FIG. 52 is a cross-section of the sponge of the drainage device of FIG. 51. The two sponge bodies, attached at a distance (from each other) on drainage hose 512a above perforation openings 514, are recognizable. Guidewire 513 is introduced into the drainage hose.

FIG. 53 is a representation of an additional embodiment of a sponge drainage device. A sponge body 531 is attached on a drainage hose 532a. Drainage hose 532a tapers to form a small-lumen drainage hose 532b. In the drainage hose, a guidewire 533 is introduced.

FIG. 54 is a cross-section of the sponge drainage device of FIG. 53. Sponge body 531 is attached on drainage hose 532a above perforation openings 534. Drainage hose 532a tapers toward a small-lumen drainage hose 532b. Guidewire 533 is introduced into the drainage hose.

FIGS. 55 a to h show different variants of a distal end of a sponge drainage device 551, each in a corresponding cross-section. Sponge body 551 is attached on a drainage hose 552a above perforation opening 554. Drainage hose 552a ends in a tip 555. In FIG. 55a, a string 556 is attached to tip 555. In FIG. 55b, a string or wire loop 557 is attached to tip 555. In FIG. 55c, a string 556 is attached to tip 555. Here, however, the tip has a channel 558, through which a guidewire 553 can be conducted. In FIG. 55d, sponge body 551 is designed as a tip at its distal end. Here, too, the sponge body has a channel 558, through which a guidewire was installed. In FIG. 55e, sponge body 551 is also designed as a tip at the distal end. Sponge body 551 has a channel 558, through which a guidewire 553 was installed. To the sponge body, a string or wire loop 57 is attached. In FIG. 55f, a grasping bead 559 is attached to tip 555. In FIG. 55g, at the tip, an eyelet 5510 is attached, through which a string 5511 was pulled. In FIG. 55h, grasping bead 559 lies in sponge body 551.

FIGS. 56 a to f are different representations of a drainage hose 562a and pointed top-seated attachments 5612. FIG. 56a is a representation of a drainage hose 562a and a pointed top-seated attachment 5612. The pointed top-seated attachment has, at its distal end, a grasping bead 569, at the proximal end a screw string 5612a. FIG. 56b is a representation, in which pointed top-seated attachment 5612 is screwed to drainage hose 562a. FIG. 56c is a longitudinal section of FIG. 56a with drainage hose 562a and pointed top-seated attachment 5612. FIG. 56d is a longitudinal section of FIG. 56c with pointed top-seated attachment 5612 screwed onto drainage hose 562. FIG. 56e is a longitudinal section of pointed top-seated attachment 5612 which is screwed onto drainage hose 562a and is equipped with a transverse channel 5612b. FIG. 56f is a longitudinal section of a variant of pointed top-seated attachment 5612 which is screwed onto drainage channel 562a. The pointed top-seated attachment is equipped with a channel 5612c. Through channel 5612c and the drainage hose, a guidewire 563 is inserted.

Hereinafter, new insertion instruments are described which are suitable for vacuum endoscopy.

Endoscopic insertion or grasping instruments are used for the placement of vacuum drainage devices. The placement can either be made using an orthograde forward-push technique or a pull-(through) technique. When using orthograde placement, an endoscopic insertion instrument is introduced into the working channel of the endoscope and an outer working channel. It is performed on the distal end of the endoscope. The placement of the drainage device using the pull-(through) technique is used, if the wound to be treated can, on the one hand, be endoscopically reached from the inside via a natural or artificial access route and, on the other hand, an additional external access route, for example in the form of an external fistula, exists.

The pull-(through) technique is also used, if the endoscopic vacuum therapy is used in combination with open or laparothoracoscopic surgery (rendezvous procedure). It can also be used for inserting conventional drains in laparoscopy.

Based on a therapy example in the case of esophageal leakage with outward fistulization, the pull-through technique will be explained. Using a guidewire or an endoscope, the insertion instrument will be preplaced from the outside above the fistula opening up to the esophagus. At the same time, an endoscope is inserted through the mouth into the esophagus and moved forward to the leakage point. When the insertion instrument has arrived at the leak of the esophagus, it is grasped using a loop and moved back out retrograde through the mouth. The insertion instrument will be coupled and attached by its attachment mechanism to the distal end of the fluid communication element, the pointed top-seated attachment or the sponge body. Under endoscopic vision, the insertion instrument is then subjected to a pull, the drainage occurs subject to pull by way of the mouth into the esophagus. The exact positioning is endoscopically controlled via the esophagus. The insertion instrument will be detached from the coupling to the drainage device and removed by further pulling. If the tip of the fluid communication element, the pointed top-seated attachment or the sponge body is reinforced by a string, the maneuver above can be performed using the string subject to application of the above technique.

The application of the pull-(through) procedure is particularly advantageous if a drainage device design was selected, in which the sponge body lies in the central section of the fluid communication element. In that case, the sponge body can be positioned by pulling on one end of the fluid communication element. Aspiration is then possible via only one leg of the fluid communication element, simultaneously via both legs or alternating.

The insertion instrument consists of a bead grabber. In a plastic sleeve, a metal or plastic core is introduced. The distal end of the core splits into two or a plurality of leaves. At the distal end of the core, an outward tension of the leaves exists so that it opens blossom-like when it emerges from the distal end of the sleeve and closes during retraction into the sleeve. At their ends, the leaves are molded spoon-like, so that upon closing of the core, a spherical or lenticular cavity forms. At the distal end, after closing, a small opening remains. Into the blossom-like opened core, the grasping bead of the pointed top-seated attachment, the fluid communication element or the fluid collection element can be introduced. When the core is closed, the bead is firmly seated. During opening, it detaches easily again and insertion instrument and grasping bead are uncoupled.

It is particularly advantageous if the insertion instrument is designed to receive a guidewire. The bead grabber may be introduced into the working channel of an endoscope. The insertion instrument is particularly 80 cm to 250 cm long.

An additional insertion instrument consists of a hook. Into a plastic sleeve, a wire-like metal or plastic core is introduced. At the distal end, the core is provided with a hook, by means of which a string loop or an eyelet can be grasped. After release of the hook from the sleeve, the string loop or eyelet of the pointed top-seated attachment, the fluid communication element or the fluid collection element can be attached by retracting the hook. Upon opening of the hook, the connection releases again. It is particularly advantageous to introduce a guidewire into the insertion instrument. The hook can be inserted into the working channel of an endoscope.

Furthermore, it has been found to be helpful to provide a grasping bead, string-wire loop, eyelet and/or a string, attached tension-proof, at the tip, in the latter case, the tip having a transverse channel, into which the string can be introduced.

FIGS. 57 a to f are different representations of an endoscopic insertion instrument 5713a/b, by means of which a grasping bead 579 can be grasped. FIG. 57a is a representation of an opened instrument. Out of a sleeve 5713a, a dual-leaf core 5713b, which has opened, is conducted out. Moreover, a guidewire 573 exits from the sleeve. In FIG. 57b, the guidewire 573 is retracted, the grasping bead 579 is grasped using core 5713b. FIG. 57c shows how the grasping bead was grasped. The core 5713b was retracted into sleeve 5713a; during this process, core 5713b has closed. In FIG. 57d, the closed core 5713b is represented having grasped grasping bead 579 and being retracted into sleeve 5713a. FIG. 57e is a longitudinal section of 57a with sleeve 5713a, opened core 5713b, guidewire 573 and grasping bead 579. FIG. 57f is a longitudinal section of 57d. The closed core 5713b with the grasped grasping bead 579 has been retracted into sleeve 5713a.

FIGS. 58 a to e are different representations of an additional endoscopic insertion instrument, by means of which an eyelet 5810 can be grasped. FIG. 58a is a representation of the opened instrument. Out of a sleeve 5814a, a hook 5814b is conducted out. Moreover, a guidewire 583 is conducted out of the sleeve. In FIG. 58b, the guidewire 583 is withdrawn, the eyelet 5810 is grasped using hook 5814b. FIG. 58c shows how the hook was retracted into sleeve 5814a using the grasped eyelet 5810. FIG. 58d is a longitudinal section of the insertion instrument of FIG. 58a, with sleeve 5814a, hook 5814b, guidewire 583 and eyelet 5810. FIG. 58e is a longitudinal section of FIG. 58c. The hook 5814b has been retracted back into the sleeve 5814a using the grasped eyelet 5810.

FIG. 59 is a representation of insertion aid 591 with a sleeve 592 for attachment to a distal end of an endoscope. Insertion aid 591 is beveled at its distal end, the longer side of the bevel coming to lie on the endoscope, in order to avoid injury during insertion of the endoscope. At the proximal end, a valve 593 is located to prevent leakage of the examination gas.

60 is a representation with 2 insertion aids 601 of different sizes.

FIG. 61 shows a longitudinal section of an insertion aid 611, an attachment sleeve 612 with valve 613.

FIG. 62 shows a representation of an insertion aid 621 having an attachment sleeve 622 at a distal end of an endoscope 624

FIG. 63 is a representation of an insertion aid 631 having an attachment sleeve 632 at a distal end of an endoscope 634. Into the insertion aid, endoscopic forceps 635 were introduced.

The invention claimed is:

1. Vacuum system for endoscopic intracavitary intraluminal or intracorporeal vacuum therapy for aspirating body fluids, wound secretions or gases from a hollow space, such as a body cavity, a hollow organ, a tissue abscess or an intestinal lumen, in particular in creating of a temporary endoscopic closure of an intestinal lumen, the vacuum system comprising:

a vacuum pump having a control input for receiving a control signal for control of its vacuum and having, on its negative pressure side, a connection for a vacuum drainage arrangement, and connected or connectable to the control input of the vacuum pump, a pressure regulating unit, having a test signal input for receiving at least one pressure test signal, which provides a measure for a pressure or negative pressure prevailing at the hollow space to be treated and which is designed,

[upon specification]

a) *upon specification* of a negative pressure at the hollow space to be treated, being selectable from a predefined negative pressure value interval, and b) [of] an evacuation period[, the value of which, situated] between 0.5and 5seconds, [is selectable,]

i) figuring in a predetermined dead volume of the vacuum drainage device arrangement that is connectable to the vacuum pump, to determine a first suction capacity of the vacuum pump, required for generating the specified negative pressure at the hollow space to be treated within the specified evacuation period, and to transmit a corresponding first control signal to the control input of the vacuum pump, ii) upon generating the specified negative pressure at the hollow space to be treated, to monitor the pressure test signal and to determine, as a function of the current pressure test signal, a second suction capacity of the vacuum pump, required for maintaining the specified negative pressure, and to transmit a corresponding second control signal to the control input of the vacuum pump; and iii) upon generating the specified negative pressure at the hollow space to be treated, if a deviation of the measured pressure or negative pressure from the specified negative pressure exists that exceeds a pre-defined threshold of the measured pressure or negative pressure, to determine a third suction capacity that is required for generating the specified negative pressure within the specified evacuation period and to transmit an appropriate third control signal to the control input of the vacuum pump;

the vacuum pump being designed, as a function of the control signal currently being applied to its control input, to generate a suction capacity determined by the control signal.

2. Vacuum system according to claim 1, wherein the predetermined negative pressure value interval extends across negative pressure values relative to a surrounding pressure between a minimum negative pressure of 60mm Hg and a maximum negative pressure of 500mm Hg.

3. Vacuum system according to claim 1, [which] *wherein the evacuation period is selectable and the vacuum system* additionally comprises a user input unit connected to the pressure regulating unit and is designed to accept a user input of the evacuation period and/or a negative pressure value and to transmit it to the pressure regulating unit, and in which the pressure regulating unit is designed to determine the control signal concerned figuring in the current user input and to transmit it to the control input of the vacuum pump.

4. Vacuum system according to claim [1] *3*, wherein the user input unit has a lockable mode switch that allows user-side setting of either a therapy mode or an endoscopy mode, the pressure regulating unit being designed to output, in the therapy mode, only the second or third control signal, but not the first control signal, and the predefined negative pressure value interval in the therapy mode extending across negative pressure values relative to a surrounding pressure between a minimum negative pressure of 60 mm Hg and a maximum negative pressure of 250mm Hg.

5. Vacuum system according to claim 1, having a vacuum drainage arrangement which is connected to the vacuum pump on the negative pressure side and having a negative pressure-resistant secretion collection container, which is designed to accept and/or discharge secretions and gas that occur during operation and aspirated by the vacuum pump and in which the pressure regulating unit is designed to figure in a volume of the secretion collection container as part of the dead volume.

6. Vacuum system according to claim 5, in which the vacuum drainage device additionally has a presecretion collection container which is connected upstream of the secretion collecting container and is connected to it and fluid-conducting, and in which the pressure regulating unit is designed to figure in a volume of the secretion collection container as an additional part of the dead volume.

7. Vacuum system according to claim 5, wherein the pressure regulating unit is designed to figure in an additional volume, which embodies at least one negative pressure-resistant fluid communication element, in particular a drainage hose, which is distally connectable to a fluid collection element and proximally to the secretion collection container or the presecretion collection container as an additional part of the dead volume.

8. Vacuum system according to claim 1, wherein the vacuum pump comprises a pump combination of at least two pump units, of which a first pump unit is designed to generate a prevacuum that has a lower negative pressure than the specified negative pressure, and a second pump unit is designed to generate the vacuum after generating the prevacuum.

9. Vacuum system according to claim 1, wherein the pressure regulating unit is designed to initially and temporarily specify for the vacuum pump a predeterminable first higher negative pressure and after a period of time, determinable by user input, to adjust the negative pressure to a predeterminable second, comparably lower, negative pressure value.

10. Vacuum system according to claim 1, wherein the vacuum pump has a plurality of vacuum-side connections for both ends of a single drainage hose or one or a plurality of ends of a plurality of drainage hoses, and wherein the pressure regulating unit is designed to control the vacuum pump upon a corresponding user input via the user input unit so as to aspirate or flush optionally either unilaterally only one of the connections or alternating two of the ports or simultaneously two connections.

11. Endoscopy arrangement with a vacuum system according to claim 1, an overtube unit which is connected to the vacuum pump of the vacuum system on the negative pressure side by at least one fluid communication element and carries a fluid collection element, an endoscope which is introduced or introduceable into the overtube unit and is displaceable relative to the overtube unit in a direction facing from proximal to distal or vice-versa direction, and a negative pressure sensor which is connected to the pressure regulating unit of the vacuum system.

12. Endoscopy arrangement according to claim 11, wherein the endoscope is connected to the vacuum pump of the vacuum system on the negative pressure side by a fluid communication element in the form of drainage hoses and/or in the form of a channel in the endoscope and carries an additional fluid-collecting element.

13. Endoscopy arrangement according to claim [11] *12*, wherein the fluid collection element is attached to the distal end of the overtube unit and/or the additional fluid collection element to the distal end of the endoscope.

14. Endoscopy arrangement according to claim 12, wherein the endoscope has at least one working channel extending in its inside and having outward perforation openings, by means of which the additional fluid collection element is connected fluid-conductive.

15. Endoscopy arrangement according to claim [11] *12*, wherein the fluid collection element and the additional fluid collection element has a polyurethane sponge.

16. Endoscopy arrangement according to claim [11] *12*, wherein the fluid collection element or the additional fluid collection element is an open-pore fluid-conducting film or wherein the fluid collection element and the additional fluid collection element additionally has, on its outer surface, an open-pore fluid-conducting film.

17. Endoscopy arrangement according to claim 16, wherein the film is designed fluid-conductive in the direction of the endoscope.

18. Endoscopy arrangement according to [any of the] claim [11] *12*, wherein, as additional fluid collection element, the endoscope carries a polyurethane sponge, while the overtube unit, as fluid collection element, carries a film.

19. Endoscopy arrangement according to claim [11] *12*, [with a vacuum system according to claim 9] *wherein the pressure regulating unit is designed to initially and temporarily specify for the vacuum pump a predeterminable first higher negative pressure and after a period of time, determinable by user input, to adjust the negative pressure to a predeterminable second, comparatively lower, negative pressure value*, *and* wherein both longitudinal ends of the drainage hose have a port for connection to the vacuum pump and wherein the [sponge drainage unit] *fluid collection element* is attached between the longitudinal ends of the drainage hose.

20. Endoscopy arrangement according to claim 11, wherein the fluid collection element and/or the additional fluid collection element is provided with a surface seal for closing open pores in sections and in other sections does not have the surface seal.

21. Endoscopy arrangement according to [any of the] claim [11] *12*, wherein distally the drainage hose ends in a conical tip.

22. Endoscopy arrangement according to claim 21, wherein, at the tip of the drainage hose, a grasping bead, string-wire loop, eyelet and/or a string is attached tension-proof; wherein, in the latter case, the tip has a transverse channel, into which the string can be introduced.

23. Endoscopy arrangement according to claim 22, wherein the distal tip of the drainage hose is a projectile-like pointed top-seated attachment made of plastic or metal which is designed tension-proof, attachable, using a plug-in and/or screwed element, to the end of the drainage hose.

24. Endoscopy arrangement according to claim [11] *23*, wherein the drainage hose is designed to permit the introduction of a guidewire into the lumen of the drainage hose and wherein, for this purpose, a distal tip of the drainage hose and the pointed top-seated attachment has a longitudinal channel, into which the guidewire can be introduced.

25. Endoscopy arrangement according to any of the claim 11, wherein a sponge body of the fluid collection element ends distally in a tip and, at the tip and/or integrated into the sponge body, a grasping bead, string-wire loop, eyelet and/or string is attached tension-proof.

26. Endoscopy arrangement according to claim [11] *13*, wherein [one of the] *a* negative pressure [sensors] *sensor* is arranged in, on or at the distally arranged fluid collection element and is connected to the pressure regulating unit of the vacuum system.

27. Endoscopy arrangement according to claim 26, wherein [this] *the* negative pressure sensor is designed wire-shaped and is conducted to the fluid collection element via the drainage hose.

28. Endoscopy arrangement according to claim 11, wherein the overtube has, proximally and distally directly adjacent to the fluid collection element seated on it, in each case, an annular lip-like thickening.

29. Endoscopy arrangement according to claim [11] *12*, wherein, in different longitudinal sections, the drainage hose has different diameters.

30. Endoscopy arrangement according to claim 11, wherein the fluid collection element has a sponge body, which has, on its outer surface, at least one recess or, in its inside, a channel for receiving a sensor, which, for operating the endoscopy arrangement, can be inserted into the recess or the channel.

31. Endoscopy arrangement according to claim [11] *30*, wherein, in [a] *the* sponge body of the fluid collection element, a channel running from proximal to distal, is arranged, through which runs a tube not connected fluid-conductive to pores of the sponge body for passage of body fluids such as secretions or saliva.

32. Endoscopy arrangement according to claim 31, wherein the tube is negative pressure-resistant and has a length of 5cm to 20cm and an inside diameter of 5mm to 20cm.

33. Endoscopy arrangement according to claim 31, wherein the tube is internally hydrophilic and wherein a surface seal of the fluid collection element are hydrophilic.

34. Endoscopy arrangement according to claim 31, wherein a proximal and/or a distal end of the tube relative to a central section of the tube are movable outward and spreadable open subject to negative pressure application.

35. Endoscopy arrangement according to claim 31, wherein the tube lies in the channel without any attachment.

36. Endoscopy arrangement according to claim 11, wherein the outside diameter of the fluid communication element and the fluid collection element are adapted to an inside diameter of an inner working channel of the endoscope in such a way that they are displaceable within the working channel and their placement can be achieved via the inner working channel of the endoscope.

37. Endoscopy arrangement according to claim 11, wherein the fluid collection element has a sponge body, and a channel situated in the sponge body is provided with a surface seal, which is made of a longitudinally profiled film which is profiled by fluid-conducting channels in a direction going from proximal to distal.

38. Endoscopy arrangement according to claim 11, wherein the overtube[.] *and* the fluid collection element[, the pusher and the outer working channel] are provided with a longitudinal slot that extends over the entire length.

* * * * *